United States Patent
Zarins et al.

(10) Patent No.: US 10,039,596 B2
(45) Date of Patent: Aug. 7, 2018

(54) APPARATUS FOR RENAL NEUROMODULATION VIA AN INTRA-TO-EXTRAVASCULAR APPROACH

(71) Applicant: Medtronic Ardian Luxembourg S.a.r.l., Luxembourg (LU)

(72) Inventors: Denise Zarins, Saratoga, CA (US); Benjamin J. Clark, Redwood City, CA (US); Nicolas Zadno, Fremont, CA (US); Hanson Gifford, III, Woodside, CA (US); Erik Thai, San Jose, CA (US)

(73) Assignee: Medtronic Ardian Luxembourg S.a.r.l., Luxembourg (LU)

( * ) Notice: Subject to any disclaimer, the term of this patent is extended or adjusted under 35 U.S.C. 154(b) by 0 days.

(21) Appl. No.: 15/132,445

(22) Filed: Apr. 19, 2016

(65) Prior Publication Data
US 2017/0014178 A1    Jan. 19, 2017

Related U.S. Application Data

(60) Continuation of application No. 14/574,262, filed on Dec. 17, 2014, now Pat. No. 9,364,280, which is a
(Continued)

(51) Int. Cl.
*A61N 1/36* (2006.01)
*A61B 18/14* (2006.01)
(Continued)

(52) U.S. Cl.
CPC ...... *A61B 18/1477* (2013.01); *A61B 18/1206* (2013.01); *A61M 5/14* (2013.01);
(Continued)

(58) Field of Classification Search
CPC ...... A61N 1/0551; A61N 1/3787; A61N 1/05; A61N 1/36057; A61N 1/0558;
(Continued)

(56) References Cited

U.S. PATENT DOCUMENTS 2,130,758 A    9/1938  Rose
2,276,995 A    3/1942  Milinowski
(Continued)

FOREIGN PATENT DOCUMENTS

DE    3151180    8/1982
EP    0811395    12/1997
(Continued)

OTHER PUBLICATIONS

"2011 Edison Award Winners." Edison Awards: Honoring Innovations & Innovators, 2011, 6 pages, <http://www.edisonawards.com/BestNewProduct_2011.php>.
(Continued)

*Primary Examiner* — Deborah Malamud

(57) ABSTRACT

Methods and apparatus are provided for pulsed electric field neuromodulation via an intra-to-extravascular approach, e.g., to effectuate irreversible electroporation or electrofusion, necrosis and/or inducement of apoptosis, alteration of gene expression, changes in cytokine upregulation and other conditions in target neural fibers. In some embodiments, the ITEV PEF system comprises an intravascular catheter having one or more electrodes configured for intra-to-extravascular placement across a wall of patient's vessel into proximity with target neural fibers. With the electrode(s) passing from an intravascular position to an extravascular position prior to delivery of the PEF, a magnitude of applied voltage or energy delivered via the electrode(s) and necessary to achieve desired neuromodulation may be reduced relative to an intravascular PEF system having one or more electrodes positioned solely intravascularly. The methods and apparatus of the present invention may, for example, be used to modulate one or more target neural fibers that contribute to renal function.

18 Claims, 19 Drawing Sheets

Related U.S. Application Data division of application No. 13/007,370, filed on Jan. 14, 2011, now Pat. No. 8,958,871, which is a continuation of application No. 12/616,708, filed on Nov. 11, 2009, now Pat. No. 7,873,417, which is a continuation of application No. 11/363,867, filed on Feb. 27, 2006, now Pat. No. 7,620,451, which is a continuation-in-part of application No. 11/129,765, filed on May 13, 2005, now Pat. No. 7,653,438, which is a continuation-in-part of application No. 10/408,665, filed on Apr. 8, 2003, now Pat. No. 7,162,303, said application No. 11/363,867 is a continuation-in-part of application No. 11/189,563, filed on Jul. 25, 2005, now Pat. No. 8,145,316, and a continuation-in-part of application No. 11/266,993, filed on Nov. 4, 2005, now Pat. No. 7,756,583.

(60) Provisional application No. 60/813,589, filed on Dec. 29, 2005, provisional application No. 60/616,254, filed on Oct. 5, 2004, provisional application No. 60/624,793, filed on Nov. 2, 2004, provisional application No. 60/442,970, filed on Jan. 29, 2003, provisional application No. 60/415,575, filed on Oct. 3, 2002, provisional application No. 60/370,190, filed on Apr. 8, 2002.

(51) Int. Cl.
| | | |
|---|---|---|
| *A61N 1/05* | (2006.01) | |
| *A61N 1/32* | (2006.01) | |
| *A61B 18/12* | (2006.01) | |
| *A61M 5/14* | (2006.01) | |
| *A61M 37/00* | (2006.01) | |
| *A61B 18/00* | (2006.01) | |

(52) U.S. Cl.
CPC .............. *A61M 37/00* (2013.01); *A61N 1/05* (2013.01); *A61N 1/0514* (2013.01); *A61N 1/0551* (2013.01); *A61N 1/321* (2013.01); *A61N 1/327* (2013.01); *A61N 1/36007* (2013.01); *A61B 2018/0022* (2013.01); *A61B 2018/00267* (2013.01); *A61B 2018/00404* (2013.01); *A61B 2018/00434* (2013.01); *A61B 2018/00505* (2013.01); *A61B 2018/00613* (2013.01); *A61B 2018/126* (2013.01)

(58) Field of Classification Search
CPC .............. A61N 1/3606; A61N 1/36014; A61N 1/3605; A61N 1/36125; A61N 1/3727; A61N 1/36189; A61N 1/056; A61N 1/057; A61N 1/08; A61N 1/37; A61N 1/375; A61N 1/0472; A61B 2018/00434; A61B 5/0031; A61B 2562/16; A61B 2562/227; A61B 18/1206; A61B 2018/00214; A61B 2018/0022; A61B 2018/00267; A61B 5/0215; A61B 5/0538; A61B 18/16; A61B 19/00; A61B 5/042; A61B 5/14503; A61B 5/4035; A61B 5/4848; A61B 5/6846; A61B 5/686; A61B 5/6882

See application file for complete search history.

(56) References Cited

U.S. PATENT DOCUMENTS

| | | |
|---|---|---|
| 2,276,996 A | 3/1942 | Milinowski |
| 3,043,310 A | 7/1962 | Milinowski |
| 3,127,895 A | 4/1964 | Kendall et al. |
| 3,181,535 A | 5/1965 | Milinowski |
| 3,270,746 A | 9/1966 | Kendall et al. |
| 3,329,149 A | 7/1967 | Kendall et al. |
| 3,522,811 A | 8/1970 | Schwartz et al. |
| 3,563,246 A | 2/1971 | Puharich et al. |
| 3,650,277 A | 3/1972 | Sjostrand et al. |
| 3,670,737 A | 6/1972 | Pearo |
| 3,760,812 A | 9/1973 | Timm et al. |
| 3,774,620 A | 11/1973 | Hansjurgens et al. |
| 3,794,022 A | 2/1974 | Nawracaj et al. |
| 3,800,802 A | 4/1974 | Berry et al. |
| 3,803,463 A | 4/1974 | Cover |
| 3,894,532 A | 7/1975 | Morey |
| 3,895,639 A | 7/1975 | Rodler et al. |
| 3,897,789 A | 8/1975 | Blanchard |
| 3,911,930 A | 10/1975 | Hagfors et al. |
| 3,952,751 A | 4/1976 | Yarger |
| 3,987,790 A | 10/1976 | Eckenhoff et al. |
| 4,011,861 A | 3/1977 | Enger |
| 4,026,300 A | 5/1977 | DeLuca et al. |
| 4,055,190 A | 10/1977 | Tany et al. |
| 4,071,033 A | 1/1978 | Nawracaj et al. |
| 4,105,017 A | 8/1978 | Ryaby et al. |
| 4,141,365 A | 2/1979 | Fischell et al. |
| 4,266,532 A | 5/1981 | Ryaby et al. |
| 4,266,533 A | 5/1981 | Ryaby et al. |
| 4,305,115 A | 12/1981 | Armitage et al. |
| 4,315,503 A | 2/1982 | Ryaby et al. |
| 4,360,019 A | 11/1982 | Portner et al. |
| 4,379,462 A | 4/1983 | Borkan et al. |
| 4,405,305 A | 9/1983 | Stephen et al. |
| 4,454,883 A | 6/1984 | Fellus et al. |
| 4,467,808 A | 8/1984 | Brighton et al. |
| 4,487,603 A | 12/1984 | Harris |
| 4,530,840 A | 7/1985 | Tice et al. |
| 4,587,975 A | 5/1986 | Salo et al. |
| 4,602,624 A | 7/1986 | Naples et al. |
| 4,608,985 A | 9/1986 | Crish et al. |
| 4,649,936 A | 3/1987 | Ungar et al. |
| 4,671,286 A | 6/1987 | Renault et al. |
| 4,674,482 A | 6/1987 | Waltonen et al. |
| 4,692,147 A | 9/1987 | Duggan |
| 4,709,698 A | 12/1987 | Johnston et al. |
| 4,715,852 A | 12/1987 | Reinicke et al. |
| 4,774,967 A | 10/1988 | Zanakis et al. |
| 4,791,931 A | 12/1988 | Slate |
| 4,816,016 A | 3/1989 | Schulte et al. |
| 4,852,573 A | 8/1989 | Kennedy |
| 4,865,845 A | 9/1989 | Eckenhoff et al. |
| 4,890,623 A | 1/1990 | Cook et al. |
| 4,976,711 A | 12/1990 | Parins et al. |
| 4,979,511 A | 12/1990 | Terry, Jr. |
| 4,981,146 A | 1/1991 | Bertolucci |
| 4,998,532 A | 3/1991 | Griffith |
| 5,006,119 A | 4/1991 | Acker et al. |
| 5,014,699 A | 5/1991 | Pollack et al. |
| 5,019,034 A | 5/1991 | Weaver et al. |
| 5,057,318 A | 10/1991 | Magruder et al. |
| 5,058,584 A | 10/1991 | Bourgeois et al. |
| 5,059,423 A | 10/1991 | Magruder et al. |
| 5,061,492 A | 10/1991 | Okada et al. |
| 5,094,242 A | 3/1992 | Gleason et al. |
| 5,111,815 A | 5/1992 | Mower |
| 5,112,614 A | 5/1992 | Magruder et al. |
| 5,125,928 A | 6/1992 | Parins et al. |
| 5,131,409 A | 7/1992 | Lobarev et al. |
| 5,137,727 A | 8/1992 | Eckenhoff |
| 5,188,837 A | 2/1993 | Domb |
| 5,193,048 A | 3/1993 | Kaufman et al. |
| 5,193,539 A | 3/1993 | Schulman et al. |
| 5,193,540 A | 3/1993 | Schulman et al. |
| 5,199,428 A | 4/1993 | Obel et al. |
| 5,203,326 A | 4/1993 | Collins et al. |
| 5,213,098 A | 5/1993 | Bennett et al. |
| 5,215,086 A | 6/1993 | Terry, Jr. et al. |
| 5,231,988 A | 8/1993 | Wernicke et al. |
| 5,234,692 A | 8/1993 | Magruder et al. |
| 5,234,693 A | 8/1993 | Magruder et al. |
| 5,251,634 A | 10/1993 | Weinberg |

(56) References Cited

U.S. PATENT DOCUMENTS

| | | |
|---|---|---|
| 5,251,643 A | 10/1993 | Osypka et al. |
| 5,263,480 A | 11/1993 | Wernicke et al. |
| 5,269,303 A | 12/1993 | Wernicke et al. |
| 5,282,468 A | 2/1994 | Klepinski |
| 5,282,785 A | 2/1994 | Shapland et al. |
| 5,286,254 A | 2/1994 | Shapland et al. |
| 5,299,569 A | 4/1994 | Wernicke et al. |
| 5,300,068 A | 4/1994 | Rosar et al. |
| 5,304,120 A | 4/1994 | Crandell et al. |
| 5,304,206 A | 4/1994 | Baker, Jr. et al. |
| 5,317,155 A | 5/1994 | King |
| 5,324,255 A | 6/1994 | Passafaro et al. |
| 5,324,316 A | 6/1994 | Schulman et al. |
| 5,334,193 A | 8/1994 | Nardella |
| 5,335,657 A | 8/1994 | Terry, Jr. et al. |
| 5,338,662 A | 8/1994 | Sadri |
| 5,351,394 A | 10/1994 | Weinberg |
| 5,354,279 A | 10/1994 | Hofling |
| 5,358,514 A | 10/1994 | Schulman et al. |
| 5,368,591 A | 11/1994 | Lennox et al. |
| 5,370,680 A | 12/1994 | Proctor |
| 5,389,069 A | 2/1995 | Weaver |
| 5,397,308 A | 3/1995 | Ellis et al. |
| 5,397,338 A | 3/1995 | Grey et al. |
| 5,400,784 A | 3/1995 | Durand et al. |
| 5,405,367 A | 4/1995 | Schulman et al. |
| 5,423,744 A | 6/1995 | Gencheff et al. |
| 5,425,364 A | 6/1995 | Imran |
| 5,429,634 A | 7/1995 | Narciso, Jr. |
| 5,433,739 A | 7/1995 | Sluijter et al. |
| 5,439,440 A | 8/1995 | Hofmann |
| 5,454,782 A | 10/1995 | Perkins |
| 5,454,809 A | 10/1995 | Janssen |
| 5,458,568 A | 10/1995 | Racchini et al. |
| 5,458,626 A | 10/1995 | Krause |
| 5,458,631 A | 10/1995 | Xavier |
| 5,470,352 A | 11/1995 | Rappaport |
| 5,472,406 A | 12/1995 | de la Torre et al. |
| 5,478,303 A | 12/1995 | Foley-Nolan et al. |
| 5,484,400 A | 1/1996 | Edwards et al. |
| 5,494,822 A | 2/1996 | Sadri |
| 5,498,238 A | 3/1996 | Shapland et al. |
| 5,499,971 A | 3/1996 | Shapland et al. |
| 5,505,700 A | 4/1996 | Leone et al. |
| 5,507,724 A | 4/1996 | Hofmann et al. |
| 5,507,791 A | 4/1996 | Sit'ko |
| 5,531,778 A | 7/1996 | Maschino et al. |
| 5,540,730 A | 7/1996 | Terry, Jr. et al. |
| 5,540,734 A | 7/1996 | Zabara |
| 5,560,360 A | 10/1996 | Filler et al. |
| 5,569,198 A | 10/1996 | Racchini |
| 5,571,147 A | 11/1996 | Sluijter et al. |
| 5,571,150 A | 11/1996 | Wernicke et al. |
| 5,573,552 A | 11/1996 | Hansjurgens et al. |
| 5,584,863 A | 12/1996 | Rauch et al. |
| 5,588,964 A | 12/1996 | Imran et al. |
| 5,589,192 A | 12/1996 | Okabe et al. |
| 5,599,345 A | 2/1997 | Edwards et al. |
| 5,618,563 A | 4/1997 | Berde et al. |
| 5,626,576 A | 5/1997 | Janssen |
| 5,626,862 A | 5/1997 | Brem et al. |
| 5,628,730 A | 5/1997 | Shapland et al. |
| 5,634,462 A | 6/1997 | Tyler et al. |
| 5,634,899 A | 6/1997 | Shapland et al. |
| 5,672,174 A | 9/1997 | Gough et al. |
| 5,688,266 A | 11/1997 | Edwards et al. |
| 5,689,877 A | 11/1997 | Grill, Jr. et al. |
| 5,690,691 A | 11/1997 | Chen et al. |
| 5,700,282 A | 12/1997 | Zabara |
| 5,700,485 A | 12/1997 | Berde et al. |
| 5,704,908 A | 1/1998 | Hofmann et al. |
| 5,707,400 A | 1/1998 | Terry, Jr. et al. |
| 5,711,326 A | 1/1998 | Thies et al. |
| 5,713,847 A | 2/1998 | Howard, III et al. |
| 5,722,401 A | 3/1998 | Pietroski et al. |
| 5,723,001 A | 3/1998 | Pilla et al. |
| 5,725,563 A | 3/1998 | Klotz et al. |
| 5,728,396 A | 3/1998 | Peery et al. |
| 5,747,060 A | 5/1998 | Sackler et al. |
| 5,749,914 A | 5/1998 | Janssen |
| 5,755,750 A | 5/1998 | Petruska et al. |
| 5,756,115 A | 5/1998 | Moo-Young et al. |
| 5,772,590 A | 6/1998 | Webster, Jr. |
| 5,792,187 A | 8/1998 | Adams |
| 5,800,464 A | 9/1998 | Kieval |
| 5,807,306 A | 9/1998 | Shapland et al. |
| 5,810,802 A | 9/1998 | Panescu et al. |
| 5,814,079 A | 9/1998 | Kieval |
| 5,824,087 A | 10/1998 | Aspden et al. |
| 5,836,935 A | 11/1998 | Ashton et al. |
| RE35,987 E | 12/1998 | Harris et al. |
| 5,843,069 A | 12/1998 | Butler et al. |
| 5,860,974 A | 1/1999 | Abele |
| 5,861,021 A | 1/1999 | Thome et al. |
| 5,865,787 A | 2/1999 | Shapland et al. |
| 5,871,449 A | 2/1999 | Brown |
| 5,891,181 A | 4/1999 | Zhu et al. |
| 5,893,885 A | 4/1999 | Webster, Jr. |
| 5,906,636 A | 5/1999 | Casscells, III et al. |
| 5,906,817 A | 5/1999 | Moullier et al. |
| 5,913,876 A | 6/1999 | Taylor et al. |
| 5,916,154 A | 6/1999 | Hobbs et al. |
| 5,916,239 A | 6/1999 | Geddes et al. |
| 5,919,187 A | 7/1999 | Guglielmi et al. |
| 5,924,997 A | 7/1999 | Campbell |
| 5,928,272 A | 7/1999 | Adkins et al. |
| 5,935,075 A | 8/1999 | Casscells et al. |
| 5,944,710 A | 8/1999 | Dev et al. |
| 5,954,719 A | 9/1999 | Chen et al. |
| 5,983,131 A | 11/1999 | Weaver et al. |
| 5,983,141 A | 11/1999 | Sluijter et al. |
| 6,004,269 A | 12/1999 | Crowley et al. |
| 6,006,134 A | 12/1999 | Hill et al. |
| 6,009,877 A | 1/2000 | Edwards |
| 6,010,613 A | 1/2000 | Walters et al. |
| 6,024,740 A | 2/2000 | Lesh et al. |
| 6,026,326 A | 2/2000 | Bardy |
| 6,036,687 A | 3/2000 | Laufer et al. |
| 6,041,252 A | 3/2000 | Walker et al. |
| 6,051,017 A | 4/2000 | Loeb et al. |
| 6,058,328 A | 5/2000 | Levine et al. |
| 6,058,331 A | 5/2000 | King |
| 6,066,134 A | 5/2000 | Eggers et al. |
| 6,073,048 A | 6/2000 | Kieval et al. |
| 6,077,227 A | 6/2000 | Miesel et al. |
| 6,086,527 A | 7/2000 | Talpade |
| 6,091,995 A | 7/2000 | Ingle et al. |
| 6,117,101 A | 9/2000 | Diederich et al. |
| 6,122,548 A | 9/2000 | Starkebaum et al. |
| 6,123,718 A | 9/2000 | Tu et al. |
| 6,135,999 A | 10/2000 | Fanton et al. |
| 6,142,993 A | 11/2000 | Whayne et al. |
| 6,146,380 A | 11/2000 | Racz et al. |
| 6,159,225 A | 12/2000 | Makower |
| 6,161,048 A | 12/2000 | Sluijter et al. |
| 6,171,306 B1 | 1/2001 | Swanson et al. |
| 6,178,349 B1 | 1/2001 | Kieval |
| 6,190,353 B1 | 2/2001 | Makower et al. |
| 6,192,889 B1 | 2/2001 | Morrish |
| 6,205,361 B1 | 3/2001 | Kuzma et al. |
| 6,208,894 B1 | 3/2001 | Schulman et al. |
| 6,214,032 B1 | 4/2001 | Loeb et al. |
| 6,219,577 B1 | 4/2001 | Brown, III et al. |
| 6,224,592 B1 | 5/2001 | Eggers et al. |
| 6,231,587 B1 | 5/2001 | Makower |
| 6,238,702 B1 | 5/2001 | Berde et al. |
| 6,245,026 B1 | 6/2001 | Campbell et al. |
| 6,246,912 B1 | 6/2001 | Sluijter et al. |
| 6,251,130 B1 | 6/2001 | Dobak, III et al. |
| 6,254,598 B1 | 7/2001 | Edwards et al. |
| 6,258,087 B1 | 7/2001 | Edwards et al. |
| 6,259,952 B1 | 7/2001 | Sluijter et al. |
| 6,269,269 B1 | 7/2001 | Ottenhoff et al. |
| 6,272,377 B1 | 8/2001 | Sweeney et al. |

(56) References Cited

U.S. PATENT DOCUMENTS

| | | |
|---|---|---|
| 6,272,383 B1 | 8/2001 | Grey et al. |
| 6,273,886 B1 | 8/2001 | Edwards et al. |
| 6,280,377 B1 | 8/2001 | Talpade |
| 6,283,947 B1 | 9/2001 | Mirzaee |
| 6,287,304 B1 | 9/2001 | Eggers et al. |
| 6,287,608 B1 | 9/2001 | Levin et al. |
| 6,292,695 B1 | 9/2001 | Webster, Jr. et al. |
| 6,304,777 B1 | 10/2001 | Ben-Haim et al. |
| 6,304,787 B1 | 10/2001 | Kuzma et al. |
| 6,306,423 B1 | 10/2001 | Donovan et al. |
| 6,314,325 B1 | 11/2001 | Fitz |
| 6,322,558 B1 | 11/2001 | Taylor et al. |
| 6,322,559 B1 | 11/2001 | Daulton et al. |
| 6,326,020 B1 | 12/2001 | Kohane et al. |
| 6,326,177 B1 | 12/2001 | Schoenbach et al. |
| 6,328,699 B1 | 12/2001 | Eigler et al. |
| 6,334,069 B1 | 12/2001 | George et al. |
| 6,347,247 B1 | 2/2002 | Dev et al. |
| 6,353,763 B1 | 3/2002 | George et al. |
| 6,356,786 B1 | 3/2002 | Rezai et al. |
| 6,356,787 B1 | 3/2002 | Rezai et al. |
| 6,366,808 B1 | 4/2002 | Schroeppel et al. |
| 6,366,815 B1 | 4/2002 | Haugland et al. |
| 6,393,324 B2 | 5/2002 | Gruzdowich et al. |
| 6,400,982 B2 | 6/2002 | Sweeney et al. |
| 6,405,079 B1 | 6/2002 | Ansarinia |
| 6,405,732 B1 | 6/2002 | Edwards et al. |
| 6,413,255 B1 | 7/2002 | Stern |
| 6,415,183 B1 | 7/2002 | Scheiner et al. |
| 6,415,187 B1 | 7/2002 | Kuzma et al. |
| 6,438,423 B1 | 8/2002 | Rezai et al. |
| 6,442,424 B1 | 8/2002 | Ben-Haim et al. |
| 6,449,507 B1 | 9/2002 | Hill et al. |
| 6,450,942 B1 | 9/2002 | Lapanashvili et al. |
| 6,461,314 B1 | 10/2002 | Pant et al. |
| 6,464,687 B1 | 10/2002 | Ishikawa et al. |
| 6,473,644 B1 | 10/2002 | Terry, Jr. et al. |
| 6,482,619 B1 | 11/2002 | Rubinsky et al. |
| 6,488,679 B1 | 12/2002 | Swanson et al. |
| 6,506,189 B1 | 1/2003 | Rittman, III et al. |
| 6,508,774 B1 | 1/2003 | Acker et al. |
| 6,514,226 B1 | 2/2003 | Levin et al. |
| 6,516,211 B1 | 2/2003 | Acker et al. |
| 6,517,811 B2 | 2/2003 | John et al. |
| 6,522,926 B1 | 2/2003 | Kieval et al. |
| 6,522,932 B1 | 2/2003 | Kuzma et al. |
| 6,524,607 B1 | 2/2003 | Goldenheim et al. |
| 6,534,081 B2 | 3/2003 | Goldenheim et al. |
| 6,536,949 B1 | 3/2003 | Heuser |
| 6,542,781 B1 | 4/2003 | Koblish et al. |
| 6,562,034 B2 | 5/2003 | Edwards et al. |
| 6,564,096 B2 | 5/2003 | Mest |
| 6,571,127 B1 | 5/2003 | Ben-Haim et al. |
| 6,592,567 B1 | 7/2003 | Levin et al. |
| 6,599,256 B1 | 7/2003 | Acker et al. |
| 6,600,954 B2 | 7/2003 | Cohen et al. |
| 6,600,956 B2 | 7/2003 | Maschino et al. |
| 6,601,459 B1 | 8/2003 | Jenni et al. |
| 6,605,084 B2 | 8/2003 | Acker et al. |
| 6,613,045 B1 | 9/2003 | Laufer et al. |
| 6,615,071 B1 | 9/2003 | Casscells, III et al. |
| 6,616,624 B1 | 9/2003 | Kieval |
| 6,620,151 B2 | 9/2003 | Blischak et al. |
| 6,622,041 B2 | 9/2003 | Terry, Jr. et al. |
| 6,622,731 B2 | 9/2003 | Daniel et al. |
| 6,635,054 B2 | 10/2003 | Fjield et al. |
| 6,640,120 B1 | 10/2003 | Swanson et al. |
| 6,654,636 B1 | 11/2003 | Dev et al. |
| 6,666,845 B2 | 12/2003 | Hooper et al. |
| 6,669,655 B1 | 12/2003 | Acker et al. |
| 6,671,556 B2 | 12/2003 | Osorio et al. |
| 6,672,312 B2 | 1/2004 | Acker |
| 6,676,657 B2 | 1/2004 | Wood |
| 6,681,136 B2 | 1/2004 | Schuler et al. |
| 6,684,105 B2 | 1/2004 | Cohen et al. |
| 6,690,971 B2 | 2/2004 | Schauerte et al. |
| 6,692,738 B2 | 2/2004 | MacLaughlin et al. |
| 6,697,670 B2 | 2/2004 | Chomenky et al. |
| 6,711,444 B2 | 3/2004 | Koblish et al. |
| 6,718,208 B2 | 4/2004 | Hill et al. |
| 6,735,471 B2 | 5/2004 | Hill et al. |
| 6,738,663 B2 | 5/2004 | Schroeppel et al. |
| 6,746,464 B1 | 6/2004 | Makower |
| 6,749,598 B1 | 6/2004 | Keren et al. |
| 6,752,805 B2 | 6/2004 | Maguire et al. |
| 6,786,904 B2 | 9/2004 | Doscher et al. |
| 6,795,728 B2 | 9/2004 | Chornenky et al. |
| 6,845,267 B2 | 1/2005 | Harrison et al. |
| 6,850,801 B2 | 2/2005 | Kieval et al. |
| 6,862,479 B1 | 3/2005 | Whitehurst et al. |
| 6,865,416 B2 | 3/2005 | Dev et al. |
| 6,869,431 B2 | 3/2005 | Maguire et al. |
| 6,885,888 B2 | 4/2005 | Rezai |
| 6,916,656 B2 | 7/2005 | Walters et al. |
| 6,917,834 B2 | 7/2005 | Koblish et al. |
| 6,923,808 B2 | 8/2005 | Taimisto et al. |
| 6,927,049 B2 | 8/2005 | Rubinsky et al. |
| 6,936,047 B2 | 8/2005 | Nasab et al. |
| 6,939,345 B2 | 9/2005 | KenKnight et al. |
| 6,939,346 B2 | 9/2005 | Kannenberg et al. |
| 6,949,097 B2 | 9/2005 | Stewart et al. |
| 6,958,060 B2 | 10/2005 | Mathiesen et al. |
| 6,969,388 B2 | 11/2005 | Goldman et al. |
| 6,972,013 B1 | 12/2005 | Zhang et al. |
| 6,978,174 B2 | 12/2005 | Gelfand et al. |
| 6,985,774 B2 | 1/2006 | Kieval et al. |
| 6,994,700 B2 | 2/2006 | Elkins et al. |
| 6,994,706 B2 | 2/2006 | Chornenky et al. |
| 7,004,911 B1 | 2/2006 | Tu et al. |
| 7,054,685 B2 | 5/2006 | Dimmer et al. |
| 7,063,679 B2 | 6/2006 | Maguire et al. |
| 7,081,114 B2 | 7/2006 | Rashidi |
| 7,081,115 B2 | 7/2006 | Taimisto |
| 7,083,614 B2 | 8/2006 | Fjield et al. |
| 7,122,019 B1 | 10/2006 | Kesten et al. |
| 7,155,284 B1 | 12/2006 | Whitehurst et al. |
| 7,162,303 B2 | 1/2007 | Levin et al. |
| 7,191,015 B2 | 3/2007 | Lamson et al. |
| 7,373,204 B2 | 5/2008 | Gelfand et al. |
| 7,407,506 B2 | 8/2008 | Makower |
| 7,444,183 B2 | 10/2008 | Knudson et al. |
| 7,617,005 B2 | 11/2009 | Demarais et al. |
| 7,620,451 B2 | 11/2009 | Demarais et al. |
| 7,647,115 B2 | 1/2010 | Levin et al. |
| 7,653,438 B2 | 1/2010 | Deem et al. |
| 7,717,948 B2 | 5/2010 | Demarais et al. |
| 7,729,738 B2 | 6/2010 | Flaherty et al. |
| 7,756,583 B2 | 7/2010 | Demarais et al. |
| 7,846,172 B2 | 12/2010 | Makower |
| 7,873,417 B2 | 1/2011 | Demarais et al. |
| 8,131,371 B2 | 3/2012 | Demarals et al. |
| 8,145,317 B2 | 3/2012 | Demarais et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 8,401,667 B2 | 3/2013 | Gustus et al. |
| 8,740,849 B1 | 6/2014 | Fischell et al. |
| 2001/0044596 A1 | 11/2001 | Jaafar |
| 2002/0002329 A1 | 1/2002 | Avitall |
| 2002/0026222 A1 | 2/2002 | Schauerte et al. |
| 2002/0026228 A1 | 2/2002 | Schauerte |
| 2002/0032468 A1 | 3/2002 | Hill et al. |
| 2002/0038137 A1 | 3/2002 | Stein |
| 2002/0040204 A1 | 4/2002 | Dev et al. |
| 2002/0045853 A1 | 4/2002 | Dev et al. |
| 2002/0065541 A1 | 5/2002 | Fredricks et al. |
| 2002/0072782 A1 | 6/2002 | Osorio et al. |
| 2002/0087208 A1 | 7/2002 | Koblish et al. |
| 2002/0107515 A1 | 8/2002 | Edwards et al. |
| 2002/0107553 A1 | 8/2002 | Hill et al. |
| 2002/0116030 A1 | 8/2002 | Rezai |
| 2002/0120304 A1 | 8/2002 | Mest |
| 2002/0139379 A1 | 10/2002 | Edwards et al. |
| 2002/0165532 A1 | 11/2002 | Hill et al. |

(56) References Cited

U.S. PATENT DOCUMENTS

| | | |
|---|---|---|
| 2002/0165586 A1 | 11/2002 | Hill et al. |
| 2002/0169413 A1 | 11/2002 | Keren et al. |
| 2002/0177846 A1 | 11/2002 | Mulier et al. |
| 2002/0183682 A1 | 12/2002 | Darvish et al. |
| 2002/0183684 A1 | 12/2002 | Dev et al. |
| 2002/0188325 A1 | 12/2002 | Hill et al. |
| 2002/0198512 A1 | 12/2002 | Seward |
| 2003/0004549 A1 | 1/2003 | Hill et al. |
| 2003/0009145 A1 | 1/2003 | Struijker-Boudier et al. |
| 2003/0018367 A1 | 1/2003 | DiLorenzo |
| 2003/0040774 A1 | 2/2003 | Terry et al. |
| 2003/0045909 A1 | 3/2003 | Gross et al. |
| 2003/0050635 A1 | 3/2003 | Truckai et al. |
| 2003/0050681 A1 | 3/2003 | Pianca et al. |
| 2003/0060848 A1 | 3/2003 | Kieval et al. |
| 2003/0060857 A1 | 3/2003 | Perrson et al. |
| 2003/0060858 A1 | 3/2003 | Kieval et al. |
| 2003/0074039 A1 | 4/2003 | Puskas |
| 2003/0100924 A1 | 5/2003 | Foreman et al. |
| 2003/0120270 A1 | 6/2003 | Acker |
| 2003/0125790 A1 | 7/2003 | Fastovsky et al. |
| 2003/0150464 A1 | 8/2003 | Casscells |
| 2003/0158584 A1 | 8/2003 | Cates et al. |
| 2003/0181897 A1 | 9/2003 | Thomas et al. |
| 2003/0181963 A1 | 9/2003 | Pellegrino et al. |
| 2003/0195507 A1 | 10/2003 | Stewart et al. |
| 2003/0199747 A1 | 10/2003 | Michlitsch et al. |
| 2003/0199767 A1 | 10/2003 | Cespedes et al. |
| 2003/0199768 A1 | 10/2003 | Cespedes et al. |
| 2003/0199806 A1 | 10/2003 | Kieval |
| 2003/0199863 A1 | 10/2003 | Swanson et al. |
| 2003/0204161 A1 | 10/2003 | Ferek-Petric |
| 2003/0216792 A1 | 11/2003 | Levin et al. |
| 2003/0220521 A1 | 11/2003 | Reitz et al. |
| 2003/0229340 A1 | 12/2003 | Sherry et al. |
| 2003/0233099 A1 | 12/2003 | Danaek et al. |
| 2003/0236443 A1 | 12/2003 | Cespedes et al. |
| 2004/0010289 A1 | 1/2004 | Biggs et al. |
| 2004/0010303 A1 | 1/2004 | Bolea et al. |
| 2004/0019364 A1 | 1/2004 | Kieval et al. |
| 2004/0019371 A1 | 1/2004 | Jaafar et al. |
| 2004/0064090 A1 | 4/2004 | Keren et al. |
| 2004/0064091 A1 | 4/2004 | Keren et al. |
| 2004/0065615 A1 | 4/2004 | Hooper et al. |
| 2004/0073238 A1 | 4/2004 | Makower |
| 2004/0082978 A1 | 4/2004 | Harrison et al. |
| 2004/0101523 A1 | 5/2004 | Reitz et al. |
| 2004/0106953 A1 | 6/2004 | Yomtov et al. |
| 2004/0111080 A1 | 6/2004 | Harper et al. |
| 2004/0127942 A1 | 7/2004 | Yomtov et al. |
| 2004/0162590 A1 | 8/2004 | Whitehurst et al. |
| 2004/0163655 A1 | 8/2004 | Gelfand et al. |
| 2004/0167415 A1 | 8/2004 | Gelfand et al. |
| 2004/0167509 A1 | 8/2004 | Taimisto |
| 2004/0176699 A1 | 9/2004 | Walker et al. |
| 2004/0176757 A1 | 9/2004 | Sinelnikov et al. |
| 2004/0193228 A1 | 9/2004 | Gerber |
| 2004/0215186 A1 | 10/2004 | Cornelius et al. |
| 2004/0215237 A1 | 10/2004 | Christopherson et al. |
| 2004/0220511 A1 | 11/2004 | Scott et al. |
| 2004/0243102 A1 | 12/2004 | Berg et al. |
| 2004/0243206 A1 | 12/2004 | Tadlock |
| 2004/0249416 A1 | 12/2004 | Yun et al. |
| 2004/0254616 A1 | 12/2004 | Rossing et al. |
| 2005/0010203 A1 | 1/2005 | Edwards et al. |
| 2005/0010263 A1 | 1/2005 | Schauerte |
| 2005/0021092 A1 | 1/2005 | Yun et al. |
| 2005/0038409 A1 | 2/2005 | Segal et al. |
| 2005/0049542 A1 | 3/2005 | Sigg et al. |
| 2005/0065562 A1 | 3/2005 | Rezai |
| 2005/0065573 A1 | 3/2005 | Rezai |
| 2005/0065574 A1 | 3/2005 | Rezai |
| 2005/0075681 A1 | 4/2005 | Rezai et al. |
| 2005/0080409 A1 | 4/2005 | Young et al. |
| 2005/0080459 A1 | 4/2005 | Jacobson et al. |
| 2005/0096647 A1 | 5/2005 | Steinke et al. |
| 2005/0096710 A1 | 5/2005 | Kieval |
| 2005/0153885 A1 | 7/2005 | Yun et al. |
| 2005/0154418 A1 | 7/2005 | Kieval et al. |
| 2005/0171523 A1 | 8/2005 | Rubinsky et al. |
| 2005/0171574 A1 | 8/2005 | Rubinsky et al. |
| 2005/0171575 A1 | 8/2005 | Dev et al. |
| 2005/0187579 A1 | 8/2005 | Danek et al. |
| 2005/0197624 A1 | 9/2005 | Goodson et al. |
| 2005/0209548 A1 | 9/2005 | Dev et al. |
| 2005/0209642 A1 | 9/2005 | Palti |
| 2005/0228460 A1 | 10/2005 | Levin et al. |
| 2005/0234523 A1 | 10/2005 | Levin et al. |
| 2005/0240126 A1 | 10/2005 | Foley et al. |
| 2005/0240173 A1 | 10/2005 | Palti |
| 2005/0240228 A1 | 10/2005 | Palti |
| 2005/0240241 A1 | 10/2005 | Yun et al. |
| 2005/0245882 A1 | 11/2005 | Elkins et al. |
| 2005/0245892 A1 | 11/2005 | Elkins et al. |
| 2005/0251212 A1 | 11/2005 | Kieval et al. |
| 2005/0261672 A1 | 11/2005 | Deem et al. |
| 2005/0267010 A1 | 12/2005 | Goodson et al. |
| 2005/0282284 A1 | 12/2005 | Rubinsky et al. |
| 2006/0004417 A1 | 1/2006 | Rossing et al. |
| 2006/0004430 A1 | 1/2006 | Rossing et al. |
| 2006/0025821 A1 | 2/2006 | Gelfand et al. |
| 2006/0030814 A1 | 2/2006 | Valencia et al. |
| 2006/0036218 A1 | 2/2006 | Goodson et al. |
| 2006/0041277 A1 | 2/2006 | Deem et al. |
| 2006/0041283 A1 | 2/2006 | Gelfand et al. |
| 2006/0067972 A1 | 3/2006 | Kesten et al. |
| 2006/0069323 A1 | 3/2006 | Elkins et al. |
| 2006/0074453 A1 | 4/2006 | Kieval et al. |
| 2006/0079859 A1 | 4/2006 | Elkins et al. |
| 2006/0085046 A1 | 4/2006 | Rezai et al. |
| 2006/0085054 A1 | 4/2006 | Zikorus et al. |
| 2006/0089674 A1 | 4/2006 | Walters et al. |
| 2006/0095029 A1 | 5/2006 | Young et al. |
| 2006/0100618 A1 | 5/2006 | Chan et al. |
| 2006/0100667 A1 | 5/2006 | Machado et al. |
| 2006/0106429 A1 | 5/2006 | Libbus et al. |
| 2006/0111754 A1 | 5/2006 | Rezai et al. |
| 2006/0116720 A1 | 6/2006 | Knoblich |
| 2006/0121016 A1 | 6/2006 | Lee |
| 2006/0121610 A1 | 6/2006 | Rubinsky et al. |
| 2006/0135998 A1 | 6/2006 | Libbus et al. |
| 2006/0136004 A1 | 6/2006 | Cowan et al. |
| 2006/0149350 A1 | 7/2006 | Patel et al. |
| 2006/0155344 A1 | 7/2006 | Rezai et al. |
| 2006/0167437 A1 | 7/2006 | Valencia |
| 2006/0167498 A1 | 7/2006 | DiLorenzo |
| 2006/0167499 A1 | 7/2006 | Palti |
| 2006/0189941 A1 | 8/2006 | Seward et al. |
| 2006/0189960 A1 | 8/2006 | Kesten et al. |
| 2006/0190044 A1 | 8/2006 | Libbus et al. |
| 2006/0206149 A1 | 9/2006 | Yun |
| 2006/0206150 A1 | 9/2006 | Demarais et al. |
| 2006/0212076 A1 | 9/2006 | Demarais et al. |
| 2006/0212078 A1 | 9/2006 | Demarais et al. |
| 2006/0229677 A1 | 10/2006 | Moffitt et al. |
| 2006/0235474 A1 | 10/2006 | Demarais |
| 2006/0265014 A1 | 11/2006 | Demarais et al. |
| 2006/0265015 A1 | 11/2006 | Demarais et al. |
| 2006/0271111 A1 | 11/2006 | Demarais et al. |
| 2006/0276852 A1 | 12/2006 | Demarais et al. |
| 2007/0066957 A1 | 3/2007 | Demarais et al. |
| 2007/0066972 A1 | 3/2007 | Ormsby et al. |
| 2007/0083239 A1 | 4/2007 | Demarais et al. |
| 2007/0129720 A1 | 6/2007 | Demarais et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0142864 A1 | 6/2007 | Libbus et al. |
| 2007/0156200 A1 | 7/2007 | Kornet et al. |
| 2007/0173899 A1 | 7/2007 | Levin et al. |
| 2007/0208382 A1 | 9/2007 | Yun |
| 2007/0265687 A1 | 11/2007 | Deem et al. |
| 2007/0282376 A1 | 12/2007 | Shuros et al. |
| 2007/0288070 A1 | 12/2007 | Libbus et al. |

(56) References Cited

U.S. PATENT DOCUMENTS

| | | |
|---|---|---|
| 2008/0004673 A1 | 1/2008 | Rossing et al. |
| 2008/0015659 A1 | 1/2008 | Zhang et al. |
| 2008/0039904 A1 | 2/2008 | Bulkes et al. |
| 2008/0091255 A1 | 4/2008 | Caparso et al. |
| 2008/0140150 A1 | 6/2008 | Zhou et al. |
| 2008/0172104 A1 | 7/2008 | Kieval et al. |
| 2008/0213331 A1 | 9/2008 | Gelfand et al. |
| 2008/0255642 A1 | 10/2008 | Zarins et al. |
| 2008/0319513 A1 | 12/2008 | Pu et al. |
| 2009/0024195 A1 | 1/2009 | Rezai et al. |
| 2009/0036948 A1 | 2/2009 | Levin et al. |
| 2009/0062873 A1 | 3/2009 | Wu et al. |
| 2009/0076409 A1 | 3/2009 | Wu et al. |
| 2009/0099564 A1 | 4/2009 | Koblish et al. |
| 2010/0010567 A1 | 1/2010 | Deem et al. |
| 2010/0057150 A1 | 3/2010 | Demarais et al. |
| 2010/0137860 A1 | 6/2010 | Demarais et al. |
| 2010/0137952 A1 | 6/2010 | Demarais et al. |
| 2010/0168731 A1 | 7/2010 | Wu et al. |
| 2010/0168739 A1 | 7/2010 | Wu et al. |
| 2010/0174282 A1 | 7/2010 | Demarais et al. |
| 2010/0191112 A1 | 7/2010 | Demarais et al. |
| 2010/0222851 A1 | 9/2010 | Deem et al. |
| 2010/0222854 A1 | 9/2010 | Demarais et al. |
| 2010/0249773 A1 | 9/2010 | Clark et al. |
| 2010/0268307 A1 | 10/2010 | Demarais et al. |
| 2011/0060324 A1 | 3/2011 | Wu et al. |
| 2011/0086257 A1 | 4/2011 | Pitteloud et al. |
| 2011/0112400 A1 | 5/2011 | Emery et al. |
| 2011/0137298 A1 | 6/2011 | Nguyen et al. |
| 2011/0200171 A1 | 8/2011 | Beetel et al. |
| 2011/0202098 A1 | 8/2011 | Demarais et al. |
| 2011/0257564 A1 | 10/2011 | Demarais et al. |
| 2011/0264011 A1 | 10/2011 | Wu et al. |
| 2011/0264075 A1 | 10/2011 | Leung et al. |
| 2013/0172880 A1 | 7/2013 | Willard |
| 2013/0296853 A1 | 11/2013 | Sugimoto et al. |
| 2014/0121641 A1 | 5/2014 | Fischell et al. |
| 2014/0121644 A1 | 5/2014 | Fischell et al. |
| 2014/0135661 A1 | 5/2014 | Garrison et al. |
| 2014/0276621 A1 | 9/2014 | Braga |
| 2014/0316351 A1 | 10/2014 | Fischell et al. |
| 2014/0378906 A1 | 12/2014 | Fischell et al. |
| 2015/0005719 A1 | 1/2015 | Fischell et al. |

FOREIGN PATENT DOCUMENTS

| | | |
|---|---|---|
| EP | 2092957 | 8/2009 |
| EP | 2656807 | 10/2013 |
| EP | 2744561 | 6/2014 |
| EP | 2747688 | 7/2014 |
| WO | WO-1985001213 | 3/1985 |
| WO | WO-1991004725 | 4/1991 |
| WO | WO-1992020291 | 11/1992 |
| WO | WO-1993002740 | 2/1993 |
| WO | WO-1993007803 | 4/1993 |
| WO | WO-1994000188 | 1/1994 |
| WO | WO-1994007446 | 4/1994 |
| WO | WO-1994011057 | 5/1994 |
| WO | WO-1995025472 | 9/1995 |
| WO | WO-1995031142 | 11/1995 |
| WO | WO-1995033514 | 12/1995 |
| WO | WO-1996000039 | 1/1996 |
| WO | WO-1996004957 | 2/1996 |
| WO | WO-1996011723 | 4/1996 |
| WO | WO-1997013463 | 4/1997 |
| WO | WO-1997013550 | 4/1997 |
| WO | WO-1997036548 | 10/1997 |
| WO | WO1997045157 | 12/1997 |
| WO | WO-1997049453 | 12/1997 |
| WO | WO-1998037926 | 9/1998 |
| WO | WO-1998042403 | 10/1998 |
| WO | WO-1998043700 | 10/1998 |
| WO | WO-1998043701 | 10/1998 |
| WO | WO-1998048888 | 11/1998 |
| WO | WO-1999000060 | 1/1999 |
| WO | WO1999000060 | 1/1999 |
| WO | WO-1999033407 | 7/1999 |
| WO | WO-1999051286 | 10/1999 |
| WO | WO-1999052424 | 10/1999 |
| WO | WO-2001022897 | 4/2001 |
| WO | WO-2001026729 | 4/2001 |
| WO | WO-2001070114 | 9/2001 |
| WO | WO-2002009808 | 2/2002 |
| WO | WO-2002026314 | 4/2002 |
| WO | WO2002053207 | 7/2002 |
| WO | WO-2002070039 | 9/2002 |
| WO | WO-2002070047 | 9/2002 |
| WO | WO-2002085192 | 10/2002 |
| WO | WO-2002085448 | 10/2002 |
| WO | WO-2003018108 | 3/2003 |
| WO | WO-2003022167 | 3/2003 |
| WO | WO-2003028802 | 4/2003 |
| WO | WO-2003063692 | 8/2003 |
| WO | WO-2003071140 | 8/2003 |
| WO | WO-2003076008 | 9/2003 |
| WO | WO-2003082080 | 10/2003 |
| WO | WO-2003082403 | 10/2003 |
| WO | WO-2004026370 | 4/2004 |
| WO | WO-2004026371 | 4/2004 |
| WO | WO-2004026374 | 4/2004 |
| WO | WO-2004030718 | 4/2004 |
| WO | WO-2004032791 | 4/2004 |
| WO | WO-2004107965 | 12/2004 |
| WO | WO-2005014100 | 2/2005 |
| WO | WO-2005016165 | 2/2005 |
| WO | WO-2005030072 | 4/2005 |
| WO | WO-2005032646 | 4/2005 |
| WO | WO-2005041748 | 5/2005 |
| WO | WO2005065284 | 7/2005 |
| WO | WO-2005084389 | 9/2005 |
| WO | WO-2005097256 | 10/2005 |
| WO | WO-2005110528 | 11/2005 |
| WO | WO-2005123183 | 12/2005 |
| WO | WO-2006007048 | 1/2006 |
| WO | WO-2006018528 | 2/2006 |
| WO | WO-2006022790 | 3/2006 |
| WO | WO-2006031899 | 3/2006 |
| WO | WO2006041847 | 4/2006 |
| WO | WO-2006041881 | 4/2006 |
| WO | WO-2006105121 | 10/2006 |
| WO | WO-2007008954 | 1/2007 |
| WO | WO-2007035537 | 3/2007 |
| WO | WO-2007078779 | 7/2007 |
| WO | WO-2007078997 | 7/2007 |
| WO | WO2007078997 | 7/2007 |
| WO | WO2007086965 | 8/2007 |
| WO | WO-2007103879 | 9/2007 |
| WO | WO-2007103881 | 9/2007 |
| WO | WO-2007121309 | 10/2007 |
| WO | WO-2007146834 | 12/2007 |
| WO | WO-2008003058 | 1/2008 |
| WO | WO-2008049084 | 4/2008 |
| WO | WO-2008061150 | 5/2008 |
| WO | WO-2008061152 | 5/2008 |
| WO | WO-2008070413 | 6/2008 |
| WO | WO-2010078175 | 7/2010 |
| WO | WO2014070999 | 5/2014 |

OTHER PUBLICATIONS

"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.

"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europcr-innovation-award-and-demonstrates-further-durability-of-renal-denervation-treatment-for-hypertension-95545014.html>.

(56) References Cited

OTHER PUBLICATIONS

"Boston Scientific to Acquire Vessix Vascular, Inc.: Company to Strengthen Hypertension Program with Acquisition of Renal Denervation Technology." Boston Scientific: Advancing science for life-Investor Relations, Nov. 8, 2012, 2 pages, <http://phx.corporate-ir.net/phoenix.zhtml?c=62272&p=irol-newsArticle&id=1756108>.
"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.
"Does renal denervation represent a new treatment option for resistant hypertension?" Interventional News, Aug. 3, 2010, 2 pages. <http://www.cxvascular.com/in-latest-news/interventional-news--latest-news/does-renal-denervation-represent-a-new-treatment-option-for-resistant-hypertension>.
"Iberis—Renal Sympathetic Denervation System: Turning innovation into quality care." [Brochure], Terumo Europe N.V., 2013, Europe, 3 pages.
"Neurotech Reports Announces Winners of Gold Electrode Awards." Neurotech business report, 2009. 1 page. <http://www.neurotechreports.com/pages/goldelectrodes09.html>.
"Quick. Consistent. Controlled. OneShot renal Denervation System" [Brochure], Covidien: positive results for life, 2013, (n.l.), 4 pages
"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison AwardsTM" Edison Awards: Honoring Innovations & Innovators, 2013, 2 pages, <http://www.edisonawards.com/Awards.php>.
"The Future of Renal denervation for the Treatment of Resistant Hypertension." St. Jude Medical, Inc., 2012, 12 pages.
"Vessix Renal Denervation System: So Advanced It's Simple." [Brochure], Boston Scientific: Advancing science for life, 2013, 6 pages.
Asbell, Penny, "Conductive Keratoplasty for the Correction of Hyperopia." Tr Am Ophth Soc, 2001, vol. 99, 10 pages.
Badoer, Emilio, "Cardiac afferents play the dominant role in renal nerve inhibition elicited by volume expansion in the rabbit." Am J Physiol Regul lntegr Comp Physiol, vol. 274, 1998, 7 pages.
Bengel, Frank, "Serial Assessment of Sympathetic Reinnervation After Orthotopic Heart Transplantation: A longitudinal Study Using PET and C-11 Hydroxyephedrine." Circulation, vol. 99, 1999,7 pages.
Benito, F., et al. "Radiofrequency catheter ablation of accessory pathways in infants." Heart, 78:160-162 (1997).
Bettmann, Michael, Carotid Stenting and Angioplasty: a Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.
Bohm, Michael et al., "Rationale and design of a large registry on renal denervation: the Global Symplicity registry." EuroIntervention, vol. 9, 2013, 9 pages.
Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.
Davis, Mark et al., "Effectiveness of Renal Denervation Therapy for Resistant Hypertension." Journal of the American College of Cardiology, vol. 62, No. 3, 2013, 11 pages.
Dibona, G.F. "Sympathetic nervous system and kidney in hypertension." Nephrol and Hypertension, 11: 197-200 (2002).
Dibona, G.F., et al. "Neural control of renal function." Physiol Rev, 77:75-197 (1997).
Dubuc, M., et al., "Feasibility of cardiac cryoablation using a transvenous steerable electrode catheter." J Interv Cardiac Electrophysiol, 2:285-292 (1998).
Final Office Action; U.S. Appl. No. 12/827,700; dated Feb. 5, 2013, 61 pages.
Geisler, Benjamin et al., "Cost-Effectiveness and Clinical Effectiveness of Catheter-Based Renal Denervation for Resistant Hypertension." Journal of the American College of Cardiology, col. 60, No. 14, 2012, 7 pages.
Gelfand, M., et al., "Treatment of renal failure and hypertension." U.S. Appl. No. 60/442,970, filed Jan. 29, 2003, 23 pages.
Gertner, Jon, "Meet the Tech Duo That's Revitalizing the Medical Device Industry." FAST Company, Apr. 15, 2013, 6:00 AM, 17 pages, <http://www.fastcompany.com/3007845/meet-tech-duo-thats-revitalizing-medical-device-industry>.
Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).
Hall, W. H., et al. "Combined embolization and percutaneous radiofrequency ablation of a solid renal tumor." *Am. J. Roentgenol*,174: 1592-1594 (2000).
Han, Y.-M, et al., "Renal artery embolization with diluted hot contrast medium: An experimental study." J Vasc Interv Radiol, 12: 862-868 (2001).
Hansen, J. M., et al. "The transplanted human kidney does not achieve functional reinnervation." *Clin. Sci*, 87: 13-19 (1994).
Hendee, W. R. et al. "Use of Animals in Biomedical Research: The Challenge and Response." *American Medical Association White Paper* (1988) 39 pages.
Hering, Dagmara et al., "Chronic kidney disease: role of sympathetic nervous system activation and potential benefits of renal denervation." EuroIntervention, vol. 9, 2013, 9 pages.
Imimdtanz, "Medtronic awarded industry's highest honour for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.
Kaiser, Chris, AHA Lists Year's Big Advances in CV Research, medpage Today, Dec. 18, 2012, 4 pages, <http://www.medpagetoday.com/Cardiology/PCI/36509>.
Kompanowska, E., et al., "Early Effects of renal denervation in the anaesthetised rat: Natriuresis and increased cortical blood flow." J Physiol, 531. 2:527-534 (2001).
Lee, S.J., et al. "Ultrasonic energy in endoscopic surgery." Yonsei Med J, 40:545-549 (1999).
Linz, Dominik et al., "Renal denervation suppresses ventricular arrhythmias during acute ventricular ischemia in pigs." Heart Rhythm, vol. 0, No. 0, 2013, 6 pages.
Lustgarten, D.L.,et al., "Cryothermal ablation: Mechanism of tissue injury and current experience in the treatment of tachyarrhythmias." Progr Cardiovasc Dis, 41:481-498 (1999).
Mabin, Tom et al., "First experience with endovascular ultrasound renal denervation for the treatment of resistant hypertension." EuroIntervention, vol. 8, 2012, 5 pages.
Mahfoud, Felix et al., "Ambulatory Blood Pressure Changes after Renal Sympathetic Denervation in Patients with Resistant Hypertension." Circulation, 2013, 25 pages.
Mahfoud, Felix et al., "Expert consensus document from the European Society of Cardiology on catheter-based renal denervation." European Heart Journal, 2013, 9 pages.
Mahfoud, Felix et al., "Renal Hemodynamics and Renal Function After Catheter-Based Renal Sympathetic Denervation in Patients With Resistant Hypertension." Hypertension, 2012, 6 pages.
Medical-Dictionary.com, Definition of "Animal Model," http://medical-dictionary.com (search "Animal Model"), 2005, 1 page.
Medtronic, Inc., Annual Report (Form 10-K) (Jun. 28, 2011) 44 pages.
Millard, F. C., et al, "Renal Embolization for ablation of function in renal failure and hypertension." Postgraduate Medical Journal, 65, 729-734, (1989).

(56) References Cited

OTHER PUBLICATIONS

Oliveira, V., et al., "Renal denervation normalizes pressure and baroreceptor reflex in high renin hypertension in conscious rats." Hypertension, 19:II-17-II-21 (1992).

Ong, K. L., et al. "Prevalence, Awareness, Treatment, and Control of Hypertension Among United States Adults 1999-2004." Hypertension, 49: 69-75 (2007) (originally published online Dec. 11, 2006).

Ormiston, John et al., "First-in-human use of the OneShotTM renal denervation system from Covidien." EuroIntervention, vol. 8, 2013, 4 pages.

Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.

Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.

Peet, M., "Hypertension and its Surgical Treatment by bilateral supradiaphragmatic splanchnicectomy" Am J Surgery (1948) pp. 48-68.

Renal Denervation (RDN), Symplicity RDN System Common Q&A (2011), 4 pages, http://www.medtronic.com/rdnimediakit/RDN%20FAQ.pdf.

Schauerte, P., et al. "Catheter Ablation of Cardiac Autonomic Nerves for Prevention of Vagal Atrial Fibrillation." Circulation, 102:2774-2780 (2000).

Schlaich, Markus et al., "Renal Denervation in Human Hypertension: Mechanisms, Current Findings, and Future Prospects." Curr Hypertens Rep, vol. 14, 2012, 7 pages.

Schmid, Axel et al., "Does Renal Artery Supply Indicate Treatment Success of Renal Denervation." Cardiovasc Intervent Radiol, vol. 36, 2013, 5 pages.

Schmieder, Roland E. et al., "Updated ESH position paper on interventional therapy of resistant hypertension." EuroIntervention, vol. 9, 2013, 9 pages.

Sievert, Horst, "Novelty Award EuroPCR 2010." Euro PCR, 2010, 15 pages.

Stella, A., et al., "Effects of reversable renal denervation on haemodynamic and excretory functions on the ipsilateral and contralateral kidney in the cat." Hypertension, 4: 181-188 (1986).

Stouffer, G. A. et al., "Catheter-based renal denervation in the treatment of resistant hypertension." Journal of Molecular and Cellular Cardiology, vol. 62, 2013, 6 pages.

Swartz, J.F., et al., "Radiofrequency endocardial catheter ablation of accessory atrioventricular pathway atrial insertion sites." Circulation, 87: 487-499 (1993).

Uchida, F., et al., "Effect of radiofrequency catheter ablation on parasympathetic denervation: A comparison of three different ablation sites." PACE, 21:2517-2521 (1998).

Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.

Weinstock, M., et al., "Renal denervation prevents sodium retention and hypertension in salt sensitive rabbits with genetic baroreflex impairment." Clinical Science, 90:287-293 (1996).

Doumas, Michael et al., "Renal Nerve Ablation for Resistant Hypertension: The Dust Has Not Yet Settled." The Journal of Clinical Hypertension. 2014; vol. 16, No. 6, 2 pages.

Messerli, Franz H. et al. "Renal Denervation for Resistant Hypertension: Dead or Alive?" Healio: Cardiology today's Intervention, May/Jun. 2014, 2 pages.

Miller, Reed, "Finding a Future for Renal Denervation With Better Controlled Trials." Pharma & Medtech Business Intelligence, Article # 01141006003, Oct. 6, 2014, 4 pages.

Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.

Papademetriou, Vasilios et al., "Renal Nerve Ablation for Resistant Hypertension: How Did We Get Here, Present Status, and Future Directions." Circulation. 2014; 129: 1440-1450.

Papademetriou, Vasilios, "Renal Denervation and Symplicity HTN-3: "Dubium Sapientiae Initium" (Doubt Is the Beginning of Wisdom)", Circulation Research, 2014; 115: 211-214.

Wilcox, Josiah N., Scientific Basis Behind Renal Denervation for the Control of Hypertension, ICI 2012, Dec. 5-6, 2012. 38 pages.

Worthley, Stephen et al., "Safety and efficacy of a multi-electrode renal sympathetic denervation system in resistant hypertension: the EnligHTN I trial." European Heart Journal, vol. 34, 2013, 9 pages.

Worthley, Stephen, "The St. Jude Renal Denervation System Technology and Clinical Review." The University of Adelaide Australia, 2012, 24 pages.

Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.

Demarais et al., Reexamination Application 95/002,253 U.S. Pat. No. 8,131,371 filed Sep. 13, 2012.

Demarais et al., Reexamination Application 95/002,255 U.S. Pat. No. 7,617,005 filed Sep. 13, 2012.

Demarais et al., Reexamination Application 95/002,292 U.S. Pat. No. 8,175,711 filed Sep. 14, 2012.

Demarais et al., Reexamination Application 95/002,335 U.S. Pat. No. 8,150,520 filed Sep. 14, 2012.

Demarais et al., Reexamination Application 95/002,356 U.S. Pat. No. 8,150,519 filed Sep. 14, 2012.

Demarias et al., Reexamination Application 95/002,327 U.S. Pat. No. 8,145,317 filed Sep. 14, 2012.

Levin et al. Reexamination Application 95/002,209 U.S. Pat. No. 8,150,518 filed Sep. 13, 2012.

Levin et al., Reexamination Application 95/002,233 U.S. Pat. No. 8,131,372 filed Sep. 13, 2012.

Levin et al., Reexamination Application 95/002,243 U.S. Pat. No. 7,162,303 filed Sep. 13, 2012.

Levin et al., Reexamination Application 95/002,336 U.S. Pat. No. 7,647,115 filed Sep. 14, 2012.

2003 European Society of Hypertension—European Society of Cardiology guidelines for the management of arterial hypertension, Guidelines Committee, Journal of Hypertension 2003, vol. 21, No. 6, pp. 1011-1053.

Aars, H. and S. Akre, Reflex Changes in Sympathetic Activity and Arterial Blood Pressure Evoked by Afferent Stimulation of the Renal Nerve, Feb. 26, 1999, Acta physiol. Scand., vol. 78, 1970, pp. 184-188.

Yu, Wen-Chung et al. Acquired Pulmonary Vein Stenosis after Radiofrequency Catheter Ablation of Paroxysmal Atrial Fibrillation. Journal of Cardiovascular Electrophysiology. vol. 12, No. 8. Aug. 2001, pp. 887-892.

Zanchetti, A. et al., Neural Control of the Kidney—Are There Reno-Renal Reflexes?, Clin. and Exper. Hyper. Theory and Practice, A6 (1&2), 1984, Marcel Dekker, Inc. 1984, pp. 275-286.

Zanchetti, A. et al., Practice Guidelines for Primary Care Physicians: 2003 ESH/ESC Hypertension Guidelines, Journal of Hypertension, vol. 21, No. 10, 2003, pp. 1779-1786.

Zanchetti, A. S., Neural regulation of renin release: Experimental evidence and clinical implications in arterial hypertension, Circulation, 1977, 56(5) 691-698.

Zimmermann, Ulrich, Electrical Breakdown, Electropermeabilization and Electrofusion, Rev. Physiol. Biochem. Pharmacol., vol. 105, Springer-Verlag 1986, pp. 175-256.

Zoccali, C. et al., Plasma norepinephrine predicts survival and incident cardiovascular events in patients with end-stage renal disease. Circulation. 2002;105:1354-9.

Zucker, Irving H. et al., The origin of sympathetic outflow in heart failure: the roles of angiotensin II and nitric oxide, Progress in Biophysics & Molecular Biology, vol. 84, 2004, Elsevier Ltd. 2003, pp. 217-232.

Zundert, Jan Van, M.D. Fipp and Alex Cahana, M.D. Daapm, Pulsed Radiofrequency in Chronic Pain Management: Looking for the Best Use of Electrical Current, Pain Practice 2005, vol. 5, Issue 2, 2005 World Institute of Pain, pp. 74-76.

(56) References Cited

OTHER PUBLICATIONS

Abramov, G.S. et al., Alteration in sensory nerve function following electrical shock, Burns vol. 22, No. 8, 1996 Elsevier Science Ltd., pp. 602-606.
Achar, Suraj, M.D., and Suriti Kundu, M.D., Principles of Office Anesthesia: Part I. Infiltrative Anesthesia, Office Procedures, American Family Physician, Jul. 1, 2002, vol. 66, No. 1, pp. 91-94.
Advanced Neuromodulation Systems' Comparison Chart, Dec. 16, 2008, pp. 1.
Advances in the role of the sympathetic nervous system in cardiovascular medicine, 2001 SNS Report, No. 3, Springer, Published with an educational grant from Servier, pp. 1-8.
Aggarwal, A. et al., Regional sympathetic effects of low-dose clonidine in heart failure. Hypertension. 2003;41:553-7.
Agnew, William F. et al., Evolution and Resolution of Stimulation-Induced Axonal Injury in Peripheral Nerve, May 21, 1999, Muscle & Nerve, vol. 22, Oct. 1999, John Wiley & Sons, Inc. 1999, pp. 1393-1402.
Ahadian, Farshad M., M.D., Pulsed Radiofrequency Neurotomy: Advances in Pain Medicine, Current Pain and Headache Reports 2004, vol. 8, 2004 Current Science Inc., pp. 34-40.
Alexander, B.T. et al., Renal denervation abolishes hypertension in low-birth-weight offspring from pregnant rats with reduced uterine perfusion, Hypertension, 2005; 45 (part 2): pp. 754-758.
Alford, J. Winslow, M.D. and Paul D. Fadale, M.D., Evaluation of Postoperative Bupivacaine Infusion for Pain Management After Anterior Cruciate Ligament Reconstruction, The Journal of Arthroscopic and Related Surgery, vol. 19, No. 8, Oct. 2003 Arthroscopy Association of North America, pp. 855-861.
Allen, E.V., Sympathectomy for essential hypertension, Circulation, 1952, 6:131-140.
Amersham Health. Hypaque-Cysto, 2003, 6 pages.
Andrews, B.T. et al., The use of surgical sympathectomy in the treatment of chronic renal pain. Br J Urol. 1997; 80: 6-10.
Antman, Elliott M. and Eugene Braunwald, Chapter 37—Acute Myocardial Infarction, Heart Disease—A Textbook of Cardiovascular Medicine, 5th Edition, vol. 2, 1997, Edited by Eugene Braunwald, pp. 1184-1288.
Archer, Steffen et al., Cell Reactions to Dielectrophoretic Manipulation, Mar. 1, 1999, Biochemical and Biophysical Research Communications, 1999 Academic Press, pp. 687-698.
Arentz, T. et al., Incidence of pulmonary vein stenosis 2 years after radiofrequency catheter ablation of refractory atrial fibrillation. European Heart Journal. 2003. 24; pp. 963-969.
Arias, M.D., Manuel J., Percutaneous Radio-Frequency Thermocoagulation with Low Temperature in the Treatment of Essential Glossopharyngeal Neuralgia, Surg. Neurol. 1986, vol. 25, 1986 Elsevier Science Publishing Co., Inc., pp. 94-96.
Aronofsky, David H., D.D.S., Reduction of dental postsurgical symptoms using nonthermal pulsed high-peak-power electromagnetic energy, Oral Surg., Nov. 1971, vol. 32, No. 5, pp. 688-696.
Aspelin, Peter, M.D., Ph.D. et al., Nephrotoxic Effects in High-Risk Patients Undergoing Angiography, Feb. 6, 2003, New England Journal of Medicine 2003, vol. 348, No. 6, 2003 Massachusetts Medical Society, pp. 491-499.
Atrial Fibrillation Heart and Vascular Health on Yahoo! Health. 2 pgs. <URL: http://health.yahoo.com/topic/heart/overview/article/healthwise/hw160872;_ylt=AiBT43Ey74HQ7ft3jAb4C.sPu7cF> Feb. 21, 2006.
Augustyniak, Robert A. et al., Sympathetic Overactivity as a Cause of Hypertension in Chronic Renal Failure, Aug. 14, 2001, Journal of Hypertension 2002, vol. 20, 2002 Lippincott Williams & Wilkins, pp. 3-9.
Awwad, Ziad M., FRCS and Bashir A. Atiyat, GBA, JBA, Pain relief using continuous bupivacaine infusion in the paravertebral space after loin incision, May 15, 2004, Saudi Med J 2004, vol. 25 (10), pp. 1369-1373.
Badyal, D. K., H. Lata and A.P. Dadhich, Animal Models of Hypertension and Effect of Drugs, Aug. 19, 2003, Indian Journal of Pharmacology 2003, vol. 35, pp. 349-362.
Baker, Carol E. et al., Effect of pH of Bupivacaine on Duration of Repeated Sciatic Nerve Blocks in the Albino Rat, Anesth Analg, 1991, vol. 72, The International Anesthesia Research Society 1991, pp. 773-778.
Balazs, Tibor, Development of Tissue Resistance to Toxic Effects of Chemicals, Jan. 26, 1974, Toxicology, 2 (1974), Elsevier/North-Holland, Amsterdam, pp. 247-255.
Barajas, L. Innervation of the renal cortex. Fex Proc. 1978;37:1192-201.
Barrett, Carolyn J. et al., Long-term control of renal blood flow: what is the role of the renal nerves?, Jan. 4, 2001, Am J Physiol Regulatory Integrative Comp Physiol 280, 2001, the American Physiological Society 2001, pp. R1534-R1545.
Barrett, Carolyn J. et al., What Sets the Long-Term Level of Renal Sympathetic Nerve Activity, May 12, 2003, Integrative Physiology, Circ Res. 2003, vol. 92, 2003 American Heart Association, pp. 1330-1336.
Bassett, C. Andrew L. et al., Augmentation of Bone Repair by Inductively Coupled Electromagnetic Fields, May 3, 1974, Science, vol. 184, pp. 575-577.
Bassett, C. Andrew L., Fundamental and Practical Aspects of Therapeutic Uses of Pulsed Electromagnetic Fields (PEMFs), Critical Reviews in Biomedical Engineering, vol. 17, Issue 5, 1989, pp. 451-514.
Beebe, Stephen J. et al., Nanosecond pulsed electric fields modulate cell function through intracellular signal transduction mechanisms, Apr. 8, 2004, Physiol. Meas. 25, 2004, IOP Publishing Ltd. 2004, pp. 1077-1093.
Beebe, Stephen J., et al., Nanosecond Pulsed Electric Field (nsPEF) Effects on Cells and Tissues: Apoptosis Induction and Tumor Growth Inhibition, Oct. 11, 2001, IEEE Transactions on Plasma Science, vol. 30, No. 1, Feb. 2002, IEEE 2002, pp. 286-292.
Bello-Reuss, E. et al., Acute unilateral renal denervation in rats with extracellular volume expansion, Departments of Medicine and Physiology, University of North Carolina School of Medicine. F26-F32 Jul. 1975.
Bello-Reuss, E. et al., Effect of renal sympathetic nerve stimulation on proximal water and sodium reabsorption, J Clin Invest, 1976;57:1104-1107.
Bello-Reuss, E. et al., Effects of Acute Unilateral Renal Denervation in the Rat, J Clin Invest, 1975;56:208-217.
Berde, C. et al., Local Anesthetics, Anesthesia, Chapter 13, 5th addition, Churchill-Livingston, Philadelphia 2000, pp. 491-521.
Bhadra, Niloy and Kevin L. Kilgore, Direct Current Electrical Conduction Block of Peripheral Nerve, Feb. 25, 2004, IEEE Transactions on Neural Systems and Rehabilitation Engineering, vol. 12, No. 3, Sep. 2004, pp. 313-324.
Bhandari, A. and Ellias, M., Loin pain hematuria syndrome: Pain control with RFA to the Splanchanic plexus, The Pain Clinic, 2000, vol. 12, No. 4, pp. 323-327.
Bhatt, Deepak L. et al., Rhabdomyolysis Due to Pulsed Electric Fields, May 11, 1989, Plastic and Reconstructive Surgery Jul. 1990, pp. 1-11.
Bichet, D., et al., Renal intracortical blood flow and renin secretion after denervation by 6-hydroxydopamine. Can J Physiol Pharmacol. 1982;60:184-92.
Bigler, D. et al., Tachyphylaxis during postoperative epidural analgesia—new insights, Apr. 15, 1987, Letter to the Editor, Acta Anaesthesiol Scand. 1987, vol. 31, pp. 664-665.
Binder, Allan et al., Pulsed Electromagnetic Field Therapy of Persistent Rotator Cuff Tendinitis, The Lancet, Saturday Mar. 31, 1984, The Lancet Ltd., pp. 695-698.
Black, M.D., Henry R., Resistant Hypertension 2004, presentation at Rush University Medical Center, Jul. 15, 2004, 40 pages.
Blad, B., et al., An Electrical Impedance index to Assess Electroporation in Tissue, Tissue and Organ (Therapy), 2001, Oslo, www.bl.uk <http://www.bl.uk> British Library, pp. 31-34.
Blair, M. L. et al, Sympathetic activation cannot fully account for increased plasma renin levels during water deprivation, Sep. 23, 1996, Am. J. Physiol., vol. 272, 1997, the American Physiological Society 1997, pp. R1197-R1203.

(56) References Cited

OTHER PUBLICATIONS

Blomberg, S.G., M.D., PhD, Long-Term Home Self-Treatment with High Thoracic Epidural Anesthesia in Patients with Severe Coronary Artery Disease, Mar. 29, 1994, Anesth Analg 1994, vol. 79, 1994 International Anesthesia Research Society, pp. 413-421.
Boehmer, J.P., Resynchronization Therapy for Chronic CHF: Indications, Devices and Outcomes. Penn State College of Medicine: Penn State Heart and Vascular Institute. Transcatheter Cardiovascular Therapeutics 2005, 31 slides.
Bourge, R.C., Heart Failure Monitoring Devices: Rationale and Status 28 pages, Feb. 2001.
Braunwald, E., Heart Disease, A Textbook of Cardiovascular Medicine, 5th Ed., vol. 2, 1997, pp. 480-481, 824-825, 1184-1288 and 1923-1925, W.B. Saunders Company.
Bravo, E.L., et al., Renal denervation for resistant hypertension, American Journal of Kidney Diseases, 2009, 3 pgs.
Bunch, Jared T. et al. Mechanisms of Phrenic Nerve Injury During Radiofrequency Ablation at the Pulmonary Vein Orifice. Journal of Cardiovascular Electrophysiclody. vol. 16, No. 12. pp. 1318-1325. Dec. 2005.
Burkhoff, D., Interventional Device-Based Therapy for CHF Will Redefine Current Treatment Paradigms. Columbia University. 2004. 32 slides.
Burns, J. et al., Relationship between central sympathetic drive and magnetic resonance imaging-determined left ventricular mass in essential hypertension. Circulation. 2007;115:1999-2005.
Cahana, A. et al., Acute Differential Modulation of Synaptic Transmission and Cell Survival During Exposure to Pulsed and Continuous Radiofrequency Energy, May 2003, The Journal of Pain, vol. 4, No. 4, © 2003 by the American Pain Society, pp. 197-202.
Cahana, Alex, M.D., Pulsed Radiofrequency: A Neurobiologic and Clinical Reality, May 17, 2005, Anesthesiology 2005, vol. 103, No. 6, Dec. 2005, 2005 American Society of Anesthesiologists, Inc. Lippincott Williams & Wilkins, Inc., p. 1311.
Calaresu, F.R. et al., Haemodynamic Responses and Renin Release During Stimulation of Afferent Renal Nerves in the Cat, Aug. 12, 1975, J. Physiol. 1976, vol. 255, pp. 687-700.
Cameron, Tracy. Micromodular Implants to Provide Electrical Stimulation of Paralyzed Muscles and Limbs. IEEE Transactions on Biomedical Engineering, vol. 44, No. 9, Sep. 1997. pp. 781-790.
Campese, V.M. et al., Renal afferent denervation prevents hypertension in rats with chronic renal failure. Hypertension. 1995;25:878-82.
Campese, V.M. et al., Renal Afferent Denervation Prevents the Progression of Renal Disease in the Renal Ablation Model of Chronic Renal Failure in the Rat, Am J Kidney Dis. 1995;26:861-5.
Campese, V.M., A new model of neurogenic hypertension caused by renal injury: pathophysiology and therapeutic implications, Clin Exp Nephrol (2003) 7: 167-171, Japanese Society of Nephrology 2003.
Campese, V.M., Neurogenic factors and hypertension in chronic renal failure, Journal of Nephrology, vol. 10, No. 4, 1997, Societa Italiana di Nefrologia, pp. 184-187.
Campese, V.M., Neurogenic factors and hypertension in renal disease. Kidney Int. 2000;57 Suppl 75:S2-3.
Canbaz, S. et al., Electrophysiological evaluation of phrenic nerve injury during cardiac surgery—a prospective, controlled clinical study. BioMed Central. 5 pgs. 2004.
Cardiac Glycosides, Heart Disease—A Textbook of Cardiovascular Medicine vol. 2, Edited by Eugene Braunwald, 5th Edition, 1997 WB Saunders Company, pp. 480-481.
Carls, G. et al., Electrical and magnetic stimulation of the intercostal nerves: a comparative study, Electromyogr, clin. Neurophysiol. 1997, vol. 37, pp. 509-512.
Carlson, Scott H. and J. Michael Wyss, e-Hypertension—Opening New Vistas, Introductory Commentary, Hypertension 2000, vol. 35, American Heart Association, Inc. 2000, p. 538.
Carson, P., Device-based Treatment for Chronic Heart Failure: Electrical Modulation of Myocardial Contractility. Transcatheter Cardiovascular Therapeutics 2005, 21 slides.

Chang, Donald C., Cell poration and cell fusion using an oscillating electric field, Biophysical Journal, vol. 56, Oct. 1989, Biophysical Society, pp. 641-652.
Chen, S.A. et al., Initiation of atrial fibrillation by ectopic beats originating from the pulmonary veins: electrophysiological characteristics, pharmacological responses, and effects of radiofrequency ablataion, Circulation, 1999, 100:1879-1886.
Chin, J.L. et al., Renal autotransplantation for the loin pain-hematuria syndrome: long term follow up of 26 cases, J Urol, 1998, vol. 160, pp. 1232-1236.
Chiou, C.W. et al., Efferent Vagal Innervation of the Canine Atria and Sinus and Atrioventricular Nodes. Circulation. Jun. 1997. 95(11):2573-2584. Abstract only. 2 pgs.
Chobanian, Aram V. et al., Seventh Report of the Joint National Committee on Prevention, Detection, Evaluation, and Treatment of High Blood Pressure, Nov. 6, 2003, Hypertension 2003, vol. 42, 2003 American Heart Association, Inc., pp. 1206-1252.
Clinical Trials in Hypertension and Renal Diseases, Slide Source, www.hypertensiononline.org, 33 pages Aug. 13, 2001.
Conradi, E. and Ines Helen Pages, Effects of Continous and Pulsed Microwave Irradiation on Distribution of Heat in the Gluteal Region of Minipigs, Scand J Rehab Med, vol. 21, 1989, pp. 59-62.
Converse, R.L., Jr. et al., Sympathetic Overactivity in Patients with Chronic Renal Failure, N Engl J Med. Dec. 31, 1992, vol. 327 (27), pp. 1912-1918.
Cosman, E.R., Jr. et al., Electric and Thermal Field Effects in Tissue Around Radiofrequency Electrodes, Pain Medicine, vol. 6, No. 6, 2005, American Academy of Pain Medicine, pp. 405-424.
Cosman, E.R., Ph.D., A Comment on the History of the Pulsed Radiofrequency Technique for Pain Therapy, Anesthesiology Dec. 2005, vol. 103, No. 6, 2005 American Society of Anesthesiologists, Inc. Lippincott Williams & Wilkins, Inc., p. 1312.
Crawford, William H. et al., Pulsed Radio Frequency Therapy of Experimentally Induced Arthritis in Ponies, Dec. 18, 1989, Can. J. Vet. Res. 1991, vol. 55, pp. 76-85.
Curtis, J.J. et al., Surgical therapy for persistent hypertension after renal transplantation, Transplantation, 1981, 31(2):125-128.
Dahm, Peter et al., Efficacy and Technical Complications of Long-Term Continuous Intraspinal Infusions of Opioid and/or Bupivacaine in Refractory Nonmalignant Pain . . . , Oct. 6, 1997, The Clinical Journal of Pain, vol. 14, No. 1, 1998, Lippincott-Raven Publishers 1998, pp. 4-16.
Dahm, Peter O. et al., Long-Term Intrathecal Infusion of Opioid and/or Bupivacaine in the Prophylaxis and Treatment of Phantom Limb Pain, Neuromodulation, vol. 1, No. 3, 1998, International Neuromodulation Society 1998, pp. 111-128.
Dang, Nicholas C. et al., A Novel Approach to Increase Total Urine Output in Heart Failure: Renal Nerve Blockade, ACC 2005 poster; 1 page.
Daniel, Alan and Honig, Carl R. Does Histamine Influence Vasodilation Caused by Prolonged Arterial Occlusion or Heavy Exercise? The Journal of Pharmacology and Experimental Therapeutics. vol. 215 No. 2. Aug. 21, 1980. pp. 533-538.
Davalos, R. et al., Electrical Impedance Tomography for Imaging Tissue Electroporation, Jul. 25, 2003, IEEE Transactions on Biomedical Engineering, vol. 51, No. 5, May 2004, IEEE 2004, pp. 761-767.
Davalos, R.V. et al., Tissue Ablation with Irreversible Electroporation, Sep. 7, 2004, Annals of Biomedical Engineering, Feb. 2005, vol. 33, No. 2, 2005 Biomedical Engineering Society, pp. 223-231.
De Leeuw, Peter W. et al., Renal Vascular Tachyphylaxis to Angiotensin II: Specificity of the Response for Angiotensin, Dec. 28, 1981, Life Sciences, vol. 30, 1982 Pergamon Press Ltd., pp. 813-819.
Deng, Jingdong et al., The Effects of Intense Submicrosecond Electrical Pulses on Cells, Nov. 26, 2002, Biophysical Journal, vol. 84, Apr. 2003, Biophysical Society 2003, pp. 2709-2714.
Denton, Kate M. et al., Differential Neural Control of Glomerular Ultrafiltration, Jan. 30, 2004, Proceedings of the Australian Physiological and Pharmacological Society Symposium: Hormonal, Metabolic and Neural Control of the Kidney, Clinical and Experimental Pharmacology and Physiology (2004) 31, pp. 380-386.

(56) References Cited

OTHER PUBLICATIONS

Dev, Nagendu B., Ph.D. et al., Intravascular Electroporation Markedly Attenuates Neointima Formation After Balloon Injury of the Carotid Artery in the Rat, Journal of Interventional Cardiology, vol. 13, No. 5, 2000, pp. 331-338.
Dev, Nagendu B., Ph.D. et al., Sustained Local Delivery of Heparin to the Rabbit Arterial Wall with an Electroporation Catheter, May 5, 1998, Catheterization and Cardiovascular Diagnosis, vol. 45, 1998, Wiley-Liss, Inc. 1998, pp. 337-345.
Devereaux, R.B. et al., Regression of Hypertensive Left Ventricular Hypertrophy by Losartan Compared With Atenolol: The Losartan Intervention for Endpoint Reduction in Hypertension (LIFE) Trial, Circulation, 2004, vol. 110, pp. 1456-1462.
Dibona, Gerald F. and Linda L. Sawin, Role of renal nerves in sodium retention of cirrhosis and congestive heart failure, Sep. 27, 1990, Am. J. Physiol. 1991, vol. 260, 1991 the American Physiological Society, pp. R298-R305.
Dibona, Gerald F. and Susan Y. Jones, Dynamic Analysis of Renal Nerve Activity Responses to Baroreceptor Denervation in Hypertensive Rats, Sep. 19, 2000, Hypertension Apr. 2001, American Heart Association, Inc. 2001, pp. 1153-1163.
Dibona, Gerald F. and Ulla C. Kopp, Neural Control of Renal Function, Physiological Reviews, vol. 77, No. 1, Jan. 1997, the American Physiological Society 1997, pp. 75-197.
Dibona, Gerald F. and Ulla C. Kopp, Role of the Renal Sympathetic Nerves in Pathophysiological States, Neural Control of Renal Function, vol. 77, pp. 142-197 Jan. 1997.
Dibona, Gerald F., Functionally Specific Renal Sympathetic Nerve Fibers: Role in Cardiovascular Regulation, Mar. 6, 2001, American Journal of Hypertension, 2001, vol. 14, 2001 American Journal of Hypertension, Ltd. Published by Elsevier Science Inc., pp. 163S-170S.
Dibona, Gerald F., L.L. Sawin, Effect of renal nerve stimulation on NaCl and H2O transport in Henle's loop of the rat,: 1982, American Physiological Society, F576-F580, 5 pgs.
Dibona, Gerald F., Nervous Kidney—Interaction Between Renal Sympathetic Nerves and the Renin-Angiotensin System in the Control of Renal Function, Jun. 21, 2000, Hypertension 2000, vol. 36, 2000 American Heart Association, Inc., pp. 1083-1088.
Dibona, Gerald F., Neural Control of the Kidney—Past, Present and Future, Nov. 4, 2002, Novartis Lecture, Hypertension 2003, 41 part 2, 2002 American Heart Association, Inc., pp. 621-624.
Dibona, Gerald F., Neural Control of the Kidney: Functionally Specific Renal Sympathetic Nerve Fibers, Starling Lecture, Am J Physiol Regulatory Integrative Comp Physiol, 2000, 279, 2000 The American Physiological Society, pp. R1517-R1524.
Dibona, Gerald F., Peripheral and Central Interactions between the Renin-Angiotensin System and the Renal Sympathetic Nerves in Control of Renal Function, Annals New York Academy of Sciences, pp. 395-406 Jan. 25, 2006.
Dibona, Gerald F., Renal Innervation and Denervation: Lessons from Renal Transplantation Reconsidered, Artificial Organs, vol. 11, No. 6, Raven Press, Ltd., 1987 International Society for Artificial Organs, pp. 457-462.
Dibona, Gerald F., Sympathetic Nervous System and the Kidney in Hypertension, Current Opinion in Nephrology and Hypertension 2002, vol. 11, 2002 Lippincott Williams & Wilkins, pp. 197-200.
Dibona, Gerald F., The Sympathetic Nervous System and Hypertension, Dec. 4, 2003, Hypertension Highlights, Hypertension Feb. 2004, vol. 43, 2004 American Heart Association, Inc., pp. 147-150.
Dibona, Gerald, LL Sawin, Effect of renal denervation on dynamic autoregulation of renal blood flow, Feb. 12, 2004, AmJ Physiol Renal Physiol 286, pp. F1209-F1218.
Dong, Jun et al. Incidence and Predictors of Pulmonary Vein Stenosis Following Catheter Ablation of Atrial Fibrillation Using the Anatomic Pulmonary Vein Ablation Approach: Results from Paired Magnetic Resonance Imaging. Journal of Cardiovascular Electrophysiology. vol. 16, No. 8, Aug. 2005. pp. 845-852.
Dorros, Gerald, M.D., Renal Artery Stenting State of the Art, presentation, TCT, Washington D.C., Sep. 2003, 27 pages.

Dueck, Ron, M.D., Noninvasive Cardiac Output Monitoring, The Cardiopulmonary and Critical Care Journal, Chest, vol. 120, sec. 2, Aug. 2001, American College of Chest Physicians 2005, pp. 339-341, 5 pages.
Dunn, Matthew D. et al., Laparoscopic Nephrectomy in Patients With End-Stage Renal Disease and Autosomal Dominant Polycystic Kidney Disease, Oct. 25, 1999, American Journal of Kidney Diseases, vol. 35, No. 4 (Apr.) 2000, National Kidney Foundation, Inc. 2000, pp. 720-725.
Durand, D.M., Electric Field Effects in Hyperexcitable Neural Tissue: A Review, Radiation Protection Dosimetry, vol. 106, No. 4, 2003 Nuclear Technology Publishing, pp. 325-331.
Effects of Renal Failure on the Cardiovascular System, 5th Edition Heart Disease, A Textbook of Cardiovascular Medicine, vol. 2, Edited by Eugene Braunwald, 1997, W.B. Saunders Company, pp. 1923-1925.
Electrical Stimulation for the Treatment of Chronic Wounds, Radiation Protection Standard, Maximum Exposure Levels to Radiofrequency Fields—3 KHz to 300 GHz, Radiation Protection Series No. 3, Australian Radiation Protection and Nuclear Safety Agency, Apr. 1996, 322 pgs.
Electropermeabilization (Electroporation), Cyto Pulse Sciences, Inc., http://www.cytopulse.com/electroporation.html (last accessed Mar. 3, 2005), 3 pgs.
Electroporation based Technologies and Treatments, ESPE Newsletter No. 6, QLK 02002-2003, Jan. 2005, www.cliniporator.com, 4 pgs.
End-stage renal disease payment policies in traditional Medicare, Chapter 8, Report to the Congress: Medicare Payment Policy, Mar. 2001, Medpac, pp. 123-138.
Epidemiology of Renal Disease in Hypertension, slide presentation by hypertensiononline.org, 21 pages Mar. 30, 2001.
Erdine, Serap and Alev Arat-Ozkan, Resistant Hypertension, European Society of Hypertension Scientific Newsletter: Update on Hypertension Management 2003, vol. 4, No. 15, 2 pages.
Esler, M. et al., Mechanism of elevated plasma noradrenaline in the course of essential hypertension. J Cardiovasc Pharmacol. 1986;8:S39-43.
Esler, M. et al., Noradrenaline release and the pathophysiology of primary human hypertension. Am J Hypertens. 1989; 2:140S-146S.
Esler, M. et al., Sympathetic nerve biology in essential hypertension, Clin and Exp Pharmacology and Physiology, 2001, 28:986-989.
European Examination Report; European Patent Application No. 07799148.7; Applicant: Ardian, Inc.; dated Jan. 19, 2010, 4 pgs.
European Examination Report; European Patent Application No. 09156661.2; Applicant: Ardian, Inc.; dated Jan. 19, 2010, 6 pgs.
European Search Report; European Patent Application No. 05806045.0; Applicant: Ardian, Inc.; dated Sep. 22, 2009, 8 pgs.
European Search Report; European Patent Application No. 05811851.4; Applicant: Ardian, Inc.; dated Oct. 1, 2009, 7 pgs.
European Search Report; European Patent Application No. 06847926.0; Applicant: Ardian, Inc.; dated Feb. 10, 2010, 6 pgs.
European Search Report; European Patent Application No. 07757925.8; Applicant: Ardian, Inc.; dated Apr. 29, 2010, 9 pgs.
European Search Report; European Patent Application No. 07798341.9; Applicant: Ardian, Inc.; dated Aug. 4, 2011; 6 pgs.
European Search Report; European Patent Application No. 07799148.7; Applicant: Ardian, Inc.; dated Jul. 23, 2009, 6 pgs.
European Search Report; European Patent Application No. 07868755.5; Applicant: Ardian, Inc.; dated Jul. 28, 2010, 7 pgs.
European Search Report; European Patent Application No. 09156661.2; Applicant: Ardian, Inc.; dated Jul. 23, 2009, 6 pgs.
European Search Report; European Patent Application No. 09167937.3; Applicant: Ardian, Inc.; dated Nov. 11, 2009, 6 pgs.
European Search Report; European Patent Application No. 09168202.1; Applicant: Ardian, Inc.; dated Nov. 11, 2009, 5 pgs.
European Search Report; European Patent Application No. 09168204.7; Applicant: Ardian, Inc.; dated Nov. 19, 2009, 6 pgs.
Evelyn, K.A. et al., Effect of thoracolumbar sympathectomy on the clinical course of primary (essential) hypertension, Am J Med, 1960;28:188-221.

(56) References Cited

OTHER PUBLICATIONS

Ex parte Quayle Office Action; U.S. Appl. No. 11/144,173; dated May 28, 2009, 4 pgs.
Fact Book Fiscal Year 2003, National Institutes of Health National Heart, Lung, and Blood Institute, Feb. 2004, 197 pgs.
Fajardo, J. et al., Effect of chemical sympathectomy on renal hydroelectrolytic handling in dogs with chronic caval constriction. Clin Physiol Biochem. 1986;4:252-6.
Fareed, Jawed, Ph.D. et al., Some Objective Considerations for the Use of Heparins and Recombinant Hirudin in Percutaneous Transluminal Coronary Angoplasty, Seminars in Thrombosis and Hemostasis 1991, vol. 17, No. 4, 1991 by Thieme Medical Publishers, Inc., pp. 455-470.
Ferguson, D.R. et al., Responses of the pig isolated renal artery to transmural electrical stimulation and drugs, Dec. 7, 1984, Br. J. Pharmac. 1985, vol. 84, The Macmillan Press Ltd. 1985, pp. 879-882.
Fernandez-Ortiz, Antonio, et al., A New Approach for Local Intravascular Drug Delivery—Iontophoretic Balloon, Intravascular Iontophoretic Local Delivery, Circulation, vol. 89, No. 4, Apr. 1994, pp. 1518-1522.
Fields, Larry E. et al., The Burden of Adult Hypertension in the United States 1999 to 2000—A Rising Tide, May 18, 2004, American Heart Association 2004, Hypertension Oct. 2004, pp. 1-7.
Final Office Action; U.S. Appl. No. 11/233,814; dated Jan. 29, 2009, 11 pgs.
Final Office Action; U.S. Appl. No. 11/266,993; dated Jan. 8, 2010, 7 pgs.
Final Office Action; U.S. Appl. No. 11/363,867; dated May 1, 2009, 8 pgs.
Final Office Action; U.S. Appl. No. 11/451,728; dated Jan. 13, 2009, 7 pgs.
Final Office Action; U.S. Appl. No. 11/599,649; dated Jan. 15, 2009, 10 pgs.
Final Office Action; U.S. Appl. No. 11/599,723; dated Apr. 5, 2010, 17 pgs.
Final Office Action; U.S. Appl. No. 11/599,890; dated Apr. 29, 2009, 9 pgs.
Fischell, Tim A. et al., Ultrasonic Energy: Effects on Vascular Function and Integrity, Circulation: Journal of the American Heart Association. 1991. 84;pp. 1783-1795.
Freeman, Scott A. et al., Theory of Electroporation of Planar Bilayer Membranes: Predictions of the Aqueous Area, Change in Capacitance, and Pore-Pore Separation, Feb. 23, 1994, Biophysical Journal, Jul. 1994, vol. 67, 1994 by the Biophysical Society, pp. 42-56.
Fukuoka, Yuko et al., Imaging of neural conduction block by neuromagnetic recording, Oct. 16, 2002, Clinical Neurophysiology, vol. 113, 2002, Elsevier Science Ireland Ltd. 2002, pp. 1985-1992.
Fuster, Valentin et al. ACC/AHA/ESC Practice Guidelines: ACA/AHA/ESC 2006 Guidelines for the Management of Patients with Atrial Fibrillation. JACC vol. 48, No. 4, Aug. 15, 2006.
Gami, Apoor S., M.D. and Vesna D. Garovic, M.D., Contrast Nephropathy After Coronary Angiography, Mayo Clin Proc. 2004, vol. 79, 2004 Mayo Foundation for Medical Education and Research, pp. 211-219.
Gattone II, Vincent H. et al., Contribution of Renal Innervation to Hypertension in Polycystic Kidney Disease in the Rat, University of Chicago Section of Urology, 16 pages, Mar. 17, 2008.
Gaylor, D.C. et al., Significance of Cell Size and Tissue Structure in Electrical Trauma, Jan. 26, 1988, J. theor. Biol. 1988, vol. 133, 1988 Academic Press Limited, pp. 223-237.
Gazdar, A.F. and G.J. Dammin, Neural degeneration and regeneration in human renal transplants, NEJM, Jul. 30, 1970, 283:222-244.
Gehl, Julie et al., In Vivo Electroporation of Skeletal Muscle: Threshold, Efficacy and Relation to Electric Field Distribution, Biochimica et Biophysica Acta, 1428, 1999, Elsevier Science B.V. 1999, pp. 233-240, www.elsevier.com/locate/bba <http:www.elsevier.com/locate/bba>.

Getts, R.T. et al., Regression of left ventricular hypertrophy after bilateral nephrectomy, Nephrol Dial Transplant, 2006, vol. 21, pp. 1089-1091.
Ghoname, El-sayed A. et al., Percutaneous electrical nerve stimulation: an alternative to TENS in the management of sciatica, Apr. 26, 1999, Pain 1999, vol. 83, 1999 International Association for the Study of Pain / Published by Elsevier Science B.V., pp. 193-199.
Gimple, M.D., Lawrence et al., Effect of Chronic Subcutaneous or Intramural Administration of Heparin on Femoral Artery Restenosis After Balloon Angioplasty in Hypercholesterolemic Rabbits, Laboratory Investigation, Circulation, vol. 86, No. 5, Nov. 1992, pp. 1536-1546.
Goldberger, Jeffrey J. et al., New technique for vagal nerve stimulation, Jun. 2, 1999, Journal of Neuroscience Methods 91, 1999, Elsevier Science B.V. 1999, pp. 109-114.
Gorbunov, F.E. et al., The Use of Pulsed and Continuous Short Wave Diathermy (Electric Field) in Medical Rehabilitation of the Patients with Guillan-Barre Syndrome and Other Peripheral Myelinopathies, May 6, 1994, 5 pages (most of article in Russian language).
Gottschalk, C.W., Renal nerves and sodium excretion, Ann. Rev. Physiol., 1979, 41:229-240.
Greenwell, T.J. et al., The outcome of renal denervation for managing loin pain haematuria syndrome. BJU International, 2004; 4 pgs.
Gruberg, Luis, M.D. et al., The Prognostic Implications of Further Renal Function Deterioration Within 48 h of Interventional Coronary Procedures in Patients with Pre-existent Chronic Renal Insufficiency, Jun. 19, 2000, Journal of the American College of Cardiology 2000, vol. 36, No. 5, 2000 by the American College of Cardiology, pp. 1542-1548.
Guimaraes, Sarfim. Vascular Adrenoceptors: An Update. pp. 319-356, Jun. 1, 2001.
Haissaguerre, M. et al., Spontaneous initiation of atrial fibrillation by ectopic beats orginating in the pulmonary veins, New England Journal of Medicine, 1998, 339: 659-666.
Hajjar, Ihab, M.D., M.S. and Theodore A. Kotchen, M.D., Trends in Prevalence, Awareness, Treatment, and Control of Hypertension in the United States, 1988-2000, JAMA, Jul. 9, 2003, vol. 290, No. 2, pp. 199-206.
Hammer, Leah W. Differential Inhibition of Functional Dilation of Small Arterioles by Indomethacin and Glibenclamide. Hypertension. Feb. 2001 Part II. pp. 599-603.
Hampers, C.L. et al., A hemodynamic evaluation of bilateral nephrectomy and hemodialysis in hypertensive man, Circulation. 1967;35:272-288.
Hamza, M.D., Mohamed A. et al., Effect of the Duration of Electrical Stimulation on the Analgesic Response in Patients with Low Back Pain, Anesthesiology, vol. 91, No. 6, Dec. 1999, American Society of Anesthesiologists, Inc. 1999, pp. 1622-1627.
Han, Hyo-Kyung and Gordon L. Amidon, Targeted Prodrug Design to Optimize Drug Delivery, Mar. 21, 2000, AAPS Pharmsci 2000, 2 (1) article 6, pp. 1-11.
Hansen, J. M. et al., The transplanted human kidney does not achieve functional reinnervation, Clin Science, 1994, vol. 87, pp. 13-20.
Hasking, G.J. et al., Norepinephrine spillover to plasma in patients with congestive heart failure: evidence of increased overall and cardiorenal sympathetic nervous activity. Circulation. 1986;73:615-21.
Hausberg, M. et al., Sympathetic nerve activity in end-stage renal disease, Circulation, 2002, 106: 1974-1979.
Heart Arrhythmia Heart and Vascular Health on Yahoo! Health. 13 pgs. <URL: http://health.yahoo.com/topic/heart/overview/article/mayoclinic/21BBE2B0-128D-4AA2-A5CE215065586678;_ylt=Aqd9M5rNyHD0sbPOmHXFhLcPu7cF> Feb. 16, 2005.
Heart Disease and Stroke Statistics—2004 Update, American Heart Association, American Stroke Association, Dallas, Texas, 2003 American Heart Association, 52 pgs.

(56) References Cited

OTHER PUBLICATIONS

Heida, Tjitske, et al., Investigating Membrane Breakdown of Neuronal Cells Exposed to Nonuniform Electric Fields by Finite-Element Modeling and Experiments, May 9, 2002, IEEE Transactions on Biomedical Engineering, vol. 49, No. 10, Oct. 2002, IEEE 2002, pp. 1195-1203.
Heuer, G.J., The surgical treatment of essential hypertension, Annals of Surgery, 1936; 104 (4): 771-786.
Higuchi, Yoshinori, M.D., Ph.D. et al, Exposure of the Dorsal Root Ganglion in Rats to Pulsed Radiofrequency Currents Activates Dorsal Horn Lamina I and II Neurons, Dec. 4, 2001, Experimental Studies, Neurosurgery, vol. 50, No. 4, Apr. 2002, pp. 850-856.
Hildebrand, Keith R., D.V.M., Ph.D. et al., Stability, Compatibility, and Safety of Intrathecal Bupivacaine Administered Chronically via an Implantable Delivery System, May 18, 2001, The Clinical Journal of Pain, vol. 17, No. 3, 2001 Lippincott Williams & Wilkins, Inc., pp. 239-244.
Hing, Esther, M.P.H. and Kimberly Middleton, B.S.N., M.P.H., National Hospital Ambulatory Medical Care Survey: 2001 Outpatient Department Summary, Aug. 5, 2003, Advance Data from Vital and Health Statistics, No. 338, CDC, 32 pages.
Hodgkin, Douglas D. et al., Electrophysiologic Characteristics of a Pulsed Iontophoretic Drug-Delivery System in Coronary Arteries, Journal of Cardiovascular Pharmacology. 29(1):pp. 39-44, Jan. 1997, Abstract, 2 pgs.
Hopp, F.A. et al., Respiratory Responses to Selective Blockade of Carotid Sinus Baroreceptors in the Dog, Jun. 22, 2005, Am J Physiol Regul Integr Comp Physiol 1998, vol. 275, 2005 American Physiological Society, pp. R10-R18.
Hortobagyi, Gabriel N., Randomized Trial of High-Dose Chemotherapy and Blood Cell Autographs for High-Risk Primary Breast Carcinoma, Journal of the National Cancer Institute, vol. 92, No. 3, Feb. 2, 2000, pp. 225-233.
Horwich, Tamara, M.D., New Advances in the Diagnosis and Management of Acute Decompensated Heart Failure, the heart.org satellite program, Rapid Review, CME Symposium presented on Nov. 8, 2004 at the Sheraton New Orleans Hotel, 4 pages.
Huang, Wann-Chu et al. Renal Denervation Prevents and Reverses Hyperinsulinemia-Induced Hypertension in Rats, Mar. 25, 1998, Hypertension 1998, vol. 32, 1998 American Heart Association, pp. 249-254.
Huang, Yifei et al., Remodeling of the chronic severely failing ischemic sheep heart after coronary microembolization: functional, energetic, structural and cellular responses, Jan. 8, 2004, Am J Physiol. Heart Circ. Physiol. 2004, vol. 286, 2004 the American Physiological Society, pp. H2141-H2150.
Hughes, Gordon B., M.D. et al., A Comparative Study of Neuropathologic Changes Following Pulsed and Direct Current Stimulation of the Mouse Sciatic Nerve, Jun. 27, 1980, American Journal of Otolaryngology, Nov. 1980, vol. 1, No. 5, pp. 378-384.
Hypertension and Renal Disease: Mechanisms, Slide Show by www.hypertensiononline.org, 22 pages Mar. 30, 2001.
Hypertension Incidence and Prevalence, Age-Specific Rates, by Gender, B.C., 2001/2002, Graph, Chronic Disease Management, May 2003, British Columbia Ministry of Health Services, 1 page.
Implantable Neurostimulation Systems, Medtronic Neurological, http://medtronic.com/neuro/paintherapies/pain_treatment_ladder/pdf/implantable_brochure.pdf; 1999, 6 pages.
Implantable Pump—The Medtronic MiniMed 2007 Implantable Insulin Pump System, Medtronic MiniMed, 2006, 5 pgs.
International Search Report and Written Opinion for PCT/US2009/069334; Applicant: Ardian, Inc.; dated Mar. 1, 2010, 10 pgs.
International Search Report and Written Opinion, PCT/US05/35693, dated Mar. 8, 2006, Applicant: Ardian, Inc., 29 pgs.
International Search Report and Written Opinion, PCT/US05/35757, dated Dec. 27, 2006, Applicant: Ardian, Inc., 8 pgs.
International Search Report and Written Opinion, PCT/US06/36120, dated Jun. 25, 2008, Applicant: Ardian, Inc., 10 pgs.
International Search Report and Written Opinion, PCT/US06/41889, dated Oct. 20, 2008, Applicant: Ardian, Inc., 7 pgs.
International Search Report and Written Opinion, PCT/US06/48822, dated Aug. 15, 2008, Applicant: Ardian, Inc., 12 pgs.
International Search Report and Written Opinion, PCT/US07/63322, dated Mar. 3, 2008, Applicant: Ardian, Inc., 10 pgs.
International Search Report and Written Opinion, PCT/US07/63324, dated Oct. 10, 2008, Applicant: Ardian, Inc., 10 pgs.
International Search Report and Written Opinion, PCT/US07/66539, dated Jan. 28, 2008, Applicant: Ardian, Inc., 6 pgs.
International Search Report and Written Opinion, PCT/US07/70799, dated Jul. 2, 2008, Applicant: Ardian, Inc., 7 pgs.
International Search Report and Written Opinion, PCT/US07/72396, dated Aug. 27, 2008, Applicant: Ardian, Inc., 9 pgs.
International Search Report and Written Opinion, PCT/US07/84701, dated Aug. 21, 2008, Applicant: Ardian, Inc., 11 pgs.
International Search Report and Written Opinion, PCT/US07/84705, dated Jul. 28, 2008, Applicant: Ardian, Inc., 12 pgs.
International Search Report and Written Opinion, PCT/US07/84708, dated Aug. 11, 2008, Applicant: Ardian, Inc., 9 pgs.
International Search Report, PCT/US02/0039, dated Sep. 11, 2002, Applicant: Advanced Neuromodulation Systems, Inc.
International Search Report, PCT/US02/25712, dated Apr. 23, 2003, Applicant: Cyberonics, Inc.
International Search Report, PCT/US03/08014, dated Sep. 23, 2003, Applicant: The General Hospital Corporation.
International Search Report, PCT/US03/09764, dated Oct. 28, 2003, Applicant: CVRX, Inc.
International Search Report, PCT/US04/38498, dated Feb. 18, 2005, Applicant: G & L Consulting, LLC, 4 pgs.
Introduction to Autonomic Pharmacology, Chapter 3, Part 2 Autonomic Pharmacology, pp. 18-26, May 24, 2002.
Isovue: Data Sheet. Regional Health Limited. 8 pgs. Mar. 11, 2003.
Israili, Z.H., Clinical pharmacokinetics of angiotensin II (AT) receptor blockers in hypertension, Journal of Human Hypertension, 2000, Macmillan Publishers Ltd., vol. 14, pp. S73-S86.
Janda, J., Impact of the electrical stimulation apparatus rebox on the course of ischemic renal damage in rats, British Library—The world's knowledge pp. 252-254 (translated and untranslated versions) 1996.
Janssen, Ben J.A. et al., Effects of complete renal denervation and selective afferent renal denervation on the hypertension induced by intrarenal norepinephrine infusion in conscious rats, Jan. 4, 1989, Journal of Hypertension 1989, vol. 7, No. 6, Current Science Ltd, pp. 447-455.
Jia, Jianping et al., Cold injury to nerves is not due to ischaemia alone, Brain. 121;pp. 989-1001. 1998.
Jia, Jianping et al.., The pathogenesis of non-freezing cold nerve injury: Observations in the rat, Brain. 120; pp. 631-646. 1997.
Jin, Yuanzhe et al., Pulmonary Vein Stenosis and Remodeling After Electrical Isolation for Treatment of Atrial Fibrillation: Short- and Medium-Term Follow-Up, PACE, vol. 27., Oct. 2004, pp. 1362-1370.
Johansson, Bjorn, Electrical Membrane Breakdown, A Possible Mediator of the Actions of Electroconvulsive Therapy, Medical Hypotheses 1987, vol. 24, Longman Group UK Ltd 1987, pp. 313-324.
Joles, J.A. et al., Causes and Consequences of Increased Sympathetic Activity in Renal Disease. Hypertension. 2004;43:699-706.
Jorgensen, William A. et al., Electrochemical Therapy of Pelvic Pain: Effects of Pulsed Electromagnetic Fields (PEMF) on Tissue Trauma, EurJ Surg 1994, Suppl 574, vol. 160, 1994 Scandinavian University Press, pp. 83-86.
Joshi, R. P. and K. H. Schoenbach, Mechanism for membrane electroporation irreversibility under high-intensity, ultrashort electrical pulse conditions, Nov. 11, 2002, Physical Review E 66, 2002, The American Physical Society 2002, pp. 052901-1-052901-4.
Joshi, R. P. et al., Improved energy model for membrane electroporation in biological cells subjected to electrical pulses, Apr. 9, 2002, Physical Review E, vol. 65, 041920-1, 2002 The American Physical Society, 8 pages.
Joshi, R. P. et al., Self-consistent simulations of electroporation dynamics in biological cells subjected to ultrashort electrical pulses, Jun. 21, 2001, Physical Review E, vol. 64, 011913, 2001 The American Physcial Society, pp. 1-10.

(56) References Cited

OTHER PUBLICATIONS

Kanduser, Masa et al., Effect of surfactant polyoxyethylene glycol (C12E8) on electroporation of cell line DC3F, Aug. 20, 2002, Colloids and Surfaces A: Physicochem. Eng. Aspects 214, 2003, Elsevier Science B.V. 2002, pp. 205-217.
Kassab, S. et al., Renal denervation attenuates the sodium retention and hypertension associated with obesity, Hypertension, 1995, 25:893-897.
Katholi, R.E. et al., Importance of the renal nerves in established two-kidney, one clip Goldblatt hypertension, Hypertension, 1982, 4 (suppl II):II-166-II-174.
Katholi, R.E. et al., Role of the renal nerves in the pathogenesis of one-kidney renal hypertension in the rat, Hypertension, 1981, 3(4) 404-409.
Katholi, R.E., Renal nerves and hypertension: an update, Fed Proc., 1985, 44:2846-2850.
Katholi, Richard E., Renal nerves in the pathogenesis of hypertension in experimental animals and humans, Am. J. Physiol. vol. 245, 1983, the American Physiological Society 1983, pp. F1-F14.
Kaye, D.M. et al., Functional and neurochemical evidence for partial cardiac sympathetic reinnervation after cardiac transplantation in humans, Circulation, 1993, vol. 88, pp. 1101-1109.
Kelleher, Catherine L. et al., Characteristics of Hypertension in Young Adults with Autosomal Dominant Polycystic Kidney Disease Compared with the General U.S. Population, Jun. 9, 2004, American Journal of Hypertension 2004, pp. 1029-1034.
King, Ronald W. P., Nerves in a Human Body Exposed to Low-Frequency Electromagnetic Fields, Jun. 7, 1999, IEEE Transactions on Biomedical Engineering, vol. 46, No. 12, Dec. 1999, IEEE 1999, pp. 1426-1431.
Kinney, Brian M., M.D., High-Tech Healing—The evolution of therapeutic electromagnetic fields in plastic surgery, Plastic Surgery Products, Jun. 2004, pp. 32-36, 3 pages.
Kirchheim, H. et al., Sympathetic modulation of renal hemodynamics, renin release and sodium excretion, Klin Wochenschr, 1989, 67:858-864.
Klein, K. et al., Impaired autofeedback regulation of hypothalamic norepinephrine release in experimental uremia. J Am Soc Nephrol. 2005;16:2081-7.
Knot, H. J. et al., Regulation of arterial diameter and wall [Ca2+] in cerebral arteries of rat by membrane potential and intravascular pressure. The Journal of Physiology. 1998. 508; pp. 199-209.
Kok, Lai Chow et al. Effect of Heating on Pulmonary Veins: How to Avoid Pulmonary Vein Stenosis. Journal of Cardiovascular Electrophysiology. vol. 14, No. 3, Mar. 2003. pp. 250-254.
Kok, R. J. et al., Specific Delivery of Captopril to the Kidney with the Prodrug Captopril-Lysozyme, Aug. 16, 1998, Journal of Pharmacology and Experimental Therapeutics, vol. 288, No. 1, 1999 by The American Society for Pharmacology and Experimental Therapeutics, pp. 281-285.
Kon, V. Neural Control of Renal Circulation, Miner Electrolyte Metab. 1989;15:33-43.
Koomans, H.A., et al., Sympathetic hyperactivity in chronic renal failure: a wake-up call. J Am Soc Nephrol. 2004;15:524-37.
Kopp, U. et al., Dietary sodium loading increases arterial pressure in afferent renal-denervated rats, Hypertension, 2003, 42:968-973.
Kopp, U.C. et al., Renal sympathetic nerve activity modulates afferent renal nerve activity by PGE2-dependent activation of alpha1- and alpha2-adrenoceptors on renal sensory nerve fibers. Am J Physiol Regul Integr Comp Physiol. 2007;293:R1561-72.
Koyama, Shozo et al., Relative Contribution of Renal Nerve and Adrenal Gland to Renal Vascular Tone During Prolonged Canine Hemorrhagic Hypotension, Sep. 24, 1992, Circulatory Shock 1993, vol. 39, Wiley-Liss, Inc. 1993, pp. 269-274.
Kozak, Lola Jean, Ph.D et al., National Hospital Discharge Survey: 2001 Annual Summary with Detailed Diagnosis and Procedure Data, Vital and Health Statistics, Serices 13 No. 156, Jun. 2004, CDC, 206 pages.
Kumagai, K. et al. New Approach to Pulmonary Vein Isolation for Atrial Fibrillation Using a Multielectrode Basket Catheter. Circulation Journal. 2006;70:88-93.
Lafayette, Richard A., M.D., How Does Knocking Out Angiotensin II Activity Reduce Renal Injury in Mice?, Jun. 14, 1999, Journal Club, American Journal of Kidney Diseases, vol. 35, No. 1, Jan. 2000, National Kidney Foundation, Inc. 2000, pp. 166-172.
Lavie, Peretz, Ph.D. and Victor Hoffstein, M.D., Sleep Apnea Syndrome: A Possible Contributing Factor to Resistant Hypertension, Jun. 2001, SLEEP 2001, vol. 24, No. 6, pp. 721-725.
Le Noble, J.L. et al., Pharmacological evidence for rapid destruction of efferent renal nerves in rats by intrarenal infusion of 6-hydroxydopamine. J Hypertens Suppl. 1985;3:S137-40.
Lee, Michael A. (editor). SPORTSMed. Connecticut State Medical Society Committee on the Medical Aspects of Sports. Fall/Winter 2005. 10 pgs.
Lee, Raphael C. et al., Biophysical Injury Mechanisms in Electronic Shock Trauma, Annu. Rev. Biomed. Eng., 2000, vol. 2, Copyright © 2000 by Annual Reviews, pp. 477-509.
Lee, Raphael C. et al., Clinical Sequelae Manifested in Electrical Shock Survivors, Presentation by the Electrical Trauma Research Program, The University of Chicago, 37 pages Dec. 24, 2004.
Lee, Raphael C., M.D., Sc.D. and Michael S. Kolodney, S.B., Electrical Injury Mechanisms: Electrical Breakdown of Cell Membranes, Oct. 1, 1986, Plastic and Reconstructive Surgery, Nov. 1987, vol. 80, No. 5, pp. 672-679.
Lenoble, L.M. et al., Selective efferent chemical sympathectomy of rat kidneys. Am J Physiol. 1985;249:R496-501.
Ligtenberg, Gerry M.D. et al., Reduction of Sympathetic Hyperactivity by Enalapril in Patients with Chronic Renal Failure, Apr. 29, 1999, New England Journal of Medicine 1999, vol. 340, No. 17, 1999 Massachusetts Medical Society, pp. 1321-1328.
Lin, Vernon W. H. et al., High intensity magnetic stimulation over the lumbosacral spine evokes antinociception in rats, Apr. 16, 2002, Clinical Neurophysiology, vol. 113, 2002 Elsevier Science Ireland Ltd., pp. 1006-1012.
Lipfert, Peter, M.D. et al., Tachyphylaxis to Local Anesthetics Does Not Result form Reduced Drug Effectiveness at the Nerve Itself, Aug. 3, 1988, Anesthesiology 1989, vol. 70, pp. 71-75.
Lohmeier, Thomas E. and Drew A. Hildebrandt, Renal Nerves Promote Sodium Excretion in Angiotensin-Induced Hypertension, Oct. 20, 1997, Hypertension 1998, vol. 31, part 2, 1998 American Heart Association, Inc., pp. 429-434.
Lohmeier, Thomas E. et al., Prolonged Activation of the Baroreflex Produces Sustained Hypotension, Harry Goldblatt Award, Nov. 26, 2003, Hypertension 2004, vol. 43, Part 2, 2004 American Heart Association, Inc., pp. 306-311.
Lohmeier, Thomas E. et al., Renal Nerves Promote Sodium Excretion During Long-Term Increases in Salt Intake, Oct. 23, 1998, Hypertension 1999, vol. 33, part II, 1999 American Heart Association, Inc., pp. 487-492.
Lohmeier, Thomas E. et al., Sustained influence of the renal nerves to attenuate sodium retention in angiotensin hypertension, Apr. 13, 2001, Am J Physiol Regulatory Integrative Comp Physiol, vol. 281, 2001 the American Physiological Society, pp. R434-R443.
Lohmeier, Thomas E., et al., Baroreflexes prevent neurally induced sodium retention in angiotensin hypertension, American Journal Physiol Regulatory Integrative Comp Physiol, vol. 279, 2000 the American Physiological Society, pp. R1437-R1448.
Lohmeier, Thomas E., Interactions Between Angiotensin Ii and Baroreflexes in Long-Term Regulation of Renal Sympathetic Nerve Activity, Circulation Research, Jun. 27, 2003, American Heart Association, Inc.2003, pp. 1282-1284.
Luff, S.E. et al., Two types of sympathetic axon innervating the juxtaglomerular arterioles of the rabbit and rat kidney differ structurally from those supplying other arteries, May 1, 1991, Journal of Neurocytology 1991, vol. 20, 1991 Chapman and Hall Ltd., pp. 781-795.
Luippold, G. et al., Chronic renal denervation prevents glomerular hyperfiltration in diabetic rats, Nephrol Dial Transplant (2004) 19:342-347.

(56) References Cited

OTHER PUBLICATIONS

Lundborg, C. et al., Clinical experience using intrathecal (IT) bupivacaine infusion in three patients with complex regional pain syndrome type I (CRPS-I), Acta Anaesthesiol Scand 1999, vol. 43, pp. 667-678.
Maeder, Micha, M.D. et al., Contrast Nephropathy: Review Focusing on Prevention, Jun. 22, 2004, Journal of the American College of Cardiology Nov. 2, 2004, vol. 44, No. 9, 2004 by the American College of Cardiology Foundation, pp. 1763-1771.
Malpas, Simon C., What sets the long-term level of sympathetic nerve activity: is there a role for arterial baroreceptors?, Invited Review, Am J Physiol Regul Integr Comp Physiol 2004, vol. 286, 2004 the American Physiological Society, pp. R1-R12.
Mancia, G., Grassi, G., Giannattasio, C., Seravalle, G., Sympathetic actrivation of pathogenesis of hypertension and progression of organ damage, Hypertension 1999, 34 (4 Pt 2): 724-728.
Marenzi, Giancarlo, M.D. et al., The Prevention of Radiocontrast-Agent-Induced Nephropathy by Hemofiltration, New England Journal of Medicine, Oct. 2, 2003, vol. 349 (14), 2003 Massachusetts Medical Society, pp. 1333-1340.
Market for infusion pumps grows with an aging population, NWL 97-01, The BBI Newsletter, vol. 20, No. 2, Feb. 1, 1997, American Health Consultants, Inc., pp. 6.
Martin, Jason B. et al., Gene Transfer to Intact Mesenteric Arteries by Electroporation, Mar. 27, 2000, Journal of Vascular Research 2000, vol. 37, 2000 S. Karger AG, Basel, pp. 372-380.
Mccreery, Douglas B. et al., Charge Density and Charge Per Phase as Cofactors in Neural Injury Induced by Electrical Stimulation, IEEE Transactions on Biomedical Engineering, vol. 17, No. 10, Oct. 1990, pp. 996-1000.
Mccullough, Peter A., M.D., MPH et al., Acute Renal Failure after Coronary Intervention: Incidence, Risk Factors and Relationship to Mortality, Apr. 14, 1997, Am J Med. 1997, vol. 103, 1997 Excerpta Medica, Inc., pp. 368-375.
Mcmurray, John J.V., M.D. and Eileen O'Meara, M.D., Treatment of Heart Failure with Spironolactone—Trial and Tribulations, Aug. 5, 2004, New England Journal of Medicine, vol. 351, No. 6, 2004 Massachusetts Medical Society, pp. 526-528.
Mcrobbie, D. and M.A. Foster, Thresholds for biological effects of time-varying magnetic fields, Dec. 16, 1983, Clin. Phys. Physiol. Meas. 1984, vol. 5, No. 2, 1984 The Institute of Physics, pp. 67-78.
Medtronic Neurostimulation Systems, Expanding the Array of Pain Control Solutions, informational pamphlet, 1999 Medtronic, Inc., 6 pages.
Medtronic, Spinal Cord Stimulation, Patient Management Guidelines for Clinicians, Medtronic, Inc. 1999, 115 pages.
Medtronic, SynchroMed Infusion System—Clinical Reference Guide for Pain Therapy, Medtronic, Inc. 1998, 198 pages.
Mehran, Roxana, Renal insufficiency and contrast nephropathy: The most common, least understood risk factor, Cardiovascular Research Foundation, Columbia University Medical Center, 2005, 86 slides.
Mess, Sarah A., M.D. et al., Implantable Baclofen Pump as an Adjuvant in Treatment of Pressure Sores, Mar. 1, 2003, Annals of Plastic Surgery, vol. 51, No. 5, Nov. 2003, Lippincott Williams & Wilkins 2003, pp. 465-467.
Micro ETS Hyperhidrosis Usa Hyperhidrosis USA. 2 pgs. <URL: http://www.hyperhidrosis-usa.com/Index.html>. Nov. 6, 2006.
Mihran, Richard T. et al., Temporally-Specific Modification of Myelinated Axon Excitability in Vitro Following a Single Ultrasound Pulse, Sep. 25, 1989, Ultrasound in Med. & Biol. 1990, vol. 16, No. 3, pp. 297-309.
Miklavčič, D. et al, A Validated Model of in Vivo Electric Field Distribution in Tissues for Electrochemotherapy and for Dna Electrotransfer for Gene Therapy, Biochimica et Biophysica Acta, 1523, 2000, pp. 73-83, <http:www.elsevier.com/locate/bba>.
Mitchell, G. A. G., The Nerve Supply of the Kidneys, Aug. 20, 1949, Acta Anatomica, vol. X, Fasc. 1/2, 1950, pp. 1-37.
Morrisey, D.M. et al., Sympathectomy in the treatment of hypertension: Review of 122 cases, Lancet. 1953;1:403-408.
Moss, Nicholas G., Renal function and renal afferent and efferent nerve activity, Am. J. Physiol. 1982, vol. 243, 1982 the American Physiological Society, pp. F425-F433.
Munglani, Rajesh, The longer term effect of pulsed radiofrequency for neuropathic pain, Jun. 8, 1998, Pain 80, 1999, International Association for the Study of Pain 1999, Published by Elsevier Science B.V., pp. 437-439.
Naropin (ropivacaine HCI) Injection, RX only Description, AstraZeneca 2001, 3 pages.
National High Blood Pressure Education Program, 1995 Update of the Working Group Reports on Chronic Renal Failure and Renovascular Hypertension, presentation, 13 pages.
National Kidney Foundation, Are You at Increased Risk for Chronic Kidney Disease?, 2002 National Kidney Foundation, Inc., 14 pages.
Nelson, L. et al., Neurogenic Control of Renal Function in Response to Graded Nonhypotensive Hemorrahage in Conscious Dogs, Sep. 13, 1992, Am J. Physiol. 264, 1993, American Physiological Society 1993, pp. R661-R667.
Nikolsky, Eugenia, M.D. et al., Radiocontrast Nephropathy: Identifying the High-Risk Patient and the Implications of Exacerbating Renal Function, Rev Cardiovasc Med. 2003, vol. 4, Supp. 1, 2003 MedReviews, LLC, pp. S7-S14.
Non-Final Office Action; U.S. Appl. No. 10/408,665; dated Mar. 21, 2006, 14 pgs.
Non-Final Office Action; U.S. Appl. No. 11/129,765; dated May 18, 2007, 10 pgs.
Non-Final Office Action; U.S. Appl. No. 11/129,765; dated Sep. 10, 2007, 5 pgs.
Non-Final Office Action; U.S. Appl. No. 11/129,765; dated Oct. 6, 2006, 30 pgs.
Non-Final Office Action; U.S. Appl. No. 11/133,925; dated Oct. 8, 2008, 41 pgs.
Non-Final Office Action; U.S. Appl. No. 11/144,173; dated Apr. 5, 2007, 33 pgs.
Non-Final Office Action; U.S. Appl. No. 11/144,173; dated Sep. 10, 2007, 5 pgs.
Non-Final Office Action; U.S. Appl. No. 11/144,298; dated Oct. 29, 2009, 8 pgs.
Non-Final Office Action; U.S. Appl. No. 11/144,298; dated Apr. 5, 2007, 33 pgs.
Non-Final Office Action; U.S. Appl. No. 11/144,298; dated Sep. 10, 2007, 5 pgs.
Non-Final Office Action; U.S. Appl. No. 11/144,298; dated Dec. 29, 2008, 7 pgs.
Non-Final Office Action; U.S. Appl. No. 11/145,122; dated Apr. 11, 2007, 33 pgs.
Non-Final Office Action; U.S. Appl. No. 11/145,122; dated Sep. 10, 2007, 5 pgs.
Non-Final Office Action; U.S. Appl. No. 11/189,563; dated May 28, 2009, 5 pgs.
Non-Final Office Action; U.S. Appl. No. 11/233,814; dated Jun. 17, 2008, 12 pgs.
Non-Final Office Action; U.S. Appl. No. 11/252,462; dated Feb. 22, 2010, 6 pgs.
Non-Final Office Action; U.S. Appl. No. 11/266,993; dated Jul. 8, 2009, 5 pgs.
Non-Final Office Action; U.S. Appl. No. 11/266,993; dated Dec. 30, 2008, 7 pgs.
Non-Final Office Action; U.S. Appl. No. 11/363,867; dated Sep. 25, 2008, 10 pgs.
Non-Final Office Action; U.S. Appl. No. 11/368,553; dated May 18, 2010, 4 pgs.
Non-Final Office Action; U.S. Appl. No. 11/368,553; dated Oct. 7, 2009, 5 pgs.
Non-Final Office Action; U.S. Appl. No. 11/368,809; dated Dec. 3, 2009, 4 pgs.
Non-Final Office Action; U.S. Appl. No. 11/368,949; dated Jun. 11, 2010, 6 pgs.
Non-Final Office Action; U.S. Appl. No. 11/368,971; dated Aug. 24, 2010, 9 pgs.
Non-Final Office Action; U.S. Appl. No. 11/451,728; dated Jun. 12, 2008, 41 pgs.

(56) References Cited

OTHER PUBLICATIONS

Non-Final Office Action; U.S. Appl. No. 11/451,728; dated Jul. 2, 2009, 5 pgs.
Non-Final Office Action; U.S. Appl. No. 11/451,728; dated Dec. 28, 2009, 7 pgs.
Non-Final Office Action; U.S. Appl. No. 11/504,117; dated Mar. 31, 2009, 10 pgs.
Non-Final Office Action; U.S. Appl. No. 11/599,649; dated Mar. 30, 2009, 10 pgs.
Non-Final Office Action; U.S. Appl. No. 11/599,649; dated Jun. 23, 2008, 9 pgs.
Non-Final Office Action; U.S. Appl. No. 11/599,723; dated Jun. 26, 2009, 17 pgs.
Non-Final Office Action; U.S. Appl. No. 11/599,723; dated Oct. 15, 2010, 16 pgs.
Non-Final Office Action; U.S. Appl. No. 11/599,882; dated Jul. 6, 2009, 13 pgs.
Non-Final Office Action; U.S. Appl. No. 11/688,178; dated Jun. 28, 2010, 5 pgs.
Non-Final Office Action; U.S. Appl. No. 11/840,142; dated Apr. 3, 2009, 13 pgs.
Non-Final Office Action; U.S. Appl. No. 12/567,521; dated Sep. 3, 2010, 9 pgs.
Nozawa, T.et al., Effects of Long Term Renal Sympathetic Denervation on Heart Failure After Myocardial Infarction in Rats, Sep. 22, 2001, Heart Vessels, 2002, 16, Springer-Verlag 2002, pp. 51-56.
O'Hagan, K.P. et al.,Renal denervation decreases blood pressure in DOCA-treated miniature swine with established hypertension, Am J Hypertens., 1990, 3:62-64.
Onesti, G. et al., Blood pressure regulation in end-stage renal disease and anephric man, Circ Res Suppl., 1975, 36 & 37: 145-152.
Osborn, et al., Effect of renal nerve stimulation on renal blood flow autoregulation and antinatriuresis during reductions in renal perfusion pressure, in Proceedings of the Society for Experimental Biology and Medicine, vol. 168, 77-81, 1981. (Abstract).
Packer, Douglas L. et al., Clinical Presentation, Investigation, and Management of Pulmonary Vein Stenosis Complication Ablation for Atrial Fibrillation, Circulation: Journal of the American Heart Association. Feb. 8, 2005. pp. 546-554.
Page, I.H. et al., The Effect of Renal Denervation on the Level of Arterial Blood Pressure and Renal Function in Essential Hypertension. J Clin Invest. 1934;14:27-30.
Page, I.H., et al., The Effect of Renal Efficiencyof Lowering Arterial Blood Pressure in Cases of Essential Nephritis, Hospital of the Rockefeller Institue, Jul. 12, 1934, 7 pgs.
Pappone, Carlo et al., [2005][P2-70] Safety Report of Circumferential Pulmonary Vein Ablation. A 9-Year Single-Center Experience on 6,442 Patients with Atrial Fibrillation, Abstract only. 1 page, May 2005.
Pappone, Carol and Santinelli, Vincenzo. Multielectrode basket catheter: A new tool for curing atrial fibrillation? Heart Rhythm, vol. 3, Issue 4, pp. 385-386. Apr. 2006.
Peacock, J.M. and R. Orchardson, Action potential conduction block of nerves in vitro by potassium citrate, potassium tartrate and potassium oxalate, May 6, 1998, Journal of Clinical Periodontology, Munksgaard 1999, vol. 26, pp. 33-37.
Petersson, M. et al., Long-term outcome in relation to renal sympathetic activity in patients with chronic heart failure. Eur Heart J. 2005;26:906-13.
Pettersson, A. et al., Renal interaction between sympathetic activity and Anp in rats with chronic ischaemic heart failure, Nov. 25, 1988, Acta Physiol Scand 1989, 135, pp. 487-492.
PHCL 762 Pharmacology of the Autonomic Nervous System, Chapter 2 and 6.8 in Mosby, http://www.kumc.edu/research/medicine/pharmacology/CAI/phcl762.html, last accessed Aug. 24, 2004, 14 pgs.
Pitt, B. et al., Effects of Eplerenone, Enalapril, and Eplerenone/Enalapril in Patients With Essential Hypertension and Left Ventricular Hypertrophy: The 4E-Left Ventricular Hypertrophy Study, Circulation, 2003, vol. 108, pp. 1831-1838.
Pliquett, U., Joule heating during solid tissue electroporation, Oct. 22, 2002, Med. Biol. Eng. Comput., 2003, vol. 41, pp. 215-219.
Podhajsky R.J. et al, The Histologic Effects of Pulsed and Continuous Radiofrequency Lesions at 42 C to Rat Dorsal Root Ganglion and Sciatic Nerve, SPINE, vol. 30, No. 9, 2005, Lippincott Williams & Wilkins Inc., pp. 1008-1013.
Pope, Jill. Fixing a Hole: Treating Injury by Repairing Cells. The New York Academy of Sciences. Jul. 6, 2006. 6 pgs.
Popovic, Jennifer R. and Margaret J. Hall, 1999 National Hospital Discharge Survey, Apr. 24, 2001, Advance Data, No. 319, CDC, pp. 1-17 & 20.
Practice Guidelines Writing Committee and ESH/ESC Hypertension Guidelines Committee, Practice Guidelines for Primary Care Physicians: 2003 ESH/ESC Hypertension Guidelines, Published in Journal of Hypertension 2003, vol. 21, No. 10: 1011-1053, European Society of Hypertension 2003, pp. 1779-1786.
Programmable Infusion System, Pumps and Pump Selection, Medtronic Pain Therapies, Medtronic, Inc. Sep. 5, 2001, 2 pgs.
Pucihar, Gorazd et al., The influence of medium conductivity on electropermeabilization and survival of cells in vitro, May 31, 2001, Bioelectrochemistry, vol. 54, 2001, Elsevier Science B.V. 2001, pp. 107-115.
Pulmonary Concepts in Critical Care Breath Sounds, http://rnbob.tripod.com/breath.htm, last accessed Aug. 23, 2004, 5 pages.
Pulmonary Function Testing, http://jan.ucc.nau.edu/~daa/lecture/pft.htm, last accessed Aug. 23, 2004, 8 pages.
Purerfellner, Helmut and Martinek, Martin. Pulmonary vein stenosis following catheter ablation of atrial fibrillation. Current Opinion in Cardiology. 20; pp. 484-490. 2005.
Purerfellner, Helmut et al., Pulmonary Vein Stenosis by Ostial Irrigated-Tip Ablation: Incidence, Time Course, and Prediction, Journal of Cardiovascular Electrophysiology. vol. 14, No. 2, Feb. 2003. pp. 158-164.
Raji, A. R. M. and R. E. M. Bowden, Effects of High-Peak Pulsed Electromagnetic Field on the Degeneration and Regeneration of the Common Peroneal Nerve in Rats, The Journal of Bone and Joint Surgery Aug. 1983, vol. 65-B, No. 4, 1983 British Editorial Society of Bone and Joint Surgery, pp. 478-492.
Ravalia, A. et al., Tachyphylaxis and epidural anaesthesia, Edgware General Hospital, Correspondence, p. 529, Jun. 1989.
Ribstein, Jean and Michael H. Humphreys, Renal nerves and cation excretion after acute reduction in functioning renal mass in the rat, Sep. 22, 1983, Am. J. Physiol., vol. 246, 1984 the American Physiological Society, pp. F260-F265.
Richebe, Philippe, M.D. et al., Immediate Early Genes after Pulsed Radiofrequency Treatment: Neurobiology in Need of Clinical Trials, Oct. 13, 2004, Anesthesiology Jan. 2005, vol. 102, No. 1, 2004 American Society of Anesthesiologists, Inc. Lippincott Williams & Wilkins, Inc., pp. 1-3.
Rihal, Charanjit S. et al., Incidence and Prognostic Importance of Acute Renal Failure After Percutaneous Coronary Intervention, Mar. 6, 2002, Circulation May 14, 2002, vol. 10, 2002 American Heart Association, Inc., pp. 2259-2264.
Rosen, S.M. et al., Relationship of Vascular Reactivity to Plasma Renin Concentration in Patients with Terminal Renal Failure, Proc. Dialysis Transplant Forum 1974, pp. 45-47.
Rudnick, Michael R. et al., Contrast-induced nephropathy: How it develops, how to prevent it, Cleveland Clinic Journal of Medicine Jan. 2006, vol. 73, No. 1, pp. 75-87.
Rump, L.C., The Role of Sympathetic Nervous Activity in Chronic Renal Failure, J Clinical Basic Cardiology 2001, vol. 4, pp. 179-182.
Ruohonen, Jarmo et al., Modeling Peripheral Nerve Stimulation Using Magnetic Fields, Journal of the Peripheral Nervous System, vol. 2, No. 1, 1997, Woodland Publications 1997, pp. 17-29.
Saad, Eduardo B. et al., Pulmonary Vein Stenosis After Radiofrequency Ablation of Atrial Fibrillation: Functional Characterization, Evolution, and Influence of the Ablation Strategy, Circulation. 108; pp. 3102-3107. 2003.
Sabbah, Hani N., Animal Models for Heart Failure and Device Development, Henry Ford Health System. 24 slides, Oct. 17, 2005.

(56) References Cited

OTHER PUBLICATIONS

Schauerte, P et al., Focal atrial fibrillation: experimental evidence for a pathophysiologic role of the autonomic nervous system, Journal of Cardiovascular Electrophysiology. 12(5). May 2001. Abstract only. 2 pgs.
Schauerte, P et al., Transvenous parasympathetic nerve stimulation in the inferior vena cava and atrioventricular conduction, Journal of Cardiovascular Electrophysiology. 11(1). Jan. 2000. Abstract only. 2 pgs.
Scheiner, Avram, Ph.D., The design, development and implementation of electrodes used for functional electrial stimulation, Thesis paper, Case Western Reserve University, May 1992, 220 pages.
Scherlag, BJ and Po, S., The intrinsic cardiac nervous system and atrial fibrillation, Current Opinion in Cardiology. 21(1):51-54, Jan. 2006. Abstract only. 2 pgs.
Schlaich, M.P. et al., Relation between cardiac sympathetic activity and hypertensive left ventricular hypertrophy. Circulation. 2003;108:560-5.
Schlaich, M.P. et al., Sympathetic augmentation in hypertension: role of nerve firing, norepinephrine reuptake, and angiotensin neuromodulation, Hypertension, 2004, 43:169-175.
Schmitt, Joseph et al., Intravascular Optical Coherence Tomography—Opening a Window into Coronary Artery Disease, LightLab Imaging, Inc. Business Briefing: European Cardiology 2005.
Schoenbach, Karl H. et al, Intracellular Effect of Ultrashort Electrical Pulses, Dec. 26, 2000, Bioelectromagnetics, vol. 22, 2001, Wiley-Liss, Inc. 2001, pp. 440-448.
Schrier, Robert et al., Cardiac and Renal Effects of Standard Versus Rigorous Blood Pressure Control in Autosomal-Dominant Polycistic Kidney Disease, Mar. 23, 2002, Journal of the American Society of Nephrology, American Society of Nephrology 2002, pp. 1733-1739.
Scremin, Oscar U., M.D., Ph.D. and Daniel P. Holschneider, M.D., 31 & 32 . . . An Implantable Bolus Infusion Pump for the Neurosciences, FRP, Apr. 2005, 3 pages.
Sensorcaine—MPF Spinal Injection, informational document, AstraZeneca 2001, 2 pgs.
Shah, D.C., Haissaguerre, M., Jais, P., Catheter ablation of pulmonary vein foci for atrial fibrillation: pulmonary vein foci ablation for atrial firbrillation, Thorac Cardiovasc Surg, 1999, 47 (suppl. 3): 352-356.
Shannon, J.L. et al., Studies on the innervation of human renal allografts, J Pathol. 1998, vol. 186, pp. 109-115.
Shlipak, M.G. et al., The clinical challenge of cardiorenal syndrome. Circulation. 2004;110:1514-7.
Shu-Qing, Liu et al., Old spinal cord injury treated by pulsed electric stimulation, General Hospital of Beijing Command, Beijing, Dec. 6, 1990, 5 pages (full article in Chinese; abstract on last page).
Simpson, B. et al., Implantable spinal infusion devices for chronic pain and spasticity: an accelerated systematic review, ASERNIP-S Report No. 42, Adelaide, South Australia, ASERNIP-S, May 2003, 56 pages.
Sisken, B.F. et al., 229.17 Influence of Non-Thermal Pulsed Radiofrequency Fields (PRF) on Neurite Outgrowth, Society for Neuroscience, vol. 21, 1995, 2 pages.
Skeie, B. et al., Effect of chronic bupivacaine infusion on seizure threshold to bupivacaine, Dec. 28, 1986, Acta Anaesthesiol Scand 1987, vol. 31, pp. 423-425.
Skopec, M., A Primer on Medical Device Interactions with Magnetic Resonance Imaging Systems, Feb. 4, 1997, CDRH Magnetic Resonance Working Group, U.S. Department of Heatlh and Human Services, Food and Drug Administration, Center for Devices and Radiological Health, Updated May 23, 1997, 17 pages, http://www.fda.gov/cdrh/ode/primerf6.html, (last accessed Jan. 23, 2006.
Slappendel, Robert et al., The efficacy of radiofrequency lesioning of the cervical spinal dorsal root ganglion in a double blinded randomized study, Jun. 26, 1997, Pain 73, 1997 International Association for the Study of Pain, Elsevier Science B.V., pp. 159-163.

Sluijter, M.D., Ph.D., Pulsed Radiofrequency, May 17, 2005, Anesthesiology Dec. 2005, vol. 103, No. 6, 2005 American Society of Anesthesiologists, Inc. Lippincott Williams & Wilkins, Inc., pp. 1313-1314.
Sluijter, M.D., Ph.D., Radiofrequency Part 1: The Lumbosacral Region, Chapter 1 Mechanisms of Chronic Pain and part of Chapter 2 Spinal Pain, 2001 FlivoPress SA, Meggen (LU), Switzerland, pp. 1-26.
Sluijter, M.D., Ph.D., Radiofrequency Part 2: Thoracic and Cervical Region, Headache and Facial Pain, various pages from, FlivoPress SA, Meggen (LU), Switzerland, 13 pages 2002.
Sluijter, M.D., Ph.D., The Role of Radiofrequency in Failed Back Surgery Patients, Current Review of Pain 2000, vol. 4, 2000 by Current Science Inc., pp. 49-53.
Smithwick, R.H. et al., Splanchnicectomy for essential hypertension, Journal Am Med Assn, 1953;152:1501-1504.
Smithwick, R.H., Surgical treatment of hypertension, Am J Med 1948, 4:744-759.
Sobotka, Paul A., Treatment Strategies for Fluid Overload, CHF Patients, CHF Solutions. Transcatheter Cardiovascular Therapeutics 2005. 20 slides.
Solis-Herruzo, J.A. et al., Effects of lumbar sympathetic block on kidney function in cirrhotic patients with hepatorenal syndrome, Journal of Hepatology, 1987; 5: 167-173.
Souza, D.R.B. et al., Chronic experimental myocardial infarction produces antinatriuresis by a renal nerve-dependent mechanism, Oct. 14, 2003, Brazilian Journal of Medical and Biological Research 2004, vol. 37, pp. 285-293.
Standl, Thomas, M.D., et al., Patient-controlled epidural analgesia reduces analgesic requirements compared to continuous epidural infusion after major abdominal surgery, Aug. 29, 2002, Canada Journal of Anesthesia 2003, vol. 50 (3), pp. 258-264.
Steffen, W. et al., Catheter-delivered high intensity, low frequency ultrasound induces vasodilation in vivo, European Heart Journal. 1994. 15; pp. 369-376.
Steg, PG et al., Pulsed ultraviolet laser irradiation produces endothelium-independent relaxation of vascular smooth muscle, Circulation: Journal of the American Heart Association. 1989. pp. 189-197.
Stone, Gregg W., M.D. et al., Fenoldopam Mesylate for the Prevention of Contrast-Induced Nephropathy, JAMA Nov. 5, 2003, vol. 290, No. 17, 2003 American Medical Association, pp. 2284-2291.
Strojek, K. et al., Lowering of microalbuminuria in diabetic patients by a sympathicoplegic agent: novel approach to prevent progression of diabetic nephropathy? J Am Soc Nephrol. 2001;12:602-5.
Summary, Critical Reviews in Biomedical Engineering, vol. 17, Issue 5, 1989, pp. 515-529.
Sung, Duk Hyun, M.D. et al., Phenol Block of Peripheral Nerve Conduction: Titrating for Optimum Effect, Jun. 27, 2000, Arch. Phys. Med. Rehabil. vol. 82, May 2001, pp. 671-676.
Taka, Tomomi et al., Impaired Flow-Mediated Vasodilation in vivo and Reduced Shear-Induced Platelet Reactivity in vitro in Response to Nitric Oxide in Prothrombotic, Stroke-Prone Spontaneously Hypertensive Rats, Pathophysiology of Haemostasis and Thrombosis. Dec. 23, 2002. pp. 184-189.
Taler, Sandra J. et al., Resistant Hypertension, Comparing Hemodynamic Management to Specialist Care, Mar. 12, 2002, Hypertension 2002, vol. 39, 2002 American Heart Association, Inc., pp. 982-988.
Tamborero, David et al., Incidence of Pulmonary Vein Stenosis in Patients Submitted to Atrial Fibrillation Ablation: A Comparison of the Selective Segmental Ostial Ablation vs. the Circumferential Pulmonary Veins Ablation, Journal of Intervocational Cardiac Electrophysiology. 14; pp. 41-25. 2005.
Tay, Victoria KM, et al., Computed tomography fluoroscopy-guided chemical lumbar sympathectomy: Simple, safe and effective, Oct. 31, 2001, Diagnostic Radiology, Australasian Radiology 2002, vol. 46, pp. 163-166.
Thatipelli et al., CT Angiography of Renal Artery Anatomy for Evaluating Embolic Protection Devices, Journal of Vascular and Interventional Radiology, Jul. 2007, pp. 842-846.

(56) References Cited

OTHER PUBLICATIONS

Thomas, John R. and Oakley, E. Howard N. Chapter 15: Nonfreezing Cold Injury Medical Aspects of Harsh Environments, vol. 1. pp. 467-490, 2001.
Thompson, Gregory W., et al., Bradycardia Induced by Intravascular Versus Direct Stimulation of the Vagus Nerve, Aug. 24, 1997, The Society of Thoracic Surgeons 1998, pp. 637-642.
Thrasher, Terry N., Unloading arterial baroreceptors causes neurogenic hypertension, Dec. 4, 2001, Am J. Physiol Regulatory Integrative Comp Physiol, vol. 282, 2002 the American Physiological Society, pp. R1044-R1053.
Tokuno, Hajime A. et al., Local anesthetic effects of cocaethylene and isopropylcocaine on rat peripheral nerves, Oct. 7, 2003, Brain Research 996, 2004, Elsevier B.V. 2003, pp. 159-167.
Trapani, Angelo J. et al., Neurohumoral interactions in conscious dehydrated rabbit, Am. J. Physiol. 254, 1988, the American Physiological Society 1988, pp. R338-R347.
Troiano, Gregory C. et al., The Reduction in Electroporation Voltages by the Addition of a Surfactant to Planar Lipid Bilayers, May 12, 1998, Biophysical Journal, vol. 75, Aug. 1998, the Biophysical Society 1998, pp. 880-888.
Trumble, Dennis R. and James A. MaGovern, Comparison of Dog and Pig Models for Testing Substernal Cardiac Compression Devices, Nov. 2003, ASAIO Journal 2004, pp. 188-192.
Tsai, E., Intrathecal drug delivery for pain indications, technique, results, Pain Lecture presentation, Jun. 8, 2001, 31 pages.
Uematsu, Toshihiko, M.D., Ph.D., F.I.C.A. et al., Extrinsic Innervation of the Canine Superior Vena Cava, Pulmonary, Portal and Renal Veins, Angiology—Journal of Vascular Diseases, Aug. 1984, pp. 486-493.
United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.
Upadhyay, Pramod, Electroporation of the skin to deliver antigen by using a piezo ceramic gas igniter, Jan. 27, 2001, International Journal of Pharmaceutics, vol. 217, 2001 Elsevier Science B.V., pp. 249-253.
Valente, John F. et al., Laparoscopic renal denervation for intractable ADPKD-related pain, Aug. 24, 2000, Nephrol Dial Transplant 2001, vol. 16, European Renal Association-European Dialysis and Transplant Association, p. 160.
Velazquez, Eric J., An international perspective on heart failure and left ventricular systolic dysfunction complicating myocardial infarction: the VALIANT registry, Aug. 5, 2004, European Heart Journal vol. 25, 2004 Elsevier, pp. 1911-1919.
Velez-Roa, Sonia, M.D. et al., Peripheral Sympathetic Control During Dobutamine Infusion: Effects of Aging and Heart Failure, Jul. 7, 2003, Journal of the American College of Cardiology, vol. 42, No. 9, 2003, American College of Cardiology Foundation 2003, pp. 1605-1610.
Villarreal, Daniel et al., Effects of renal denervation on postprandial sodium excretion in experimental heart failure, Oct. 29, 1993, Am J Physiol 266, 1994, pp. R1599-R1604.
Villarreal, Daniel et al., Neurohumoral modulators and sodium balance in experimental heart failure, Nov. 6, 1992, Am. J. Physiol, vol. 264, 1993, pp. H1187-H1193.
Vonend, O. et al., Moxonidine treatment of hypertensive patients with advanced renal failure. J Hypertens. 2003;21:1709-17.
Wagner, C.D. et al., Very low frequency oscillations in arterial blood pressure after autonomic blockade in conscious dogs, Feb. 5, 1997, Am J Physiol Regul Integr Comp Physiol 1997, vol. 272, 1997 the American Physiological Society, pp. 2034-2039.
Wald, Jan D., Ph.D, et al., Cardiology Update: 2003, Sep. 11, 2003, AG Edwards 2003, 120 pages.
Wang, Xi et al., Alterations of adenylyl cyclase and G proteins in aortocaval shunt-induced heart failure, Jul. 2004, Am J Physiol Heart Circ Physiol vol. 287, 2004 the American Physiological Society, pp. H118-H125.

Weaver, James C., Chapter 1 Electroporation Theory, Concepts and Mechanisms, Methods in Molecular Biology, vol. 55, Plant Cell Electroporation and Electrofusion Protocols, Edited by J.A. Nickoloff, Humana Press Inc., pp. 3-28, 1995.
Weaver, James C., Electroporation: A General Phenomenon for Manipulating Cells and Tissues, Oct. 22, 1992, Journal of Cellular Biochemistry, vol. 51, 1993 Wiley-Liss, Inc., pp. 426-435.
Weiner, Richard L., M.D., Peripheral nerve neurostimulation, Neurosurg. Clin. N. Am. vol. 14, 2003, Elsevier, Inc. 2003, pp. 401-408.
Weisbord, Steven D., M.D. and Paul M. Palevsky, M.D., Radiocontrast-Induced Acute Renal Failure, Jul. 10, 2004, Journal of Intensive Care Medicine 2005, vol. 20 (2), 2005 Sage Publications, pp. 63-75.
Whitelaw, G.P., Kinsey, D., Smithwick, R.H., Factors influencing the choice of treatment in essential hypertension: surgical, medical, or a combination of both, Am J Surg, 1964, 107:220-231.
Wilson, D.H. et al., The Effects of Pulsed Electromagnetic Energy on Peripheral Nerve Regeneration, Annals New York Academy of Sciences, Oct. 1974, pp. 575-585.
Wyss, J. Michael et al., Neuronal control of the kidney: Contribution to hypertension, Apr. 8, 1991, Can. J. Physiol. Pharmacol. 1992;70: 759-770.
Yamaguchi, Jun-ichi, M.D. et al., Prognostic Significance of Serum Creatinine Concentration for In-Hospital Mortality in Patients with Acute Myocardial Infarction Who Underwent Successful Primary Percutaneous Coronary Intervention (from the Heart Institute of Japan Acute Myocardial Infarction [HIJAMI] Registry), Feb. 24, 2004, The American Journal of Cardiology vol. 93, Jun. 15, 2004, 2004 by Excerpta Medica, Inc., pp. 1526-1528.
Ye, Richard D., M.D., Ph.D., Pharmacology of the Peripheral Nervous System, E-425 MSB, 6 pages, Jan. 2000.
Ye, S. et al., A limited renal injury may cause a permanent form of neurogenic hypertension. Am J Hypertens. 1998;11:723-8.
Ye, Shaohua et al., Renal Injury Caused by Intrarenal Injection of Pheno Increases Afferent and Efferent Renal Sympathetic Nerve Activity, Mar. 12, 2002, American Journal of Hypertension, Aug. 2002, vol. 15, No. 8, 2002 the American Journal of Hypertension, Ltd. Published by Elsevier Science Inc., pp. 717-724.
Yong-Quan, Dong et al., The therapeutic effect of pulsed electric field on experimental spinal cord injury, Beijing Army General Hospital of People's Liberation Army, Beijing, 5 pages (full article in Chinese; abstract on last page) Mar. 30, 1992.
Young, James B., M.D., FACC, Management of Chronic Heart Failure: What Do Recent Clinical Trials Teach Us?, Reviews in Cardiovascular Medicine, vol. 5, Suppl. 1, 2004, MedReviews, LLC 2004, pp. S3-S9.
European Search Report for European App. No. 13168823, dated Oct. 23, 2013, 7 pages.
European Search Report for European App. No. 13168822, dated Oct. 24, 2013, 7 pages.
European Search Report for European App. No. 13168821, dated Oct. 24, 2013, 7 pages.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.
Avitall et al., "The creation of linear contiguous lesions in the atria with an expandable loop catheter," Journal of the American College of Cardiology, 1999; 33; pp. 972-984.
Beale et al., "Minimally Invasive Treatment for Varicose Veins: A Review of Endovenous Laser Treatment and Radiofrequency Ablation". Lower Extremity Wounds 3(4), 2004, 10 pages.
Blessing, Erwin et al., Cardiac Ablation and Renal Denervation Systems Have Distinct Purposes and Different Technical Requirements, JACC Cardiovascular Interventions, vol. 6, No. 3, 2013, 1 page.
ClinicalTrials.gov, Renal Denervation in Patients with uncontrolled Hypertension in Chinese (2011), 6pages. www.clinicaltrials.gov/ct2/show/NCT01390831.

(56) References Cited

OTHER PUBLICATIONS

Dodge, et al., "Lumen Diameter of Normal Human Coronary Arteries Influence of Age, Sex, Anatomic Variation, and Left Ventricular Hypertrophy or Dilation", Circulation, 1992, vol. 86 (1), 232-246 pp.
Excerpt of Operator's Manual of Boston Scientific's EPT-1000 XP Cardiac Ablation Controller & Accessories, Version of Apr. 2003, (6 pages).
Excerpt of Operator's Manual of Boston Scientific's Maestro 30000 Cardiac Ablation System, Version of Oct. 17, 2005, (4 pages).
Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.
Kandarpa, Krishna et al., "Handbook of Interventional Radiologic Procedures", Third Edition, pp. 194-210 (2002).
Mount Sinai School of Medicine clinical trial for Impact of Renal Sympathetic Denervation of Chronic Hypertension, Mar. 2013, 11 pages. http://clinicaltrials.gov/ct2/show/NCT01628198.
Opposition to European Patent No. 2465470, Granted Oct. 28, 2015, Date of Opposition Jul. 27, 2016, 34 pp.
Opposition to European Patent No. EP1802370, Granted Jan. 5, 2011, Date of Opposition Oct. 5, 2011, 20 pages.
Opposition to European Patent No. EP2037840, Granted Dec. 7, 2011, Date of Opposition Sep. 7, 2012, 25 pages.
Opposition to European Patent No. EP2092957, Granted Jan. 5, 2011, Date of Opposition Oct. 5, 2011, 26 pages.
Oz, Mehmet, Pressure Relief, TIME, Jan. 9, 2012, 2 pages. <www.time.come/time/printout/0,8816,2103278,00.html>.
Papademetriou, Vasilios, Renal Sympathetic Denervation for the Treatment of Difficult-to-Control or Resistant Hypertension, Int. Journal of Hypertension, 2011, 8 pages.
Pieper et al., "Design and Implementation of a New Computerized System for Intraoperative Cardiac Mapping." Journal of Applied Physiology, 1991, vol. 71, No. 4, pp. 1529-1539.
Prochnau, Dirk et al., Catheter-based renal denervation for drug-resistant hypertension by using a standard electrophysiology catheter; Euro Intervention 2012, vol. 7, pp. 1077-1080.
Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.
Purerfellner, Helmut et al., Pulmonary Vein Stenosis Following Catheter Ablation of Atrial Fibrillation, Curr. Opin. Cardio. 20 :484-490, 2005.
Remo, Benjamin F. et al., "Safety and Efficacy of Renal Denervation as a Novel Treatment of Ventricular Tachycardia Storm in Patients with Cardiomyopathy." Heart Rhythm, 2014, 11(4), 541-6.
Schneider, Peter A., "Endovascular Skills—Guidewire and Catheter Skills for Endovascular Surgery," Second Edition Revised and Expanded, 10 pages, (2003).
ThermoCool Irrigated Catheter and Integrated Ablation System, Biosense Webster (2006), 6 pages.
Tsao, Hsuan-Ming, Evaluation of Pulmonary Vein Stenosis after Catheter Ablation of Atrial Fibrillation, Cardiac Electrophysiology Review, 6, 2002, 4 pages.
U.S. Appl. No. 11/363,867, filed Feb. 27, 2006, 70 pp.
U.S. Appl. No. 60/813,589, filed Dec. 29, 2005, 62 pp.
U.S. Appl. No. 60/852,787, filed Oct. 18, 2006, 112 pages.
Ureter, https://en.wikipedia.org/wiki/Ureter, Jun. 2016, 6 pp.
Wittkampf et al., "Control of radiofrequency lesion size by power regulation," Journal of the American Heart Associate, 1989, 80: pp. 962-968.
Zheng et al., "Comparison of the temperature profile and pathological effect at unipolar, bipolar and phased radiofrequency current configurations," Journal of Interventional Cardiac Electrophysiology, 2001, pp. 401-410.
Demarais et al., Reexamination Application 95/002,110 U.S. Pat. No. 7,717,948 filed Aug. 29, 2012.
Non-Final Office Action; U.S. Appl. No. 12/616,708; dated Sep. 16, 2010, 10 pgs.
Non-Final Office Action; U.S. Appl. No. 12/725,375; dated Oct. 12, 2010, 14 pgs.
Palmer, Biff, F., M.D., Managing Hyperkalemia Caused by Inhibitors of the Renin-Angiotensin-Aldosterone System, Aug. 5, 2004, The New England Journal of Medicine 2004, vol. 351;6, 2004 Massachusetts Medical Society, pp. 585-592.
Pappone, Carlo et al., [2004][759] Pulmonary Vein Denervation Benefits Paroxysmal Atrial Fibrillation Patients after Circumferential Ablation, Abstract only. 1 page, Jan. 5, 2004.
Ram, C. Venkata S., M.D., Understanding refractory hypertension, May 15, 2004, Patient Care May 2004, vol. 38, pp. 12-16, 7 pages from http://www.patientcareonline.com/patcare/content/printContentPopup.jsp?id=108324.
Renal Parenchymal Disease, Ch. 26, 5th Edition Heart Disease, A Textbook of Cardiovascular Medicine vol. 2, Edited by Eugene Braunwald, WB Saunders Company, pp. 824-825 1997.
Roth, Bradley J. and Peter J. Basser, A Model of the Stimulation of a Nerve Fiber by Electromagnetic Induction, IEEE Transactions on Biomedical Engineering, vol. 37, No. 6, Jun. 1990, pp. 588-597.
Rudin, Asa, M.D. et al., Postoperative Epidural or Intravenous Analgesia after Major Abdominal or Thoraco-Abdominal Surgery, The Journal of the American Society of Anesthesiologists, Inc., Anesthesiology 2001, vol. 95, A-970, 1 page.
Search Report dated Oct. 17, 2013 for European Application No. 13159256.
Schauerte, P et al., Catheter ablation of cardiac autonomic nerves for prevention of vagal atrial fibrillation, Circulation. 102(22). Nov. 28, 2000. Abstract only. 2 pgs.
Shupak, Naomi M., Therapeutic Uses of Pulsed Magnetic-Field Exposure: A Review, Radio Science Bulletin Dec. 2003, No. 307, pp. 9-32.
Siegel, RJ et al., Clinical demonstration that catheter-delivered ultrasound energy reverses arterial vasoconstriction, Journal of the American College of Cardiology. 1992. 20; 732-735. Summary only. 2 pgs.
Smithwick, R.H. et al., Hypertension and associated cardiovascular disease: comparison of male and female mortality rates and their influence on selection of therapy, JAMA, 1956, 160:1023-1033.
Terashima, Mitsuyasu et al. Feasibility and Safety of a Novel CryoPlasty™ System. Poster. 1 page, Mar. 15, 2002.
The Antihypertensive and Lipid-Lowering Treatment to Prevent Heart Attack Trial, ALLHAT Research Group, JAMA, 2002, vol. 288, pp. 2981-2997.
Trock, David H. et al., The Effect of Pulsed Electromagnetic Fields in the Treatment of Osteoarthritis of the Knee and Cervical Spine. Report of Randomized, Double Blind, Placebo Controlled Trials, Mar. 22, 1994, The Journal of Rheumatology 1994, vol. 21, pp. 1903-1911.
Van Antwerp, Bill and Poonam Gulati, Protein Delivery from Mechanical Devices Challenges and Opportunities, Medtronic presentation, 19 pages, Jul. 2003.
Wolinsky, Harvey, M.D. PhD and Swan N. Thung, M.D., Use of a Perforated Balloon Catheter to Deliver Concentrated Heparin Into the Wall of the Normal Canine Artery, Aug. 30, 1989, JACC 1990, vol. 15, 1990 by the American College of Cardiology, pp. 475-481.

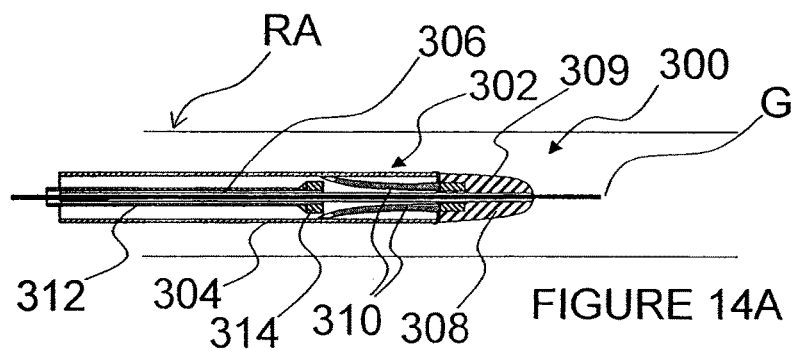
FIGURE 14A
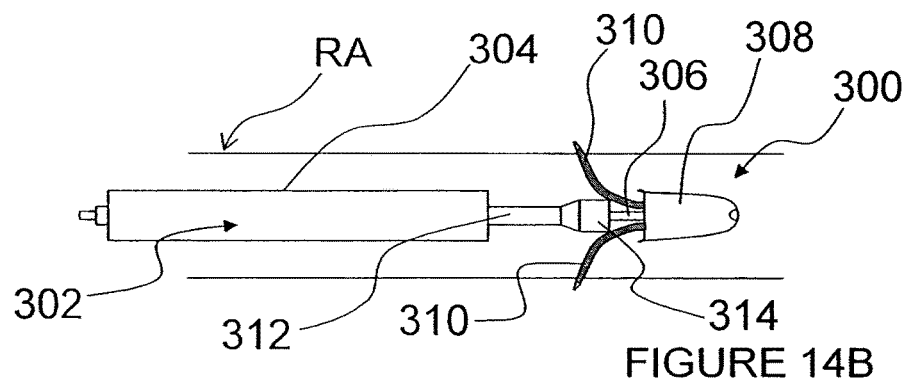
FIGURE 14B
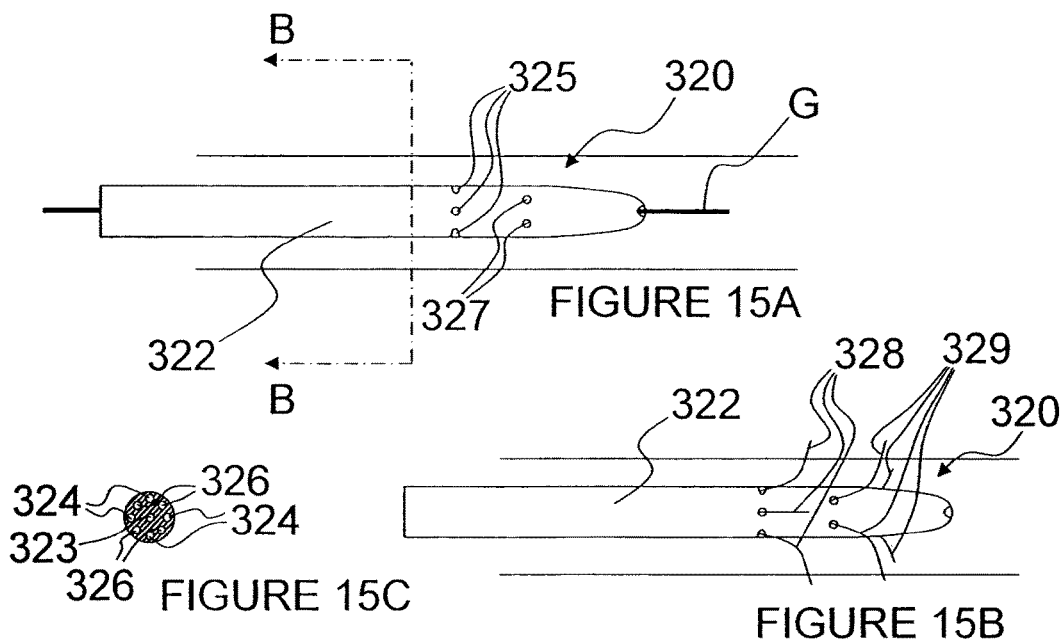
FIGURE 15A
FIGURE 15B
FIGURE 15C

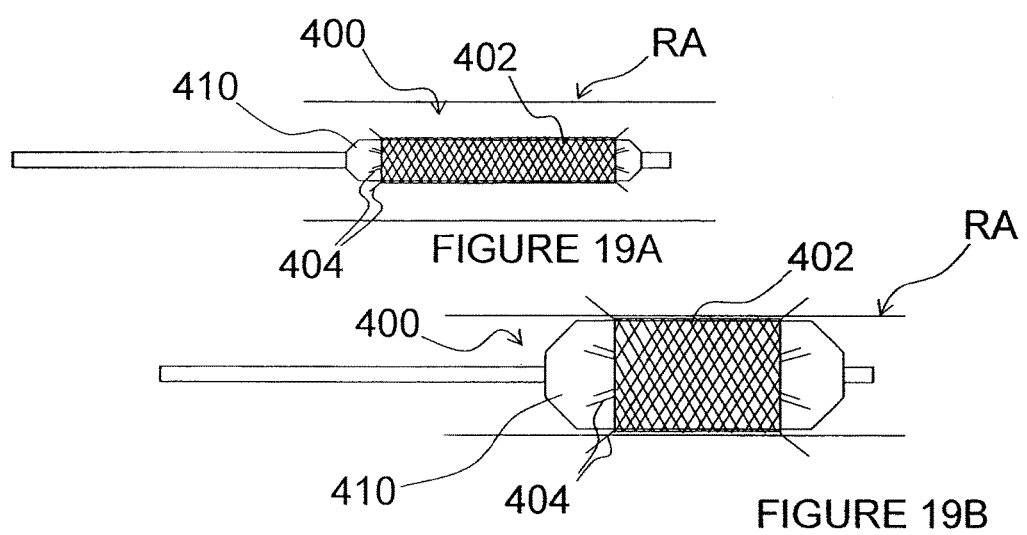

APPARATUS FOR RENAL NEUROMODULATION VIA AN INTRA-TO-EXTRAVASCULAR APPROACH

CROSS REFERENCE TO RELATED APPLICATIONS

The present application is a continuation of U.S. patent application Ser. No. 14/574,262, filed Dec. 17, 2014, now U.S. Pat. No. 9,364,280, which is a Division of U.S. patent application Ser. No. 13/007,370, filed Jan. 14, 2011, now U.S. Pat. No. 8,958,871, which is a continuation of U.S. patent application Ser. No. 12/616,708, filed Nov. 11, 2009, now U.S. Pat. No. 7,873,417, which is a continuation of U.S. patent application Ser. No. 11/363,867, filed Feb. 27, 2006, now U.S. Pat. No. 7,620,451, which claims the benefit of U.S. Provisional Application No. 60/813,589, filed on Dec. 29, 2005, the disclosures of which are incorporated herein by reference in their entirety.

U.S. patent application Ser. No. 11/363,867, now U.S. Pat. No. 7,620,451, is also a continuation-in-part of each of the following U.S. Patent Applications:

(a) U.S. patent application Ser. No. 11/129,765, filed on May 13, 2005, now U.S. Pat. No. 7,653,438, which claims the benefit of U.S. Provisional Application No. 60/616,254, filed on Oct. 5, 2004; and 60/624,793, filed on Nov. 2, 2004. Further, this application is a continuation-in-part of U.S. patent application Ser. No. 10/408,665, filed on Apr. 8, 2003, now U.S. Pat. No. 7,162,303, which claims the benefit of U.S. Provisional Patent Application Nos. 60/442,970, filed on Jan. 29, 2003; 60/415,575, filed on Oct. 3, 2002; and 60/370,190, filed on Apr. 8, 2002.

(b) U.S. patent application Ser. No. 11/189,563, filed on Jul. 25, 2005, now U.S. Pat. No. 8,145,316.

(c) U.S. patent application Ser. No. 11/266,993, filed on Nov. 4, 2005, now U.S. Pat. No. 7,756,583.

INCORPORATION BY REFERENCE

All publications and patent applications mentioned in this specification are herein incorporated by reference to the same extent as if each individual publication or patent application was specifically and individually indicated to be incorporated by reference.

TECHNICAL FIELD

The present invention relates to methods and apparatus for neuromodulation. More particularly, the present invention relates to methods and apparatus for achieving pulsed electric field neuromodulation via an intra-to-extravascular approach.

BACKGROUND

Congestive Heart Failure ("CHF") is a condition that occurs when the heart becomes damaged and reduces blood flow to the organs of the body. If blood flow decreases sufficiently, kidney function becomes impaired, which results in fluid retention, abnormal hormone secretions and increased constriction of blood vessels. These results increase the workload of the heart and further decrease the capacity of the heart to pump blood through the kidneys and circulatory system.

It is believed that progressively decreasing perfusion of the kidneys is a principal non-cardiac cause perpetuating the downward spiral of CHF. Moreover, the fluid overload and associated clinical symptoms resulting from these physiologic changes result in additional hospital admissions, poor quality of life and additional costs to the health care system.

In addition to their role in the progression of CHF, the kidneys play a significant role in the progression of Chronic Renal Failure ("CRF"), End-Stage Renal Disease ("ESRD"), hypertension (pathologically high blood pressure) and other cardio-renal diseases. The functions of the kidneys can be summarized under three broad categories: filtering blood and excreting waste products generated by the body's metabolism; regulating salt, water, electrolyte and acid-base balance; and secreting hormones to maintain vital organ blood flow. Without properly functioning kidneys, a patient will suffer water retention, reduced urine flow and an accumulation of waste toxins in the blood and body. These conditions result from reduced renal function or renal failure (kidney failure) and are believed to increase the workload of the heart. In a CHF patient, renal failure will cause the heart to further deteriorate as fluids are retained and blood toxins accumulate due to the poorly functioning kidneys.

It has been established in animal models that the heart failure condition results in abnormally high sympathetic activation of the kidneys. An increase in renal sympathetic nerve activity leads to vasoconstriction of blood vessels supplying the kidneys, decreased renal blood flow, decreased removal of water and sodium from the body, and increased renin secretion. Reduction of sympathetic renal nerve activity, e.g., via denervation, may reverse these processes.

Applicants have previously described methods and apparatus for treating renal disorders by applying a pulsed electric field to neural fibers that contribute to renal function. See, for example, co-pending U.S. patent application Ser. No. 11/129,765, filed on May 13, 2005, and Ser. No. 11/189,563, filed on Jul. 25, 2005, both of which are incorporated herein by reference in their entireties. A pulsed electric field ("PEF") may initiate renal neuromodulation, e.g., denervation, for example, via irreversible electroporation or via electrofusion. The PEF may be delivered from apparatus positioned intravascularly, extravascularly, intra-to-extravascularly or a combination thereof. As used herein, electrofusion comprises fusion of neighboring cells induced by exposure to an electric field. Contact between target neighboring cells for the purposes of electrofusion may be achieved in a variety of ways, including, for example, via dielectrophoresis. In tissue, the target cells may already be in contact, thus facilitating electrofusion.

As used herein, electroporation and electropermeabilization are methods of manipulating the cell membrane or intracellular apparatus. For example, the porosity of a cell membrane may be increased by inducing a sufficient voltage across the cell membrane through, e.g., short, high-voltage pulses. The extent of porosity in the cell membrane (e.g., size and number of pores) and the duration of effect (e.g., temporary or permanent) are a function of multiple variables, such as field strength, pulse width, duty cycle, electric field orientation, cell type or size and other parameters.

Cell membrane pores will generally close spontaneously upon termination of relatively lower strength electric fields or relatively shorter pulse widths (herein defined as "reversible electroporation"). However, each cell or cell type has a critical threshold above which pores do not close such that pore formation is no longer reversible; this result is defined as "irreversible electroporation," "irreversible breakdown" or "irreversible damage." At this point, the cell membrane ruptures and/or irreversible chemical imbalances caused by the high porosity occur. Such high porosity can be the result of a single large hole and/or a plurality of smaller holes.

In some patients, when a PEF sufficient to initiate irreversible electroporation is applied to renal nerves and/or other neural fibers that contribute to renal neural functions, applicants believe that denervation induced by the PEF would result in increased urine output, decreased plasma renin levels, decreased tissue (e.g., kidney) and/or urine catecholamines (e.g., norepinephrine), increased urinary sodium excretion, and/or controlled blood pressure that would prevent or treat CHF, hypertension, renal system diseases, and other renal or cardio-renal anomalies. PEF systems could be used to modulate efferent or afferent nerve signals, as well as combinations of efferent and afferent nerve signals.

A potential challenge of using intravascular PEF systems for treating renal disorders is to selectively electroporate target cells without affecting other cells. For example, it may be desirable to irreversibly electroporate renal nerve cells that travel along or in proximity to renal vasculature, but it may not be desirable to damage the smooth muscle cells of which the vasculature is composed. As a result, an overly aggressive course of PEF therapy may persistently injure the renal vasculature, but an overly conservative course of PEF therapy may not achieve the desired renal neuromodulation.

Applicants have previously described methods and apparatus for monitoring tissue impedance or conductivity to determine the effects of pulsed electric field therapy, e.g., to determine an extent of electroporation and/or its degree of irreversibility. See, for example, Applicant's co-pending U.S. patent application Ser. No. 11/233,814, filed Sep. 23, 2005, which is incorporated herein by reference in its entirety. Pulsed electric field electroporation of tissue causes a decrease in tissue impedance and an increase in tissue conductivity. If induced electroporation is reversible, tissue impedance and conductivity should approximate baseline levels upon cessation of the pulsed electric field. However, if electroporation is irreversible, impedance and conductivity changes should persist after terminating the pulsed electric field. Thus, monitoring the impedance or conductivity of target and/or non-target tissue may be utilized to determine the onset of electroporation and to determine the type or extent of electroporation. Furthermore, monitoring data may be used in one or more manual or automatic feedback loops to control the electroporation.

Regardless of whether or not monitoring techniques are utilized, the applied energy or voltage from an intravascular PEF system necessary to establish an electric field of sufficient magnitude in the vicinity of target neural fibers in order to modulate the target neural fibers may be of a magnitude that causes persistent damage to non-target tissue, such as smooth muscle cells of the vessel wall. Thus, a desired treatment outcome, e.g., renal denervation, may not be achievable with some intravascular PEF systems in certain patients without concomitantly inducing persistent damage to the non-target tissue. It therefore would be desirable to provide methods and apparatus for reducing the required magnitude of applied energy or voltage necessary to achieve desired neuromodulation in target tissue and/or to increase localization of the sufficient magnitude induced electric field to the vicinity of the target tissue.

SUMMARY

The present invention provides methods and apparatus for pulsed electric field ("PEF") neuromodulation via an intra-to-extravascular ("ITEV") approach, e.g., to effectuate irreversible electroporation or electrofusion, necrosis and/or inducement of apoptosis, alteration of gene expression, changes in cytokine upregulation, and other conditions in target neural fibers. In some embodiments, the ITEV PEF system comprises an intravascular catheter having one or more electrodes configured for intra-to-extravascular placement across a wall of a patient's vessel into proximity with target neural fibers. With the electrode(s) passing from an intravascular position to an extravascular position prior to delivery of the PEF, a magnitude of applied voltage or energy delivered via the electrode(s) and necessary to achieve desired neuromodulation may be reduced relative to an intravascular PEF system having one or more electrodes positioned solely intravascularly. The methods and apparatus of the present invention may, for example, be used to modulate one or more target neural fibers that contribute to renal function.

Pulsed electric field parameters may be altered and combined in any combination, as desired. Such parameters can include, but are not limited to, voltage, field strength, pulse width, pulse duration, the shape of the pulse, the number of pulses and/or the interval between pulses (e.g., duty cycle), etc. For example, suitable field strengths can be up to about 10,000 V/cm and suitable pulse widths can be up to about 1 second. Suitable shapes of the pulse waveform include, for example, AC waveforms, sinusoidal waves, cosine waves, combinations of sine and cosine waves, DC waveforms, DC-shifted AC waveforms, RF waveforms, square waves, trapezoidal waves, exponentially-decaying waves, or combinations. The field includes at least one pulse, and in many applications the field includes a plurality of pulses. Suitable pulse intervals include, for example, intervals less than about 10 seconds. These parameters are provided as suitable examples and in no way should be considered limiting.

BRIEF DESCRIPTION OF THE DRAWINGS

Several embodiments of the present invention will be apparent upon consideration of the following detailed description, taken in conjunction with the accompanying drawings, in which like reference characters refer to like parts throughout, and in which:

FIGS. 14A-14D are schematic side-sectional views and schematic side-views, partially in section, illustrating alternative methods and apparatus for pulsed electric field neuromodulation via electrodes positioned extravascularly via an intra-to-extravascular approach.

FIGS. 15A-15C are schematic side-views, partially in section, as well as a cross-sectional view along section line B-B of FIG. 15A, of further alternative methods and apparatus for pulsed electric field neuromodulation via electrodes positioned extravascularly via an intra-to-extravascular approach.

FIGS. 19A and 19B are schematic side-views, partially in section, of methods and apparatus for pulsed electric field neuromodulation comprising a stent having electrodes configured for intra-to-extravascular placement.

DETAILED DESCRIPTION

A. Overview

The present invention relates to methods and apparatus for neuromodulation, e.g., denervation. More particularly, the present invention relates to methods and apparatus for achieving pulsed electric field neuromodulation via an intravascular-to-extravascular approach. In some embodiments, the ITEV PEF system comprises an intravascular catheter having one or more electrodes configured for intra-to-extravascular placement across a wall of patient's vessel into proximity with target neural fibers. With the electrode(s) passing from an intravascular position to an extravascular position prior to delivery of the PEF, a magnitude of applied voltage or energy delivered via the electrode(s) and necessary to achieve desired neuromodulation is reduced relative to an intravascular PEF system having one or more electrodes positioned solely intravascularly. The methods and apparatus of the present invention may, for example, be used to modulate one or more target neural fibers that contribute to renal function.

The methods and apparatus of the present invention may be used to modulate a neural fiber that contributes to renal function and may exploit any suitable electrical signal or field parameters, e.g., any electric field that will achieve the desired neuromodulation (e.g., electroporative effect). To better understand the structures of devices of the present invention and the methods of using such devices for renal neuromodulation and monitoring, it is instructive to examine the renal anatomy in humans.

B. Selected Embodiments of Methods for Neuromodulation

Figure 1:
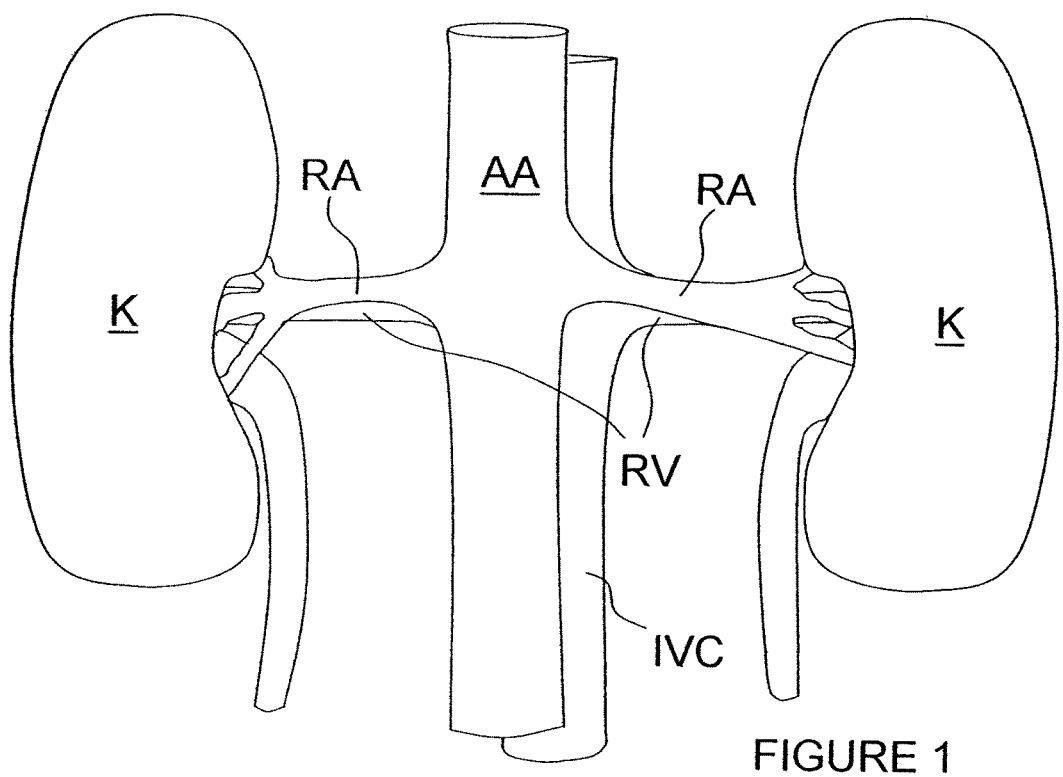
FIG. 1 is a schematic view illustrating human renal anatomy.
Figure 2:
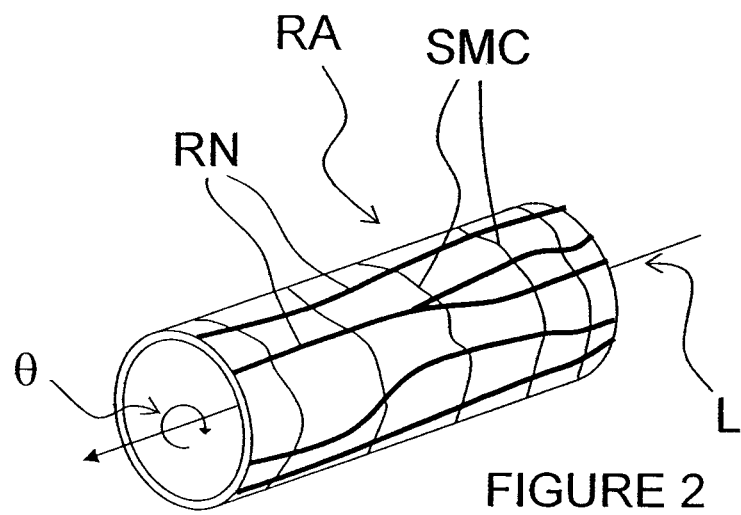
FIG. 2 is a schematic detail view showing the location of the renal nerves relative to the renal artery.

With reference now to FIG. 1, the human renal anatomy includes kidneys K that are supplied with oxygenated blood by renal arteries RA, which are connected to the heart by the abdominal aorta AA. Deoxygenated blood flows from the kidneys to the heart via renal veins RV and the inferior vena cava IVC. FIG. 2 illustrates a portion of the renal anatomy in greater detail. More specifically, the renal anatomy also includes renal nerves RN extending longitudinally along the lengthwise dimension L of renal artery RA generally within the adventitia of the artery. The renal artery RA has smooth muscle cells SMC that surround the arterial circumference and spiral around the angular axis θ of the artery. The smooth muscle cells of the renal artery accordingly have a lengthwise or longer dimension extending transverse (i.e., non-parallel) to the lengthwise dimension of the renal artery. The misalignment of the lengthwise dimensions of the renal nerves and the smooth muscle cells is defined as "cellular misalignment."

Figure 3A:
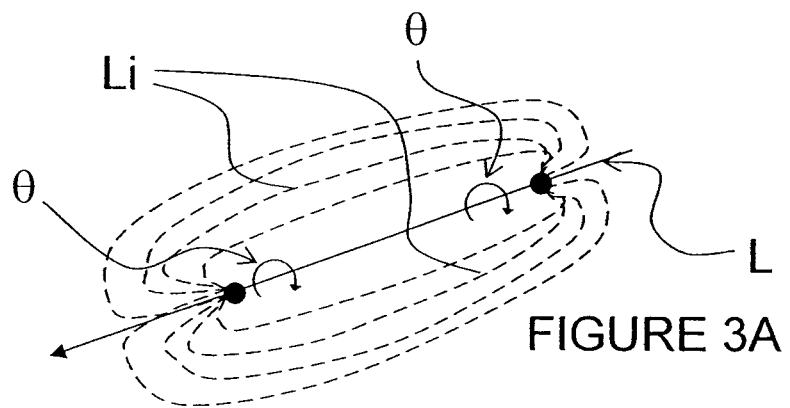
FIGS. 3A and 3B are schematic side- and end-views, respectively, illustrating orienting of an electric field for selectively affecting renal nerves.
Figure 3B:
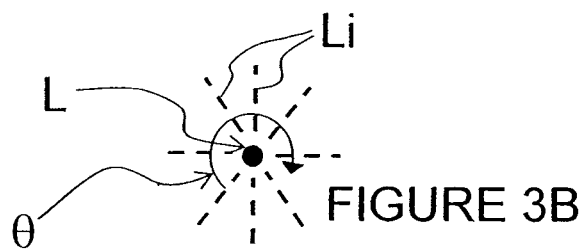

Referring to FIG. 3, the cellular misalignment of the renal nerves and the smooth muscle cells may be exploited to selectively affect renal nerve cells with reduced effect on smooth muscle cells. More specifically, because larger cells require a lower electric field strength to exceed the cell membrane irreversibility threshold voltage or energy for irreversible electroporation, embodiments of electrodes of the present invention may be configured to align at least a portion of an electric field generated by the electrodes with or near the longer dimensions of the cells to be affected. In specific embodiments, the device has electrodes configured to create an electrical field aligned with or near the lengthwise dimension L of the renal artery RA to affect renal nerves RN. By aligning an electric field so that the field preferentially aligns with the lengthwise aspect of the cell rather than the diametric or radial aspect of the cell, lower field strengths may be used to affect target neural cells, e.g., to necrose or fuse the target cells, to induce apoptosis, to alter gene expression, to change cytokine upregulation, and/or to induce other suitable processes. This is expected to reduce total energy delivered to the system and to mitigate effects on non-target cells in the electric field.

Similarly, the lengthwise or longer dimensions of tissues overlying or underlying the target nerve are orthogonal or otherwise off-axis (e.g., transverse) with respect to the longer dimensions of the nerve cells. Thus, in addition to aligning the PEF with the lengthwise or longer dimensions of the target cells, the PEF may propagate along the lateral or shorter dimensions of the non-target cells (i.e., such that the PEF propagates at least partially out of alignment with non-target smooth muscle cells SMC). Therefore, as seen in FIG. 3, applying a PEF with propagation lines Li generally aligned with the longitudinal dimension L of the renal artery RA is expected to preferentially cause electroporation, electrofusion, denervation or other neuromodulation in cells of the target renal nerves RN without unduly affecting the non-target arterial smooth muscle cells SMC. The pulsed electric field may propagate in a single plane along the longitudinal axis of the renal artery, or may propagate in the longitudinal direction along any angular segment 8 through a range of 0°-360°.

A PEF system placed within and/or at least partially across the wall of the renal artery, e.g., via an intra-to-extravascular ("ITEV") approach, may propagate an electric field having a longitudinal portion that is aligned to run with the longitudinal dimension of the artery in the region of the renal nerves RN and the smooth muscle cell SMC of the vessel wall so that the wall of the artery remains at least substantially intact while the outer nerve cells are destroyed, fused or otherwise affected. Monitoring elements may be utilized to assess an extent of, e.g., electroporation, induced in renal nerves and/or in smooth muscle cells, as well as to adjust PEF parameters to achieve a desired effect.

C. Exemplary Embodiments of Systems and Additional Methods for Neuromodulation

With reference to FIG. 4, embodiments of intra-to-extravascular ("ITEV") PEF systems and methods of the present invention are described. ITEV PEF systems of the present invention are configured for temporary intravascular placement and for passage of one or more electrodes across a wall of the vasculature for extravascular placement. Furthermore, the systems are configured to deliver pulsed electric fields to neural fibers for neuromodulation. In one particular example, the systems are configured to deliver the pulsed electric fields to neural fibers that contribute to renal function in order to achieve renal neuromodulation. For the purposes of the present invention, extravascular shall refer to any position external to the intima and media layers of the vasculature. Extravascular may, for example, include positions within the adventitia of the vessel or within surrounding fatty tissue.

In FIGS. 4A-D, an ITEV PEF system 100 comprises an intravascular catheter 102 having a lumen 103, a shaped cannula 104 configured for low-profile delivery within the lumen 103 and for advancement from the lumen 103 in order to pierce the wall of a patient's vasculature, and a first guide wire electrode 106 configured for advancement through a lumen 105 of the cannula 104. The cannula 104 may, for example, be fabricated from a shape memory material (e.g., Nitinol) or a flexible, pre-formed elastic material (e.g., thin-walled stainless steel).

Figure 4A:
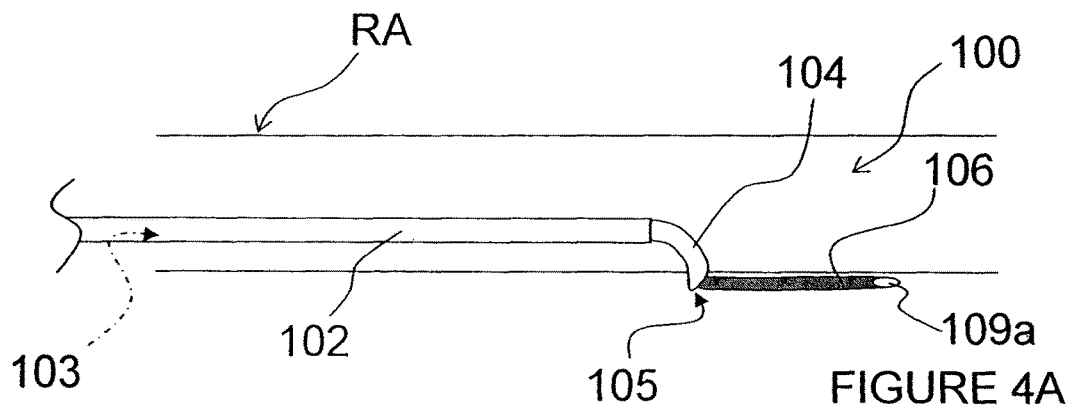
FIGS. 4A-4D are schematic side-views, partially in section, illustrating methods and apparatus for pulsed electric field neuromodulation via an intra-to-extravascular approach having a bipolar electrode pair with at least one of the electrodes of the pair positioned extravascularly.
Figure 4B:
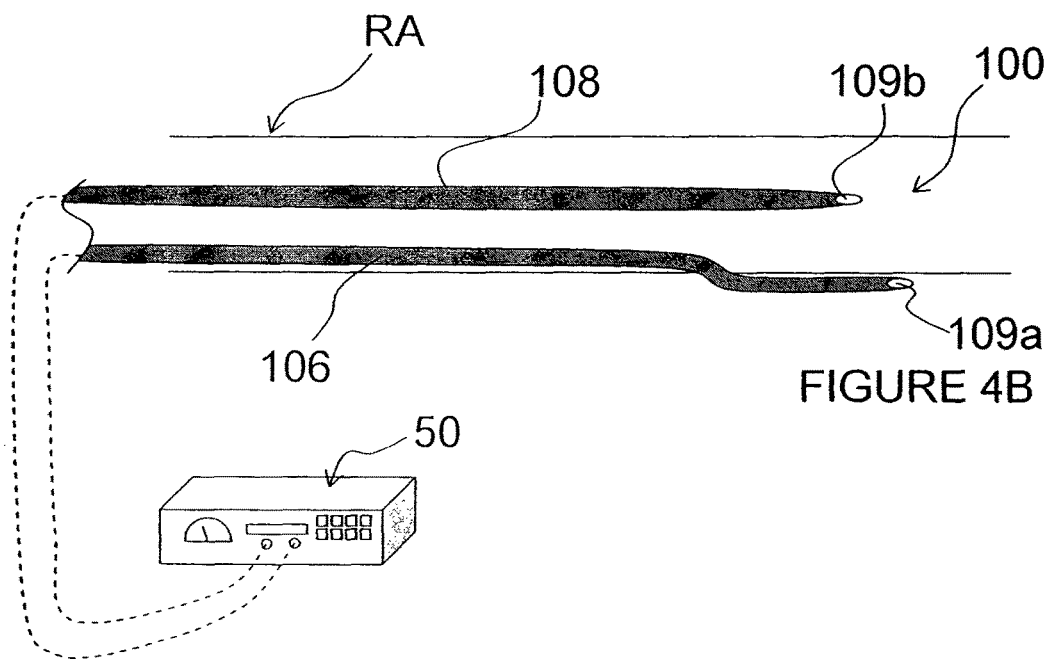

In the embodiment of FIGS. 4A and 4B, system 100 further comprises a second guide wire electrode 108 (FIG. 4B) configured for intravascular positioning. The guide wire electrodes 106 and 108, which form a bipolar electrode pair, optionally may be insulated at all regions, except their distal ends. The electrodes are electrically connected to a pulsed electric field generator 50 (FIG. 4B) located external to the patient. The generator may be utilized with any embodiment of the present invention to deliver a PEF with desired field parameters. It should be understood that several examples of PEF-delivery electrodes described below may be electrically connected to the generator even though the generator is not explicitly shown or described with each embodiment.

In use, the catheter 102 may be delivered to renal artery RA as shown in FIG. 4A, or it may be delivered through a guide catheter or other device to a renal vein or to any other vessel in proximity to target neural tissue (e.g., target neural tissue that contributes to renal function). The catheter preferably is delivered via a percutaneous technique, such as via a percutaneous femoral artery access. Once the shaped cannula 104 is positioned within the patient's vasculature, it may be advanced past the outlet of the lumen 103 of the catheter 102 such that the cannula 104 assumes a curved or otherwise angular profile. As the cannula 104 advances further, it pierces the wall of the patient's vasculature to be positioned extravascularly (i.e., at least within the adventitia). The first guide wire electrode 106 is then advanced through the cannula lumen 105 such that a non-insulated distal region 109a of the first electrode 106 is positioned extravascularly via an intra-to-extravascular approach. The cannula 104 may be retracted, and the catheter 102, as well as the cannula 104 may be removed from the patient or from the treatment site. The second guide wire electrode 108 has a non-insulated distal region 109b that is positioned intravascularly (before, during or after extravascular placement of the first electrode 106) to form a bipolar electrode pair with the first electrode 106 (FIG. 4B).

The first electrode 106 preferably comprises the active electrode and the second electrode 108 preferably comprises the return electrode. However, it should be understood that the electrode polarities optionally may be reversed. The non-insulated distal regions 109a-b of the electrodes 106 and 108 optionally may be in substantial alignment along a cross-sectional plane through renal artery RA. Alternatively, the distal regions 109a-b may be spaced apart longitudinally. Such longitudinal spacing of the distal regions 109a-b may, for example, better align a pulsed electric field delivered across the electrodes with a longitudinal dimension of the renal artery to facilitate modulation of renal nerves with limited effect on non-target smooth muscle cells or other cells, as described previously with respect to FIG. 3.

With the first and second electrodes 106 and 108 positioned as desired, a pulsed electric field generated by the PEF generator 50 is transmitted through the electrodes 106 and 108 and delivered across the non-insulated distal regions 109a-b of the electrodes. The PEF therapy modulates activity along neural fibers that directly or indirectly contribute to renal function (e.g., denervates neural fibers related to renal function). This may be achieved, for example, via irreversible electroporation, electrofusion, necrosis and/or inducement of apoptosis in the nerve cells, alteration of gene expression, changes in cytokine upregulation, and/or other suitable processes. After delivery of PEF therapy, the ITEV PEF system 100 may be removed from the patient to conclude the procedure.

It is expected that PEF therapy using the ITEV PEF system 100 will alleviate clinical symptoms of CHF, hypertension, renal disease and/or other cardio-renal diseases for a period of months, potentially up to six months or more. This time period might be sufficient to allow the body to heal; for example, this period might reduce the risk of CHF onset after an acute myocardial infarction, thereby alleviating a need for subsequent re-treatment. Alternatively, as symptoms reoccur, or at regularly scheduled intervals, the patient might return to the physician for a repeat therapy.

In order to denervate or otherwise modulate target neural fibers, the ITEV PEF system 100 should generate an electric field of sufficient strength or magnitude across the fibers to induce such denervation or modulation. When utilizing an intravascular PEF system, depending upon the arrangement and positioning of the PEF electrodes, as well as the physiology of the patient, the applied voltage necessary to achieve a field strength of sufficient magnitude at the target neural fibers also may be of sufficient magnitude to induce undesirable persistent injury in non-target tissue, such as smooth muscle cells and/or the vessel wall. It is expected that the extravascular positioning of electrode 106 via an intra-to-extravascular approach will reduce the necessary applied voltage for denervation or modulation (e.g., renal denervation or modulation) via PEF therapy compared to the applied voltage required when utilizing solely intravascular apparatus with similarly spaced and sized electrodes. Specifically, extravascular placement of electrode 106 in closer proximity to the target neural fibers is expected to increase localization of the peak induced electric field to the vicinity of the target neural fibers.

Figure 4C:
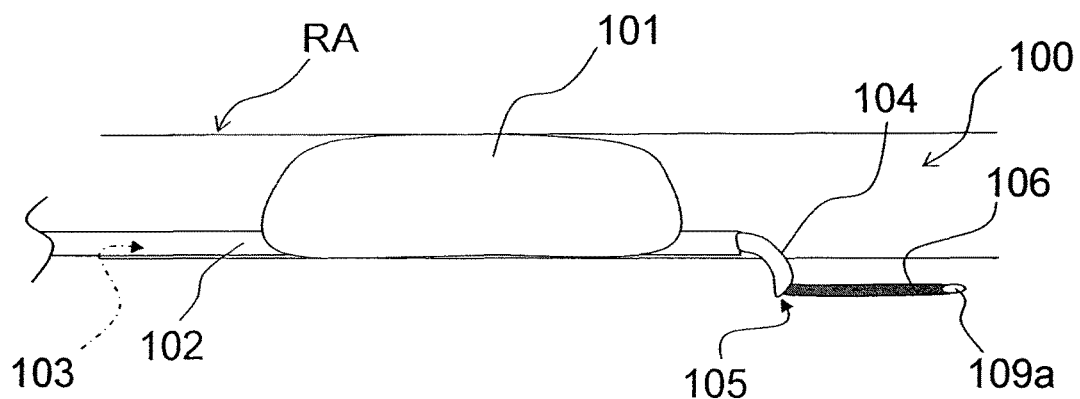
Figure 4D:
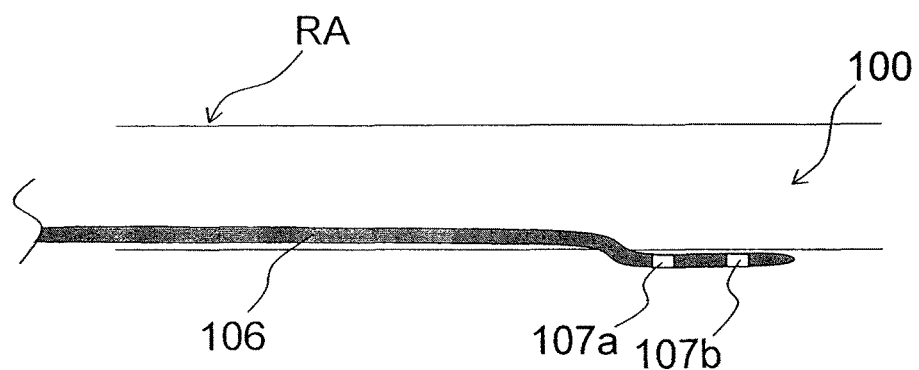

As seen in FIG. 4C, the catheter 102 optionally may comprise an expandable element 101 (e.g., an inflatable balloon) that stabilizes the catheter 102 within the patient's vessel. The expandable element 101 further facilitates piercing of the vessel wall with the cannula 104 to position the first electrode 106 at an extravascular location. As seen in FIG. 4D, the first electrode 106 may comprise a spaced bipolar electrode pair 107a and 107b to obviate the need for the intravascular second electrode 108. The PEF therapy may be delivered extravascularly across the bipolar electrode pair 107a-b.

The extravascular second electrode 106 optionally may be replaced with a virtual electrode. For example, conductive saline may be injected through cannula 104 into the extravascular space. The conductive saline may provide a virtual electrode surrounding all or part of the circumference of the vessel and may be used in a bipolar fashion with intravascular electrode 108.

Figure 5:
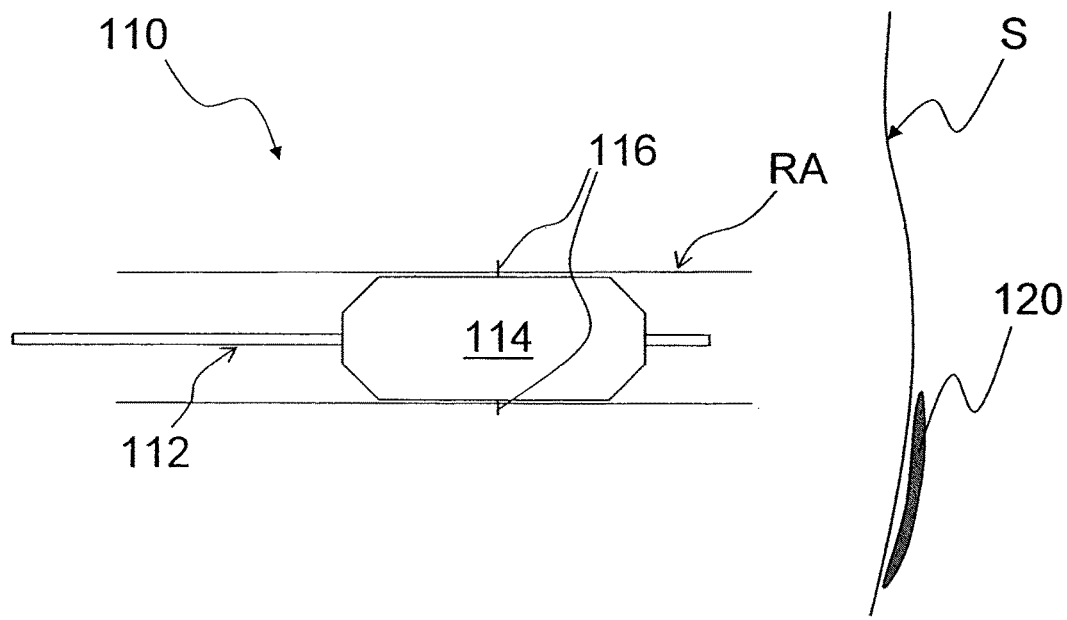
FIG. 5 is a schematic view, partially in section, illustrating methods and apparatus for monopolar pulsed electric field neuromodulation via an intra-to-extravascular approach.

The examples of the ITEV PEF systems of FIGS. 4A-D optionally may be utilized in a monopolar fashion by replacing the intravascular second electrode 108 with a ground pad coupled to the PEF generator 50 and attached to the exterior of the patient. FIG. 5 illustrates an alternative monopolar ITEV PEF system 110 comprising a catheter 112 having an expandable element 114 with one or more needle-like ITEV electrodes 116 coupled to the expandable element. When multiple needle electrodes 116 are provided, they may be spaced circumferentially and/or longitudinally about/along the expandable element 114. The system 110 further comprises a ground pad 120 attached to the skin S of the patient along the exterior of the patient (e.g., to the patient's flank, back or thigh) and coupled to the PEF generator 50 as a return electrode. The ground pad 120 optionally may be positioned directly lateral to the ITEV electrode(s) 116 to direct the PEF therapy along the patient's vasculature (e.g., along renal artery RA).

The expandable element 114 comprises a member or structure configured for intravascular delivery to (and retrieval from) a target location in a low profile configuration and for expansion to an expanded deployed configuration at the target location. The expandable element 114 may comprise, for example, an inflatable balloon, an expandable basket or cage, or other expandable structure. As seen in FIG. 5, expansion of the expansion element 114 causes the ITEV electrode(s) 116 to pierce the wall of renal artery RA and move from an intravascular location to an extravascular location. With the ITEV electrode(s) 116 positioned extravascularly and coupled to the PEF generator 50, the ITEV electrode(s) may be energized as active electrodes in a monopolar PEF therapy with the external ground pad 120 serving as the return electrode.

Figure 6A:
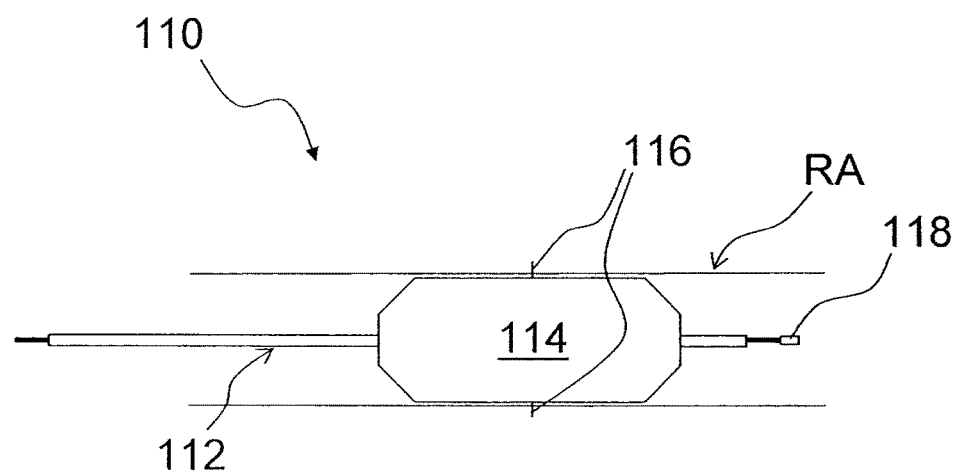
FIGS. 6A-6C are schematic side-views, partially in section, illustrating alternative embodiments of the methods and apparatus of FIG. 5, the methods and apparatus comprising a bipolar electrode pair having a first electrode positioned extravascularly and a second electrode positioned intravascularly.
Figure 6B:
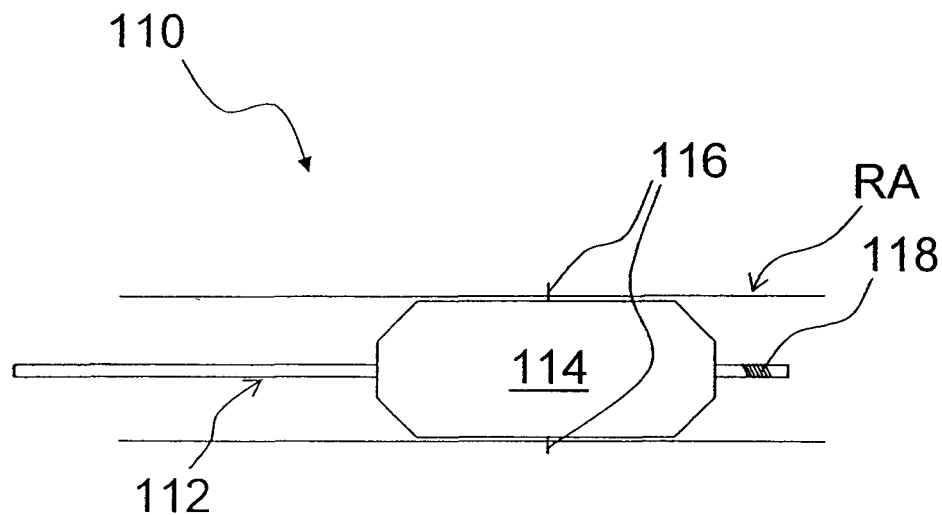
Figure 6C:
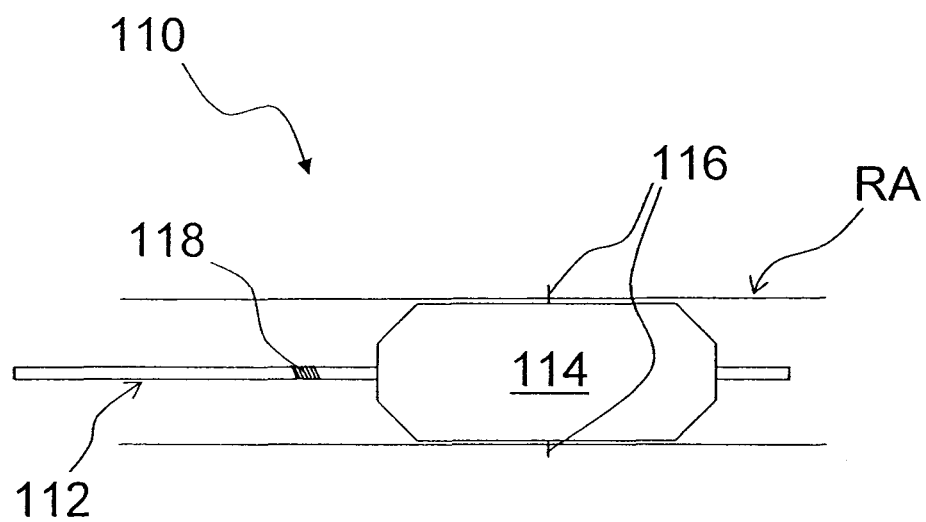

Referring now to FIGS. 6A-C, alternative embodiments of the ITEV PEF system 110 are described comprising a first electrode positioned extravascularly and a second electrode positioned intravascularly. In FIGS. 6A-C, the ITEV PEF systems 110 again comprise the catheter 112 having the expandable element 114 with one or more ITEV electrodes 116 coupled to the expandable element and configured for intra-to-extravascular delivery. The systems 110 further comprise an intravascular second electrode 118 positioned within the vessel. In FIG. 6A, the second electrode 118 comprises a guidewire electrode positioned within the lumen of the catheter 112. The guidewire electrode 118 is coupled to the PEF generator 50 and is insulated at regions other than a distal region positioned distal of the catheter 112. In FIG. 6B, the second electrode 118 is coupled to the shaft of the catheter 112 distally of the expandable element 114. In FIG. 6C, the second electrode 118 is coupled to the shaft of catheter 112 proximally of the expandable element 114. In use, the ITEV electrode(s) 116 may comprise active electrode(s) and the second electrode 118 may comprise a return electrode, or vice versa. The second electrode 118 optionally may be longitudinally spaced relative to the ITEV electrode(s) 116 to align the PEF therapy with a longitudinal axis of the patient's vasculature, as described previously with respect to FIGS. 2 and 3. The second electrodes 118 may, for example, be fabricated from wound coils of wire. When utilizing relatively long electrodes, wound coils allow the catheter 112 to maintain desired flexibility.

Figure 7A:
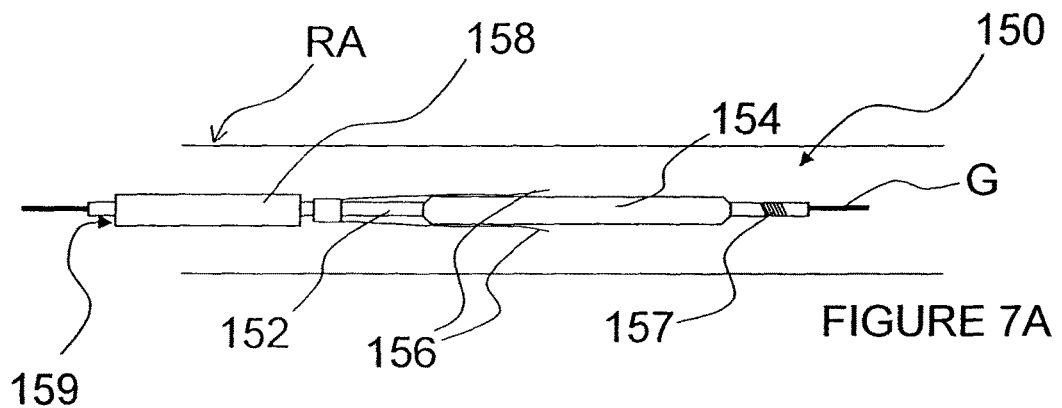
FIGS. 7A and 7B are schematic side-views, partially in section, illustrating additional methods and apparatus for pulsed electric field neuromodulation via a bipolar electrode pair, the bipolar electrode pair comprising at least one first electrode positioned extravascularly and at least one second electrode positioned intravascularly.
Figure 7B:
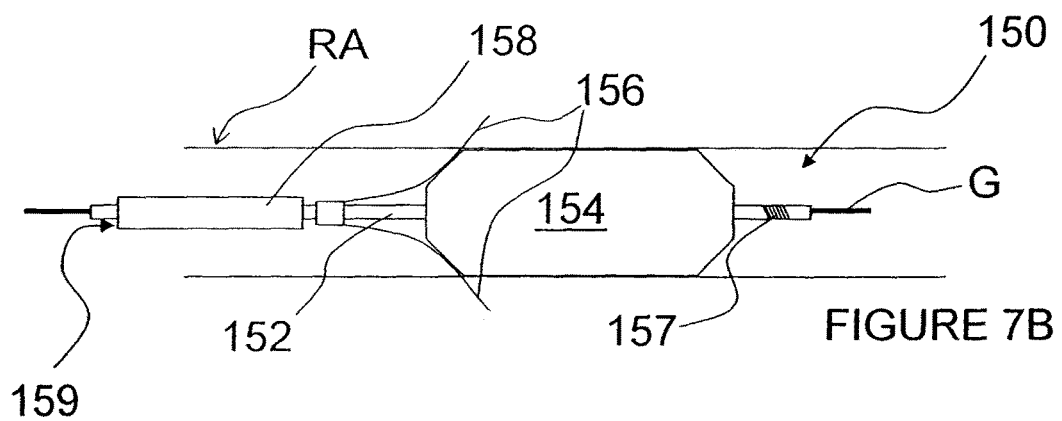

Referring now to FIGS. 7A and 7B, additional methods and apparatus for pulsed electric field neuromodulation via a bipolar electrode pair having a first electrode positioned extravascularly and a second electrode positioned intravascularly are described. FIGS. 7A and 7B, more specifically, illustrate an ITEV PEF system 150 comprising a catheter 152 and an expandable element 154, which may comprise an inflatable balloon or an expandable wire cage. The system 150 further comprises one or more ITEV needle electrodes 156 that are coupled to the catheter 152, illustratively proximal of expandable element 154, and return electrode 157, illustratively coupled to the shaft of catheter 152 distal of expandable element 154. Additionally, the system comprises a protective sheath 158 having a lumen 159 in which the catheter 152 may be positioned for percutaneous advancement and/or retrieval.

In FIGS. 7A and 7B, the distal regions of the ITEV electrodes 156 extend laterally over, but are not connected to, at least a portion of the expandable element 154. This is in contrast to the previously described ITEV PEF systems of FIGS. 4-6 that have ITEV electrodes coupled directly to an expandable element. By separating the ITEV electrode(s) 156 from the expandable element 154, the system 150 of FIGS. 7A and 7B may simplify manufacturing and/or enhance expansion reliability.

As seen in FIG. 7A, the catheter 152 and the protective sheath 158 may be advanced into position within the patient's vasculature (e.g., within renal artery RA over guidewire G). Once in position, the sheath 158 may be retracted relative to the catheter 152 and/or the catheter 152 may be advanced relative to the sheath 158 such that the expandable element 154, the ITEV electrode(s) 156 and the return electrode 157 are positioned distally of the protective sheath 158. As seen in FIG. 7B, the expandable element 154 then may be expanded, such that the ITEV needle electrode(s) 156 puncture the vessel wall and are positioned extravascularly via an ITEV approach. Once the electrode(s) 156 are positioned extravascularly, PEF therapy may proceed between the ITEV electrode(s) 156 and the return electrode 157. The PEF therapy, for example, can modulate and/or denervate a neural fiber that contributes to renal function. Upon completion of the PEF therapy, the expandable element 154 may be collapsed, and the sheath 158 may be advanced relative to the catheter 152, such that the ITEV electrodes 156 are removed from the vessel wall. The system 150 then may be removed from the patient to complete the procedure.

Figure 8A:
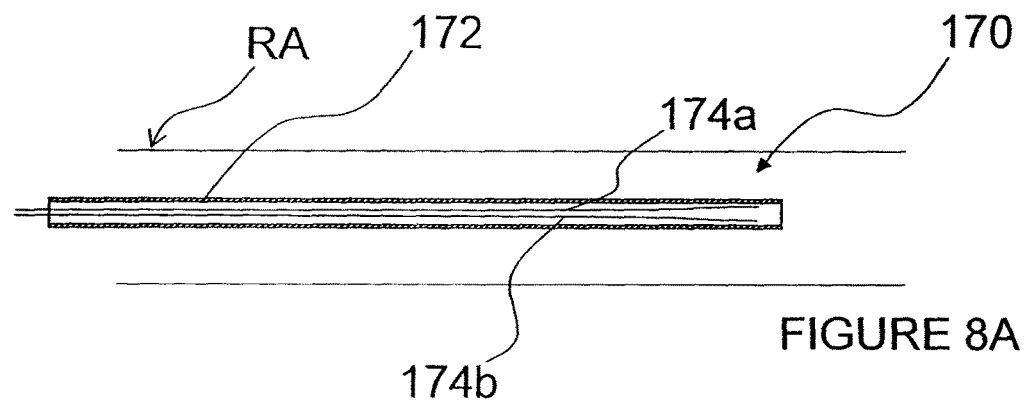
FIGS. 8A-8C are a schematic side-sectional view and schematic side-views, partially in section, illustrating methods and apparatus for pulsed electric field neuromodulation having at least one bipolar electrode pair with both electrodes of each electrode pair positioned extravascularly via an intra-to-extravascular approach.
Figure 8B:
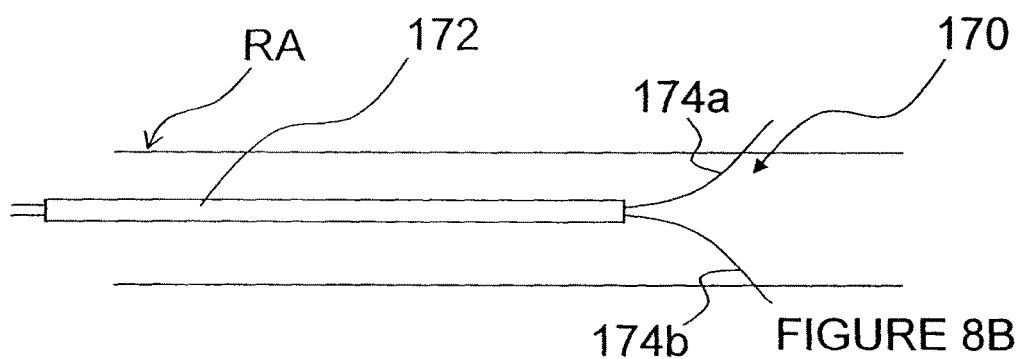
Figure 8C:
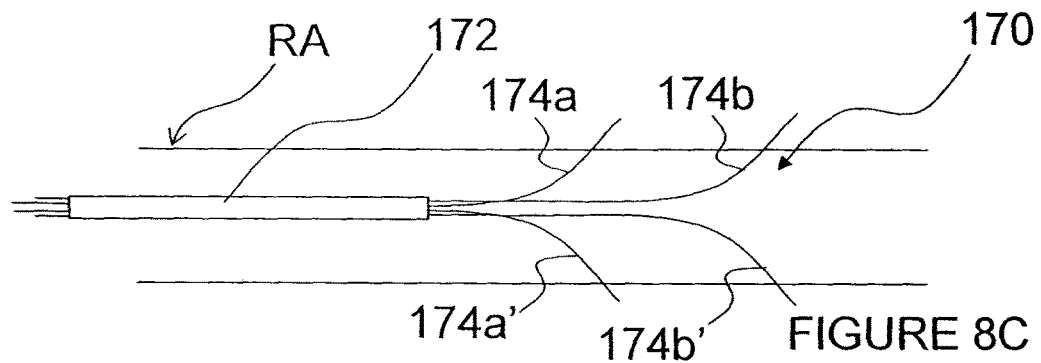

Referring now to FIGS. 8A-C, methods and apparatus for pulsed electric field neuromodulation are described utilizing one or more bipolar electrode pairs with both electrodes of each pair positioned extravascularly via an intra-to-extravascular approach. One example of such an ITEV PEF system 170 comprises a catheter or sheath 172 having shaped ITEV bipolar needle electrodes 174a and 174b that are configured for advancement to an intravascular location within the sheath. The electrodes 174a-b may have shape-memory properties (e.g., may be fabricated from a shape-memory alloy such as Nitinol) and may be insulated at locations other than their distal regions. As seen in FIG. 8B, upon advancement of the electrodes 174a-b to a position distal of the sheath 172 (e.g., via retraction of the sheath), the electrodes 174a-b assume their preformed shape and puncture the wall of the patient's vasculature, illustratively renal artery RA, such that the distal regions of the electrodes 174a-b are positioned extravascularly via an ITEV approach. As will be apparent, electrodes 174a and 174b may be longitudinally spaced relative to one another to better align the PEF therapy with a longitudinal dimension of the patient's vasculature. Furthermore, although the electrodes illustratively are spaced radially about 180° apart, it should be understood that the electrodes alternatively may be spaced with any desired radial separation (or lack thereof).

FIG. 8C illustrates another example of the ITEV PEF system 170 comprising multiple pairs of ITEV electrodes that are longitudinally spaced. The system 170, for example, can comprise a first bipolar electrode pair 174a and 174b, and a second bipolar electrode pair 174a' and 174b'. Additional pairs of bipolar electrodes at different circumferential positions or with different longitudinal spacing may be utilized as desired in other examples.

Once properly positioned, PEF therapy may be delivered across the electrodes 174 to achieve desired neuromodulation. Upon completion of the PEF therapy, the needle electrodes 174 may be retracted relative to the sheath 172, and/or the sheath 172 may be advanced relative to the electrodes 174, such that the electrodes are removed from the wall of the patient's vasculature and coaxed back into a constrained retrieval configuration within the sheath. The ITEV PEF system 170 then may be removed from the patient to complete the procedure.

Figure 9:
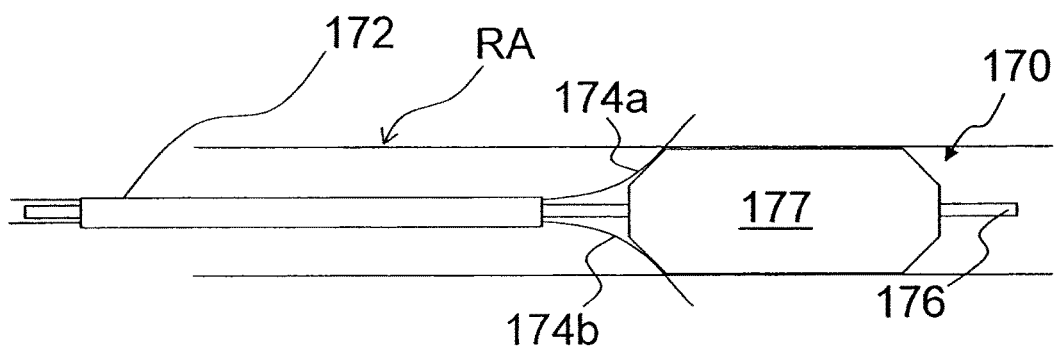
FIG. 9 is a schematic side-view, partially in section, of an alternative embodiment of the apparatus and methods of FIG. 8.

With reference to FIG. 9, an alternative embodiment of the ITEV PEF system 170 is described comprising a catheter 176 having an expandable element 177. The expandable element 177 acts as a guide that, when expanded, directs or forces the electrodes 174 across the vessel wall. More specifically, the expandable element 177 can direct the electrodes 174 through the vessel wall by advancing the electrodes 174 along the expandable element 177 after it has been expanded. Alternatively, the expandable element 177 can force the electrodes 174 across the vessel wall by advancing the electrodes 174 over the expandable element 177 while the expandable element 177 is in a reduced profile configuration and then expanding of the expandable element 177 to force the electrodes 174 across the wall of the vessel.

Figure 10A:
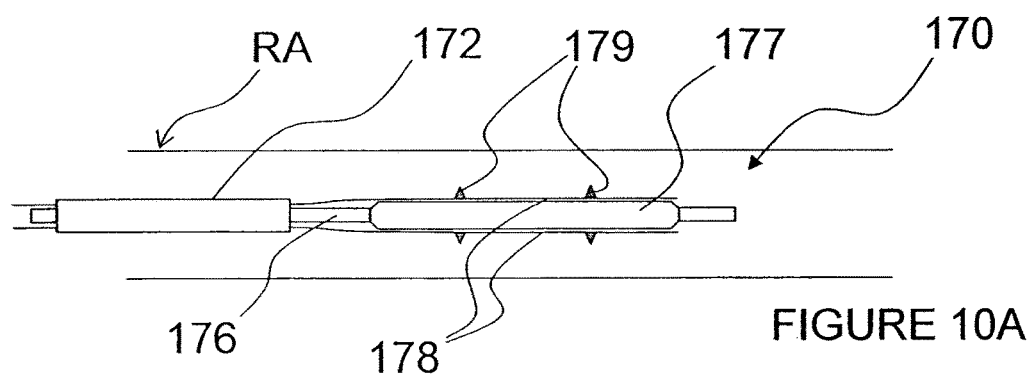
FIGS. 10A-10F are schematic side-views, partially in section, of alternative embodiments of the apparatus and methods of FIG. 9 comprising multiple pairs of bipolar electrodes.
Figure 10B:
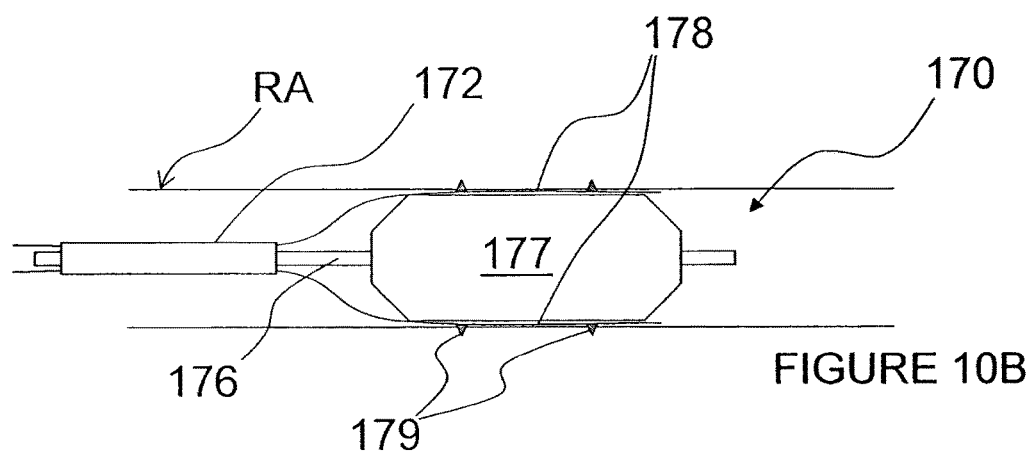

FIGS. 10A-F illustrate additional alternative embodiments of the ITEV PEF system 170 comprising multiple pairs of bipolar electrodes. In FIGS. 10A and 10B, the ITEV electrodes 174 have been replaced with ITEV electrode carriers 178. Each ITEV electrode carrier 178 comprises multiple electrodes 179. For example, each electrode carrier 178 may comprise a pair of electrically-isolated bipolar electrodes 179. Alternatively, each carrier 178 may comprise multiple electrodes 179 of a common polarity. The electrodes 179 comprise sharpened points, pins, or other raised features for penetrating the wall of the patient's vasculature. As seen in FIG. 10A, the electrodes 179 may be delivered to the stimulation site in a low profile configuration, e.g., through or within the sheath 172. The electrodes 179 then may be positioned extravascularly via an ITEV approach by expanding the expandable element 177, as in FIG. 10B.

Figure 10C:
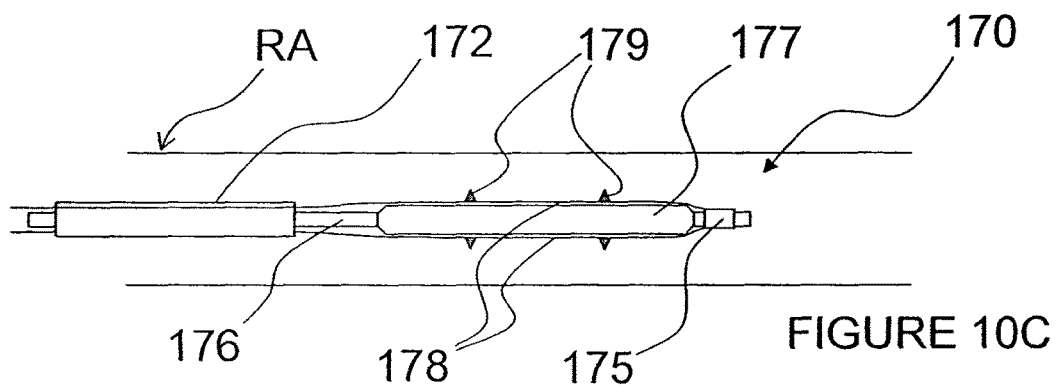
Figure 10D:
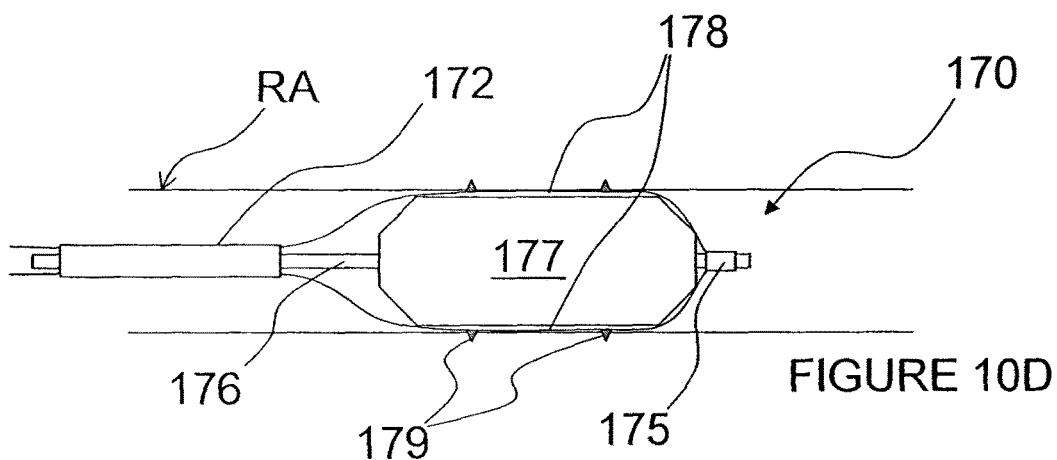

As seen in FIGS. 10C and 10D, the electrode carriers 178 optionally may be coupled to a catheter 176 distal of the expandable element 177 at a collar 175. The collar 175 may be slidingly attached to the catheter 176 and/or may be longitudinally constrained. An expected benefit of attaching the carriers to the catheter is good control of the extravascular positioning of electrodes 179 via an ITEV approach.

Figure 10E:
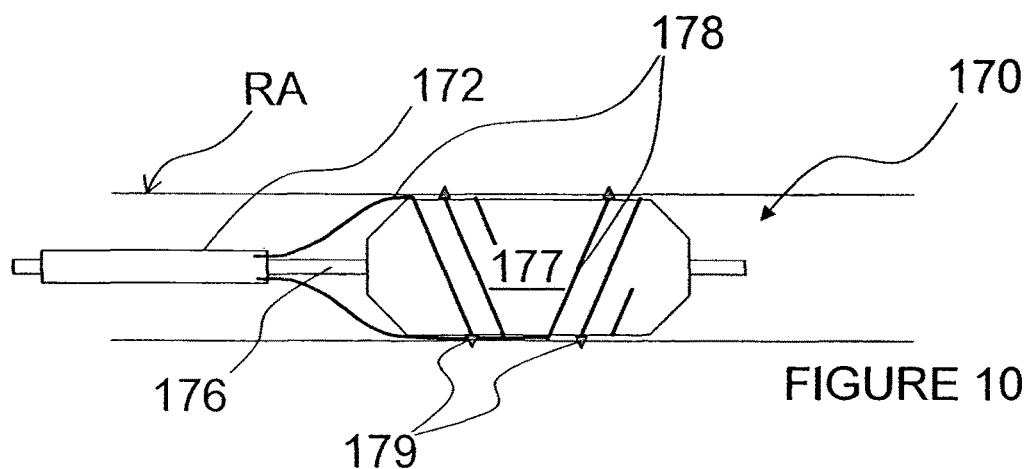

As seen in FIG. 10E, the electrode carriers 178 optionally may spiral around the expandable element 177. The carriers 178 optionally may comprise several electrodes 179 positioned at multiple circumferential positions to facilitate more circumferential PEF therapy. The electrode carriers 178 preferably are electrically isolated from one another. For example, the carriers 178 may be insulated at all regions except for at the electrodes 179.

Figure 10F:
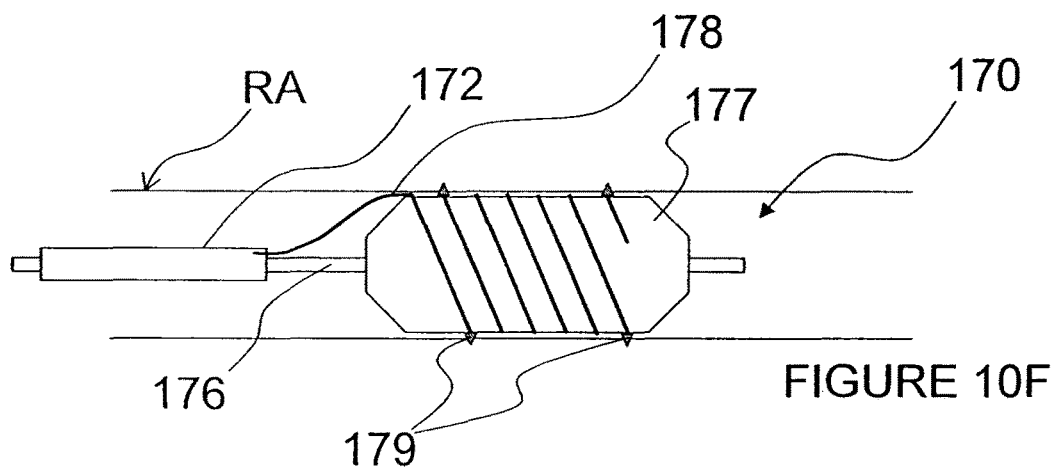

As seen in FIG. 10F, the system 170 optionally may comprise a single electrode carrier 178 that spirals around the expandable element 177. A plurality of the electrodes along the unitary carrier may be of a common polarity and/or may be electrically isolated from one another and of varying polarity to form bipolar electrode pair(s). The electrodes 179 may be positioned a multiple circumferential positions, as desired.

Figure 11A:
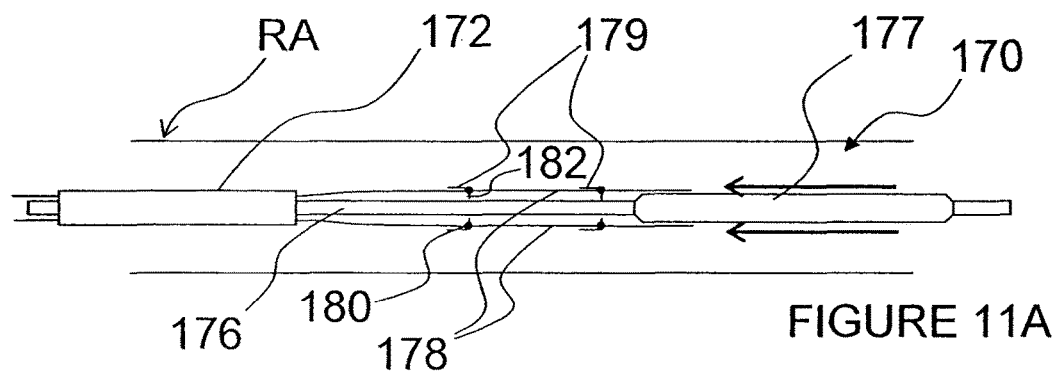
FIGS. 11A-11C are schematic side-views, partially in section, of an alternative embodiment of the apparatus and methods of FIG. 10 comprising a safety feature for intravascular delivery of the electrodes prior to extravascular placement.
Figure 11B:
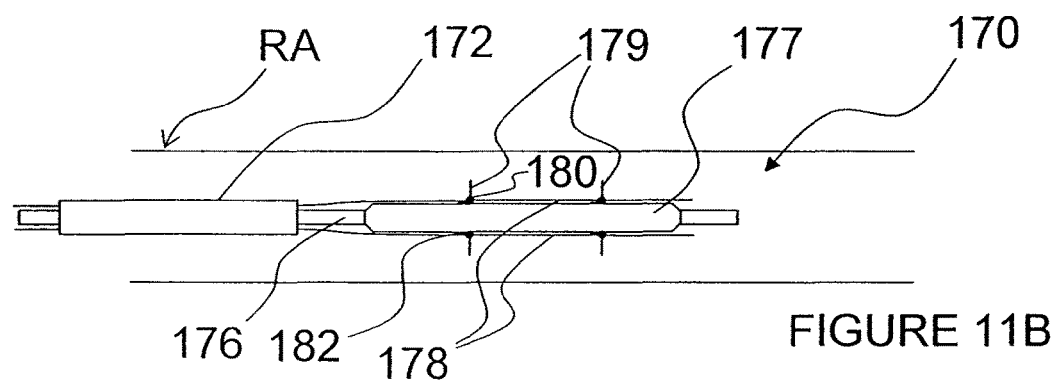
Figure 11C:
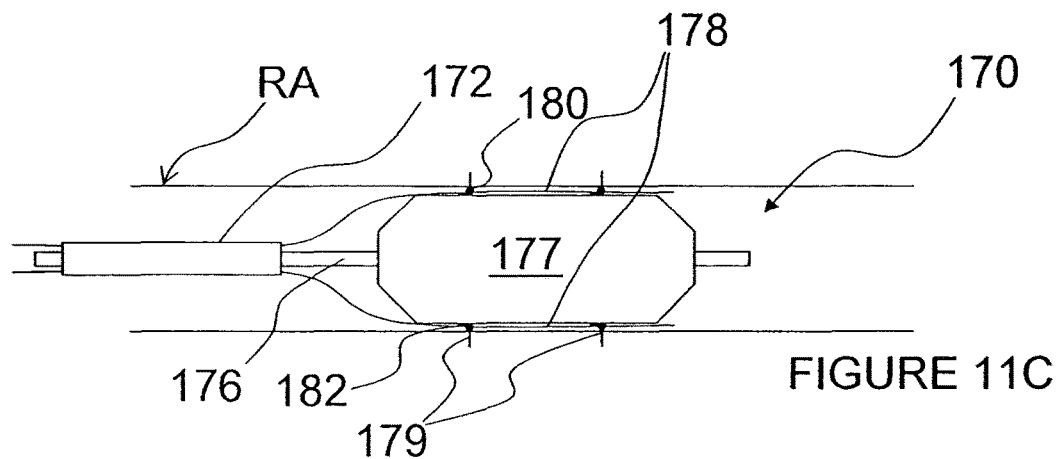

FIGS. 11A-C show additional examples of the ITEV PEF system 170 comprising a safety feature that facilitates intravascular delivery of the electrodes 179 prior to extravascular placement of the electrodes. In the embodiment of FIGS. 11A-C, the electrodes 179 are coupled to electrode carriers 178 in a manner that facilitates rotation of the electrodes 179 relative to the respective carriers 178. For example, the electrodes 179 may be coupled to the carriers 178 at pivots 180, which may comprise rotational bearing surfaces. Furthermore, the electrodes 179 comprise extensions 182 that co-act with the expandable element 177 to selectively rotate the electrodes 179 between a reduced delivery and retrieval profile and an expanded profile suitable for ITEV delivery of the electrodes. The electrodes 179 optionally may be biased towards the reduced profile, e.g., via a spring mechanism. The reduced profile serves as a safety feature that reduces a risk of inadvertent perforation of vascular tissue prior to ITEV placement of the electrodes at a treatment site.

As seen in FIG. 11A, the electrodes 179 lie flat near or against the electrode carrier 178 during delivery to an intravascular treatment site (e.g., through or within the sheath 172). The electrodes 179 are positioned proximal of the expandable element 177 during delivery. Once positioned within the vessel, the electrodes 179 are expanded such that their tips point radially outward by retracting the expandable element 177 relative to the electrode carriers 178. As seen in FIG. 11B, retraction of the expandable element 177 causes it to engage the extensions 182 of the electrodes 179 such that the electrodes 179 rotate about the pivots 180 to the expanded configuration suitable for ITEV delivery of the electrodes 179. The expandable element 177 then is expanded, such that the electrodes 179 are forced through the vessel wall via an ITEV approach, as in FIG. 11C. ITEV PEF therapy then may proceed, as desired. Upon completion of the therapy, the expandable element 177 and the electrodes 179 are returned to the reduced profile configuration for retrieval from the patient.

Figure 12:
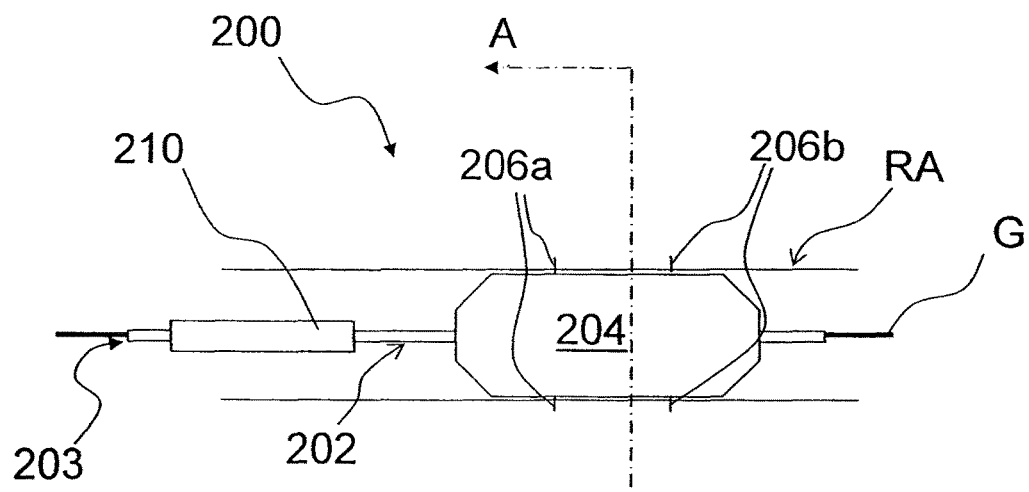
FIG. 12 is a schematic side-view, partially in section, of methods and apparatus for pulsed electric field neuromodulation via at least one angularly-aligned, longitudinally-spaced bipolar electrode pair positioned extravascularly via an intra-to-extravascular approach.

With reference now to FIG. 12, methods and apparatus for pulsed electric field neuromodulation via at least one angularly-aligned, longitudinally-spaced bipolar electrode pair positioned extravascularly via an intra-to-extravascular approach are described. FIG. 12, more specifically, shows an example of an ITEV PEF system 200 that comprises a catheter 202 having an expandable element 204 with at least one pair of longitudinally-spaced bipolar needle electrodes 206*a* and 206*b*. The needle electrodes 206*a-b* are positioned at substantially the same angular position along the expandable element (in FIG. 12, the system illustratively comprises two pairs of longitudinally-spaced, angularly-aligned bipolar electrodes 206*a-b* positioned at distinct circumferential positions). Angular alignment of the longitudinally-spaced bipolar electrodes 206*a-b* may align the PEF therapy with a longitudinal axis of target neural fibers, as described previously. The bipolar pairs of needle electrode 206 may comprise any desired longitudinal spacing; for example, the electrodes may comprise spacing in the range of about 0.5-10 mm.

The ITEV PEF system 200 may be delivered to an intravascular treatment site, such as a site within renal artery RA, using well-known percutaneous techniques. For example, the system 200 may be advanced over a guidewire G positioned with a lumen 203 of a catheter 202, which may be advanced through/within a guide catheter or a sheath 210. Once positioned at the treatment site, an expansion element 204 is expanded to force the bipolar needle electrodes 206 across the wall of the vessel such that the ends of the electrodes 206 are positioned extravascularly via an ITEV approach. The expansion element 204 may, for example, be expanded by (a) inflating a balloon, (b) self-expanding a basket or cage after positioning the element 204 distal of sheath 210, and/or (c) mechanical expanding a basket or cage via various push/pull and/or tension/compression techniques.

Positioning the electrodes 206 using an ITEV technique places the electrodes in closer proximity to target neural fibers that contribute to renal function. As discussed previously, renal nerves may be located in the adventitia of the renal arteries and/or in tissue immediately surrounding the renal arteries. Such ITEV positioning of the electrodes, as well as selected angular alignment of the bipolar electrode pair(s), may reduce energy requirements necessary to achieve desired neuromodulation, as compared to a PEF system comprising intravascularly-positioned electrodes.

The electrodes 206 preferably are of small enough caliber to safely cross the wall of renal artery RA without significant risk of bleeding, vessel wall injury, etc. For example, the electrodes may be of a caliber less than about 23 Gauge. Furthermore, the electrodes may be solid or may comprise one or more lumens. When with lumen(s), the needle electrodes may be configured for infusion of agents that either enhance the desired neuromodulatory effect (e.g., saline injection may be used to locally enhance conductivity during PEF therapy) or provide protective effects (e.g., cooling agents may be injected to protect non-target tissues).

The needle electrodes 206 also may be conductive along their entire lengths or may be insulated along at least part of their lengths. For example, the needle electrodes 206 can be insulated at locations other than their distal ends. Insulation along part of the lengths of electrodes 206 may reduce undesirable delivery of pulsed electric field therapy to non-target tissues, e.g., the intima or to the media of the patient's vessel. Such insulated electrodes preferably comprise lengths sufficient to place the non-insulated portions of the electrodes extravascularly at positions at least within the vasculature adventitia during ITEV positioning of the electrodes.

Figure 13A:
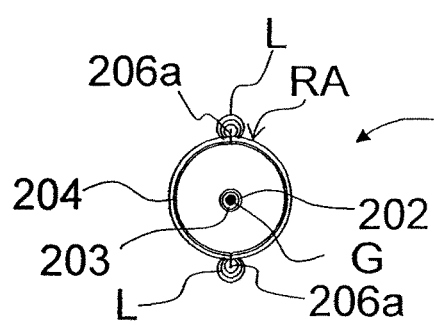
FIGS. 13A-13D are schematic cross-sectional views along section line A-A of FIG. 12, illustrating methods and apparatus for circumferential pulsed electric field modulation of target neural fibers via multiple pairs of angularly-aligned, longitudinally-spaced ITEV bipolar electrode pairs, each pair positioned at a different circumferential position.
Figure 13B:
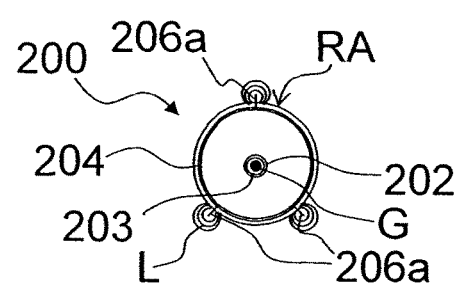
Figure 13C:
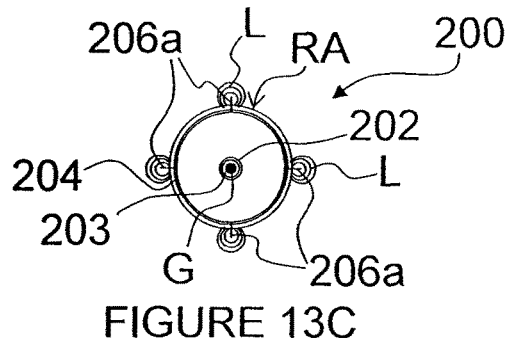

Referring now to FIGS. 13A-D, methods and apparatus for circumferential pulsed electric field modulation of target neural fibers via multiple pairs of angularly-aligned, longitudinally-spaced ITEV bipolar electrode pairs in which each electrode pair is positioned at a different circumferential position. FIGS. 13A-D illustrate several examples of the ITEV PEF system 200 along section line A-A of FIG. 12. In FIG. 13A, the ITEV PEF system 200 comprises two pairs of angularly-aligned, longitudinally-spaced bipolar electrodes 206 circumferentially positioned approximately 180° apart, as in FIG. 12. In FIG. 13B, the system 200 comprises three pairs of such bipolar electrodes spaced approximately 120° apart. In FIG. 13C, the system 200 comprises four pairs spaced roughly 90° apart, and in FIG. 13D, the system 200 comprises eight pairs spaced about 45° apart. As will be apparent, any desired number of electrode pairs may be provided. Furthermore, although the electrode pairs shown in FIGS. 13A-D have been equally circumferentially spaced, they alternatively may be circumferentially spaced at any other desired spacing, including any other desired unequal circumferential spacing.

Figure 13D:
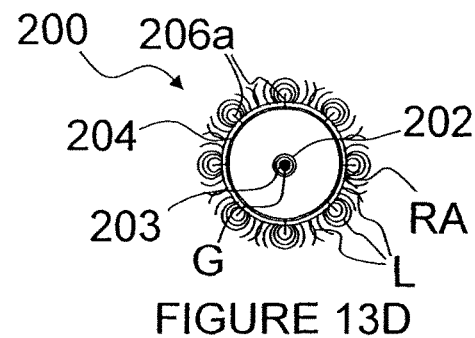

As illustrated by field lines L in FIGS. 13A-D, the tissue region affected by PEF therapy delivery across each bipolar electrode pair, e.g., the tissue region experiencing desired neuromodulation, is confined to a narrow circumferential segment of the treatment site. Providing multiple pairs of bipolar ITEV electrode pairs 206 may provide a more circumferential treatment. As seen in FIG. 13D, adding additional pairs of ITEV bipolar electrodes 206 eventually causes the circumferentially-affected segments to overlap, thereby providing full circumferential treatment. In some cases, it may be desirable to provide full circumferential treatment, while in other cases it may be desirable to provide less than complete circumferential treatment. The medical practitioner may provide any desired level of circumferential treatment and/or may utilize any desired number of circumferentially-spaced bipolar electrode pairs. Circumferential PEF therapy along a longitudinal segment of the patient's vessel may be achieved by collapsing the expansion element 204, rotating the catheter 202 a desired amount about its longitudinal axis, and then re-expanding the expansion element 204 to re-position electrode pairs 206 extravascularly for treatment of another circumferential longitudinal segment of the patient's vessel. This process can be repeated at a single longitudinal location as desired.

FIGS. 14A and 14B show additional ITEV PEF systems 300 that comprise a catheter 302 having an outer sheath 304, a guidewire tube 306, and an atraumatic nosecone 308. The guidewire tube 302 is coupled to and extends through or communicates with a lumen 309 of the atraumatic nosecone 308. The system 300 also includes a number of proximally-oriented ITEV needle electrodes 310 coupled to the nosecone 308 at their distal regions, and a pusher tube 312 coaxially positioned about the guidewire tube 306. The pusher tube 312 optionally has a flared tip 314, which may be relatively stiff and/or radiopaque. The electrodes 310 may be coupled to the PEF generator 50 via electrical contacts formed with or within the guidewire tube 306 (e.g., via a metallic braid, coil or wire on or near an outer diameter of the guidewire tube). The electrodes 310 may physically contact these electrical contacts to facilitate delivery of PEF therapy. In some embodiments, the flared tip 314 completes the circuit upon contacting the electrodes, as in FIG. 14B.

FIG. 14A shows the system 300 in the reduced delivery and retrieval configuration with the electrodes 310 positioned within the sheath 304. Upon intravascular placement at a treatment site, the sheath 304 is retracted and/or the guidewire tube 306 is advanced, such that the electrodes 310 are removed from the sheath 304. The electrodes 310 preferably are fabricated from an elastic material that resists deformation and applies a restoring force upon deformation. Furthermore, the electrodes 310 preferably are coupled to the nosecone 308 in a manner that biases the electrodes 310 to the reduced profile shown in FIG. 14A.

As seen in FIG. 14B, when the catheter 302 is positioned at a treatment site (e.g., within the renal artery RA), the pusher tube 312 is advanced relative to the guidewire tube 306 such that the flared tip 314 engages and elastically deforms the electrodes 310 radially outward. The electrodes 310 pierce the vessel to position the tips of the electrodes extravascularly via an ITEV approach. The catheter 302 optionally may be retracted after deformation of the electrodes 310 to engage the electrodes with the patient's vessel and place the electrodes extravascularly. PEF therapy then may proceed to achieve desired neuromodulation. Upon completion of the treatment, the pusher tube 312 is retracted relative to the guidewire tube 306 and the electrodes 310. The guidewire tube 306 is advanced slightly to release the electrodes 310 from the vessel wall. The restoring force provided by the electrodes 310 returns the electrodes 310 to the reduced at-rest profile. The sheath 304 then may be advanced relative to the guidewire tube 306, such that the needle electrodes 310 are once again positioned within the sheath 304 as in FIG. 16A for retrieval and removal from the patient.

In an additional or alternative embodiment of the apparatus of FIGS. 14A and 14B, the needle electrodes 310 may be replaced with needle housings through which the needle electrodes may be advanced. The needle housings are expanded into contact with a vessel wall, and the needle electrodes then are advanced across the vessel wall. Such advancement may be accomplished via a variety of mechanical means. For example, advancement of the pusher tube past a specified position relative to the guidewire tube, the nosecone and/or the needle housings may release a spring-loaded member that advances the needles.

Figure 14C:
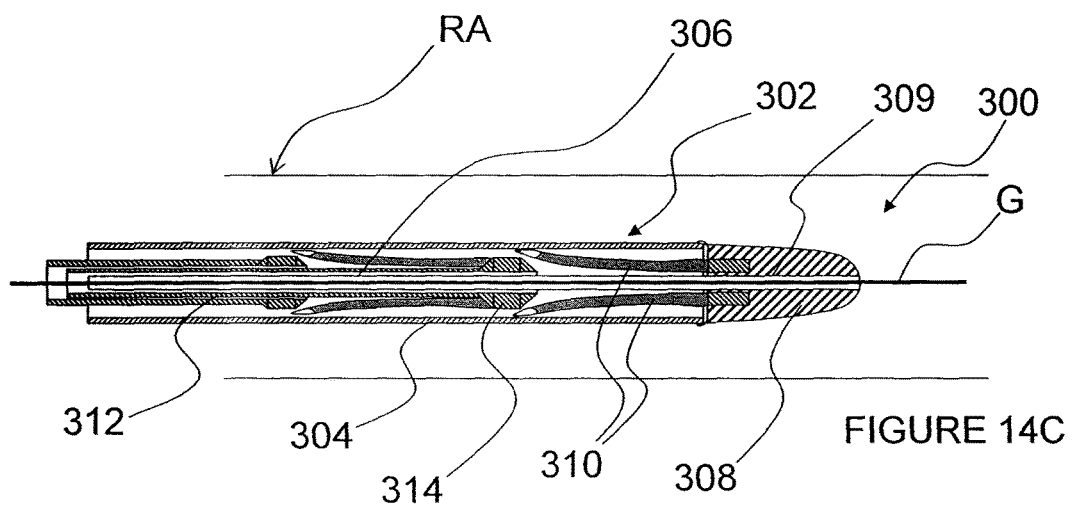
Figure 14D:
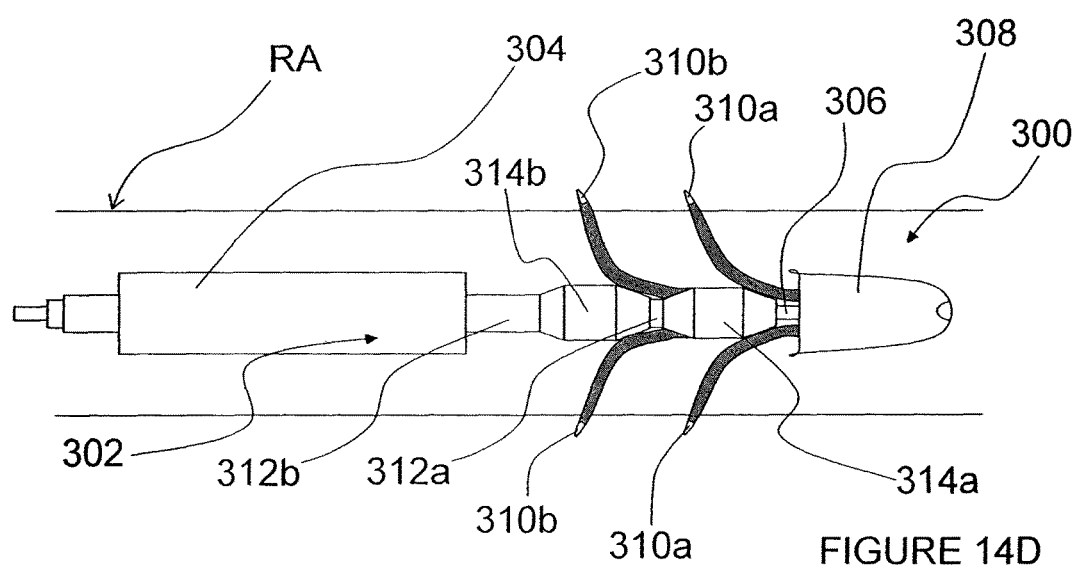

FIGS. 14C and 14D illustrate an alternative embodiment of the ITEV PEF system 300 comprising one or more longitudinally spaced pairs of bipolar electrodes. In FIGS. 14C and 14D, needle electrodes 310a are coupled to the nosecone 308, and needle electrodes 310b are coupled to a proximal region of a first flared tip 314a of a first pusher tube 312a. The system 300 further comprises a second pusher tube 312b having a second flared tip 314b. The second pusher tube 312b is coaxially disposed about the first pusher tube 312a.

Electrodes 310a and 310b form one or more longitudinally spaced pairs of bipolar electrodes. For example, electrodes 310a may comprise active electrodes and electrodes 310b comprise return electrodes, or vice versa. As seen in FIG. 14C, the electrodes may be delivered within the sheath 304. Once positioned at a treatment site, the sheath 304 may be withdrawn, and the electrodes 310 may be positioned extravascularly via an ITEV approach, as in FIG. 14D. Specifically, the first pusher tube 312a may be advanced relative to the guidewire tube 306, such that first flared tip 314a impinges upon and deforms the needle electrodes 310a. This urges the electrodes 310a across the vessel wall. Likewise, the second pusher tube 312b may be advanced relative to the first pusher tube 312a such that the second flared tip 314b impinges upon and deforms the needle electrodes 310b. This mechanism urges the electrodes 310b across the vessel wall. In the embodiment of FIGS. 14C and 14D, the flared tips 314 comprise distal profiles that provide gradual transitions for deforming the electrodes 310.

FIGS. 15A-C show examples of another ITEV PEF system 320 that comprises a catheter 322 having (a) a plurality of proximal electrode lumens 324 terminating at proximal side ports 325, (b) a plurality of distal electrode lumens 326 terminating at distal side ports 327, and (c) a guidewire lumen 323. The catheter 322 preferably comprises an equal number of proximal and distal electrode lumens. The system 320 also includes proximal needle electrodes 328 that may be advanced through the proximal electrode lumens 324 and needle electrodes 329 that may be advanced through the distal electrode lumens 326.

As illustrated in FIG. 15A, the catheter 322 may be advanced over the guidewire 321 via the lumen 323 to a treatment site within the patient's vasculature (e.g., to a treatment site within the patient's renal artery RA). During intravascular delivery, the electrodes 328 and 329 are positioned such that their non-insulated and sharpened distal regions are positioned within the lumens 324 and 326, respectively. Once positioned at a treatment site, a medical practitioner may advance the electrodes via their proximal regions that are located external to the patient. As seen in FIG. 15B, such advancement causes the distal regions of the electrodes 326 and 329 to exit side ports 325 and 327, respectively, and pierce the wall of the patient's vasculature such that the electrodes are positioned extravascularly via an ITEV approach.

The proximal electrodes 328 can be connected to PEF generator 50 as active electrodes and the distal electrodes 329 can serve as return electrodes. In this manner, the proximal and distal electrodes form bipolar electrode pairs that align PEF therapy with a longitudinal axis or direction of the patient's vasculature. As will be apparent, the distal electrodes 329 alternatively may comprise the active electrodes and the proximal electrodes 328 may comprise the return electrodes. Furthermore, the proximal and/or the distal electrodes may comprise both active and return electrodes. Any combination of active and distal electrodes may be utilized, as desired.

When the electrodes 328 and 329 are positioned extravascularly, PEF therapy may proceed to achieve desired neuromodulation. After completion of the PEF therapy, the electrodes may be retracted within lumens 324 and 326. The catheter 322, as well as the guidewire 321 then may be removed from the patient to complete the procedure. Additionally or alternatively, the catheter may be repositioned to provide PEF therapy at another treatment site.

Figure 16A:
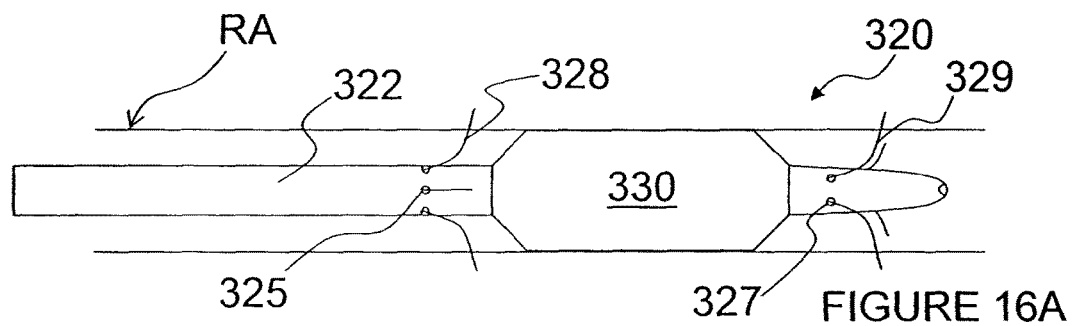
FIGS. 16A and 16B are schematic side-views of alternative embodiments of the methods and apparatus of FIG. 15.
Figure 16B:
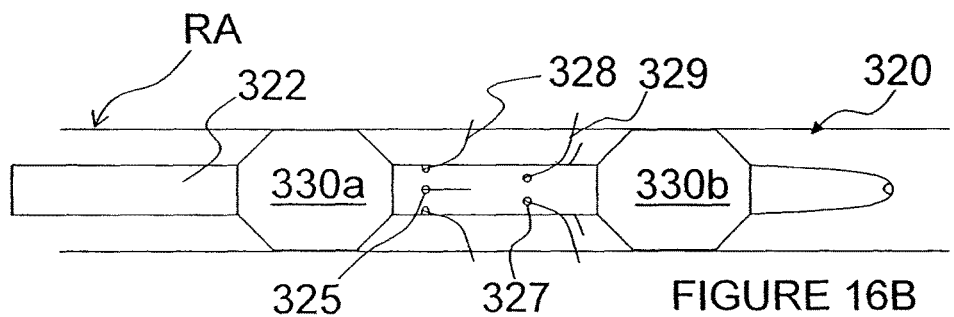

FIGS. 16A and 16B show alternative embodiments of the ITEV PEF system 320. In FIG. 16A, the catheter 322 of the system 320 further comprises an expandable centering element 330, which may comprise an inflatable balloon or an expandable basket or cage. In use, a centering element 330 may be expanded prior to deployment of the needle electrodes 328 and 329 to center the catheter 322 within the patient's vessel (e.g., within renal artery RA). Centering the catheter 322 is expected to facilitate delivery of all needle electrodes to desired depths within/external to the patient's vessel (e.g., to deliver all of the needle electrodes to the same depth).

In FIG. 16A, the illustrated centering element 330 is positioned between the proximal side ports 325 and the distal side ports 327, i.e., between the delivery positions of the proximal and distal electrodes. However, it should be understood that centering element 330 additionally or alternatively may be positioned at a different location or at multiple locations along the length of catheter 322 (e.g., at a location proximal of side ports 325 and/or at a location distal of side ports 327). In FIG. 16B, the system 320 illustratively comprises a first centering element 330a positioned proximal of the proximal side ports 325 and a second centering element 330b positioned distal of the distal side ports 327.

Figure 17A:
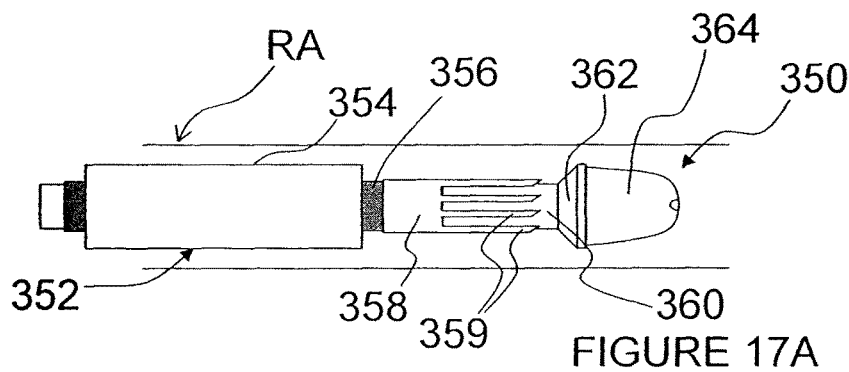
FIGS. 17A-17E are schematic side-views, partially in section, of still further methods and apparatus for pulsed electric field neuromodulation via electrodes positioned extravascularly via an intra-to-extravascular approach.
Figure 17B:
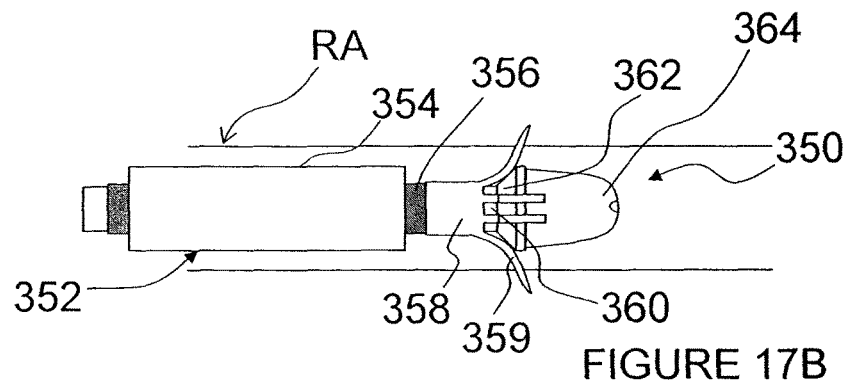

Referring now to FIGS. 17A-E, ITEV PEF systems 350 utilizing one or more hypotubes are described. In the embodiment of FIGS. 17A and 17B, the ITEV PEF system 350 comprises a catheter 352 having an outer sheath 354, an outer shaft 356, a hypotube 358 with multiple distal extensions 359, and an inner shaft 360 with a guide block 362. The inner shaft 360 terminates at an atraumatic tip 364, and a guidewire lumen preferably extends through the inner shaft and the atraumatic tip. The hypotube 358 is connected proximally to the outer shaft 356, and the outer shaft 356 is coaxially positioned over the inner shaft 360.

The hypotube 358 can have extensions 359 that may be fabricated by cutting away portions of the hypotube. The hypotube 358 may be fabricated from a conductive material, such as a metal alloy or platinum, or the hypotube may comprise a relative non-conductive material. The extensions 359 may be selectively insulated and/or non-insulated, and they may be electrically coupled to the PEF generator 50 to provide one or more extension electrodes. The extension electrodes may, for example, be etched onto the hypotube and its extensions, e.g., via a metal deposition process. Electrical contacts for energy delivery may be exposed at the tips of insulated extensions 359; alternatively, the non-insulated contacts may extend across all or part of the lengths of the extensions. Furthermore, the entire hypotube 358 may comprise an electrode when the hypotube is fabricated from a conductive material.

The extension electrode(s) 359 may be of a common polarity or may be of different polarities. When of different polarities, PEF therapy may be delivered across the electrodes in a bipolar fashion. When of common polarity, the electrodes may be utilized in a monopolar fashion, e.g., with an external ground pad. Alternatively, the catheter 352 optionally may comprise one or more additional electrodes of opposite polarity along its length that may be utilized in a bipolar fashion with the extension electrode(s) 359 of the hypotube 358. In one embodiment, the outer shaft 356 comprises at least a second hypotube along its length having extension electrode(s) that serve as the additional electrode(s) of opposite polarity and may be utilized to form spaced bipolar electrode pair(s) for delivery of the PEF therapy.

As seen in FIG. 17A, the catheter 352 may be advanced to a treatment site within a patient's vasculature, such as a treatment site within renal artery RA, using well-known percutaneous techniques (e.g., through a guide catheter). Once properly positioned, the outer sheath 354 may be retracted to expose the hypotube 358, and then the outer shaft 356 may be advanced relative to inner shaft 360 to drive the extensions 359 against the guide block 362. As seen in FIG. 17B, the guide block 362 provides a tapered transition that progressively deforms extensions 359 in an elastic or plastic manner as the outer shaft 354 is advanced relative to the inner shaft 360. This deformation directs the extensions 359 radially outward to detone the extension electrodes. Continued advancement of the outer shaft causes the extension electrodes to penetrate the vessel wall and to be positioned extravascularly via an ITEV approach. With the extension electrodes 359 positioned extravascularly, PEF therapy may proceed.

Upon completion of the PEF therapy, the extensions 359 once again may be collapsed against the outer shaft 356 for retrieval of the system 350 from the patient. If the deformation of the extensions 359 comprises elastic deformation, the outer shaft 356 may be retracted relative to the wall of renal artery RA to remove the extensions from the wall. The extensions 359 then will return to their at-rest configuration of FIG. 17A. If the deformation is plastic, then the extensions 359 may, for example, be collapsed by advancing the outer sheath 354 or a guide catheter over the outer shaft 356 such that the sheath 354 abuts the bases of the extensions 359. The outer shaft 356 then may be retracted while the sheath 354 is held stationary or advanced relative to the outer shaft to collapse the extensions 359 within the sheath 354 for retrieval of the system 350 from the patient.

Figure 17C:
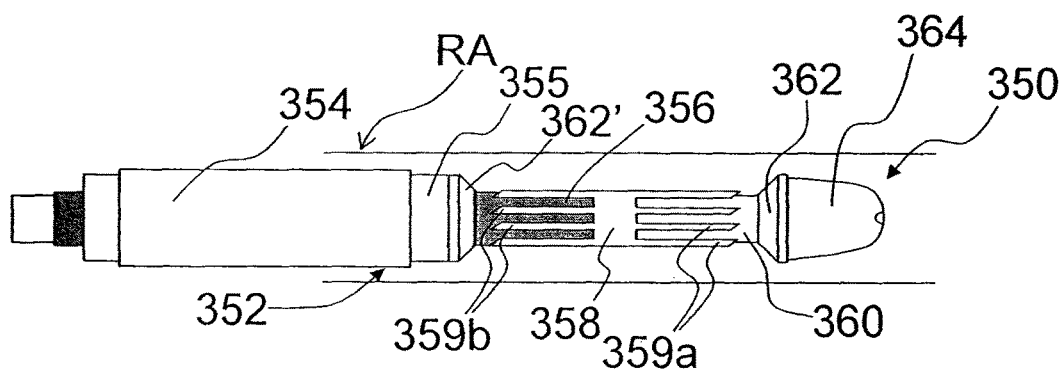
Figure 17D:
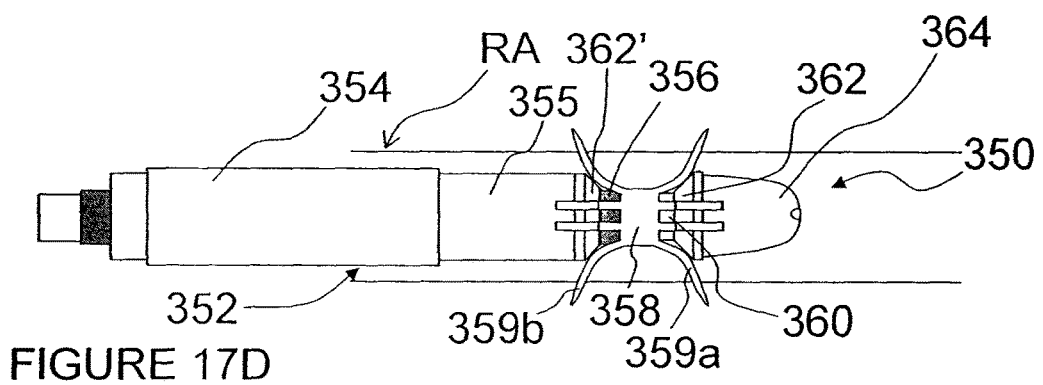

As seen in FIGS. 17C and 17D, the ITEV PEF system 350 optionally may comprise one or more longitudinally spaced pairs of ITEV electrodes. In FIGS. 17C and 17D, the hypotube 358 comprises distal extensions 359a and proximal extensions 359b. The distal extensions 359a may be deployed extravascularly in the manner described previously. For ITEV deployment of the proximal extensions 359a, the system 350 further comprises a proximal pusher tube 355 having a distally-oriented guide block 362' for deforming the proximal extensions 359b. The pusher tube 355 is coaxially disposed over the outer shaft 356, but within the outer sheath 354. As seen in FIG. 17D, the pusher tube 355 may be advanced relative to the outer shaft 356 in order to deform the proximal extensions 359b and position the extension electrodes extravascularly via an ITEV approach. The proximal and distal extension electrodes of the hypotube 358 form one or more longitudinally spaced bipolar electrode pairs.

Figure 17E:
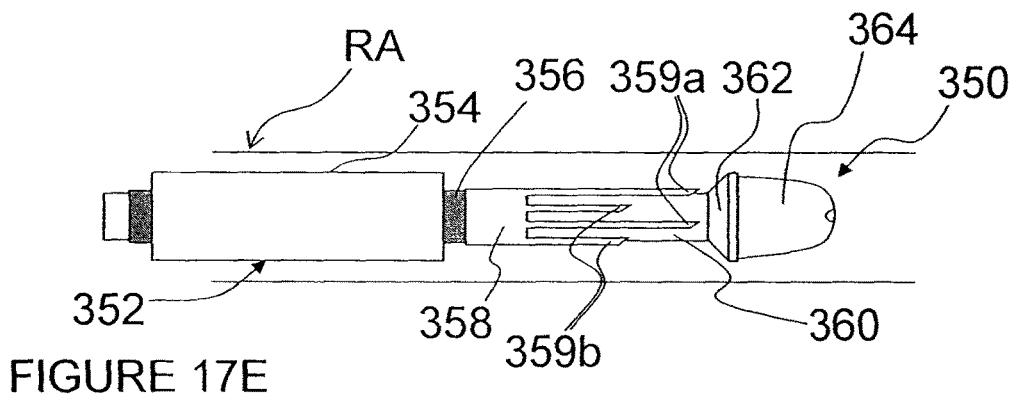

In FIG. 17E, ITEV PEF system 350 again comprises the distal extensions 359a and the proximal extensions 359b. However, in the embodiment of FIG. 17E, the proximal and distal extensions are all distally-oriented, with the distal extensions 359a being of a greater length than the proximal extensions 359b. During extravascular placement of the extensions, the additional length of the distal extensions 359a causes the distal extensions to pierce the wall of the patient's vessel more distally than do the proximal extensions 359b. In this manner, the proximal and distal extensions 359a-b are longitudinally spaced apart from one another when deployed extravascularly. After completion of extravascular PEF therapy, the distal orientation of the proximal and distal extensions 359a-b facilitates collapse and retrieval of the extensions. The outer shaft 356 may be retracted while the sheath 354 is held stationary or advanced relative to the outer shaft to collapse the extensions 359a-b within the sheath 354 for retrieval of the system 350 from the patient.

Although several examples of the ITEV systems 350 shown in FIGS. 17A-E illustrate deployment of the ITEV extension electrodes 359 via guide block(s) 362, it should be understood that the electrodes may be deployed via a variety of alternative techniques. For example, a push/pull mechanism, such as pull wire, may be utilized to deform the hypotube extensions. Alternatively, a pressure or vacuum channel may be used. An array of hypotubes and/or hypotube extension electrodes optionally may be deployed via a single deployment mechanism.

With reference to FIGS. 18A-D, alternative embodiments of the ITEV PEF system 350 are described. In FIGS. 18A-D, the guide block(s) 362 have been replaced with alternative deployment mechanisms comprising at least one expandable member, such as an inflatable balloon 366. Furthermore, the hypotube 358 has been replaced with a stent-like element 370 having the extensions 359. As will be apparent, the balloon(s) 366 alternatively may be used in combination with the hypotube 358, and/or the stent-like element 370 alternatively may be used in combination with the guide block(s) 362.

As with the hypotube 358, the stent-like element 370 may be completely conductive and may serve as a unitary electrode. Alternatively, the stent-like element 370 may be fabricated from a relatively insulating material with electrode contacts that are etched or deposited onto the element and/or its extensions. A variety of electrode configurations may be provided. Furthermore, the multiple elements 370 (or a combination of hypotubes 358 and elements 370) may be provided. In addition or as an alternative to the deployment mechanisms illustrated in FIG. 18, the extensions 359 may be deployed via other deployment mechanisms, such as push/pull mechanisms (e.g., a pull wire) or a pressure/vacuum channel.

Figure 18A:
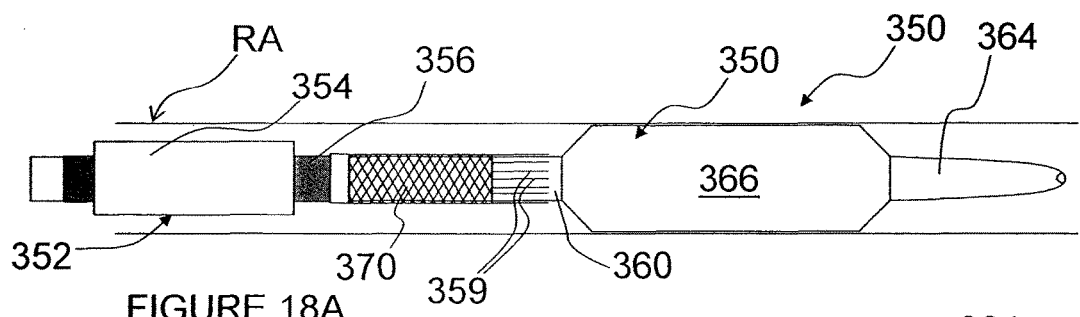
FIGS. 18A-18D are schematic side-views, partially in section, of alternative embodiments of the methods and apparatus of FIG. 17.
Figure 18B:
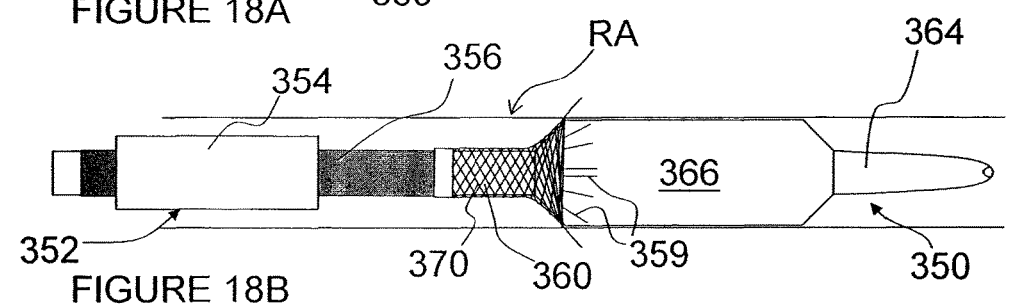

As seen in the embodiment of FIGS. 18A and 18B, the system 350 may be positioned at a treatment site, and the balloon 366 coupled to the inner shaft 360 may be inflated into contact with the vessel wall. As seen in FIG. 18A, the inflated balloon 366 centers the system 350 within the vessel and provides a tapered guide path that provides a smooth transition for deformation of the extensions 359 of the stent-like element 370 during ITEV placement of the extension electrodes. As seen in FIG. 18B, the outer shaft 356 may be advanced relative to the inner shaft 360 such that the extensions 359 begin to deform about the balloon and are directed radially outward. This deformation optionally may be assisted via additional deployment mechanisms, such as pull-wires, to begin deformation of the extensions 359. Continued advancement of the outer shaft 356 relative to the inner shaft causes the extensions 359 to pierce the vessel wall so that the ends of the extension electrodes 359 are positioned extravascularly via an ITEV approach.

Figure 18C:
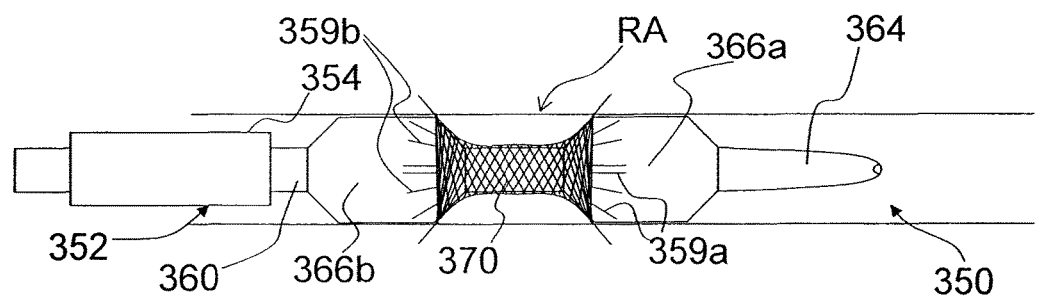

As seen in FIG. 18C, the stent-like element 370 may comprise longitudinally spaced extensions 359a and 359b to provide longitudinally spaced bipolar electrode pairs. In FIG. 18C, the inner shaft 360 comprises distal and proximal expandable elements, illustratively a distal balloon 366a and a proximal balloon 366b. The stent-like element 370 is positioned between the proximal and distal balloon, with the extensions 359a and 359b overlapping the distal and proximal balloons 366a-b, respectively. This overlap obviates a need for the outer shaft 356 shown in FIGS. 18A and 18B. ITEV placement of the extension electrodes 359a-b is achieved by inflating balloons 366.

Figure 18D:
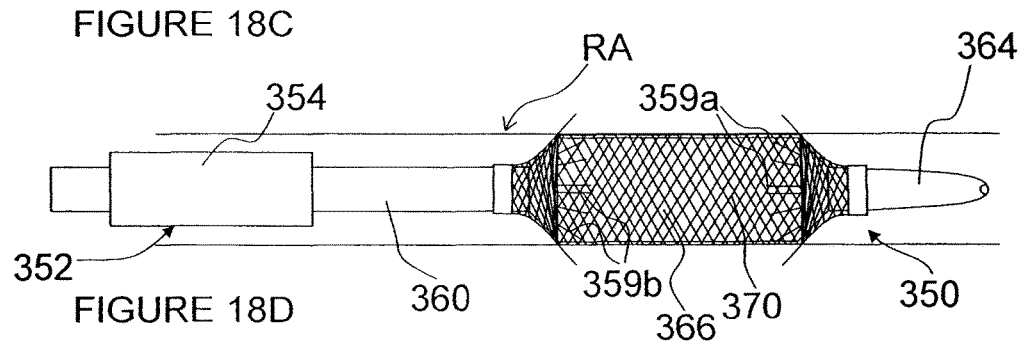

As seen in FIG. 18D, the stent-like element 370 with proximal and/or distal extensions 359 may be positioned over an expandable element, such as inflatable balloon 366. The expandable element 370 may be coupled to the shaft 360 proximally and/or distally (e.g., at a distal collar 368a and at a proximal collar 368b). At least one of the collars 368a or 368b is slidingly coupled to the shaft 360 to facilitate expansion of the expandable element 370 during expansion of the balloon 366. As with the embodiment of FIG. 18C, the positioning of the expandable element 370 relative to the balloon 366 obviates a need for an outer shaft. Rather, ITEV placement of the extension electrodes is achieved by inflating the balloon 366.

Referring now to FIGS. 19A and 19B, an alternative ITEV PEF 400 system is described comprising an expandable stent. The ITEV PEF system 400 comprises a stent 402 having extensions 404 configured to pierce the wall of a patient's vasculature upon expansion of the stent. The extensions 404 may be proximal and distal extensions that form longitudinally spaced bipolar electrode pairs. Additionally, the extensions 404 can be electrically coupled to the PEF generator 50 and utilized as extravascular electrodes for delivery of PEF therapy.

As seen in FIG. 19A, a stent 402 may be delivered to an intravascular treatment site, such as a site within renal artery RA, in a reduced profile configuration. The stent 402 may, for example, be positioned on a delivery and deployment catheter, such as a balloon catheter 410, during advancement and deployment at the treatment site. The catheter 410 may (temporarily) electrically couple the stent to the PEF generator. As seen in FIG. 19B, when the stent 402 is properly positioned at the treatment site, it may be deployed to contact the vessel wall (e.g., via the deployment catheter) such that extensions 404 penetrate the wall of the vessel. This accordingly positions the extension electrodes extravascularly via an ITEV approach. PEF therapy then may proceed, and upon completion the catheter 410 may be collapsed and removed from the patient.

The system 400 facilitates repeat PEF therapy at a later time. For example, by temporarily electrically re-coupling the catheter 410 or some other electrical coupling element to the stent 402, the system 400 can repeat PEF therapy as desired. When utilized to achieve renal denervation, such repeat therapy may, for example, be repeated upon evidence of re-innervation of the renal(s).

Although preferred illustrative variations of the present invention are described above, it will be apparent to those skilled in the art that various changes and modifications may be made thereto without departing from the invention. For example, although the variations primarily have been described for use in combination with pulsed electric fields, it should be understood that any other electric field may be delivered as desired. It is intended in the appended claims to cover all such changes and modifications that fall within the true spirit and scope of the invention.

We claim:

1. A renal neuromodulation apparatus, comprising:
    an elongated element configured to be intravascularly positioned within a blood vessel of a human patient;
    an electrode at a distal region of the elongated element and electrically coupleable to an electric field generator external to the patient,
    wherein the electrode comprises an intravascular region associated with the elongated element and an extravascular region adapted to be passed through a wall of the blood vessel; and
    an expansion element associated with the electrode and configured to move the electrode between—
        a low-profile arrangement in which the extravascular region of the electrode is within the blood vessel, and
        a treatment arrangement in which the extravascular region of the electrode is located at an extravascular location for extravascular delivery of an electric field.

2. The renal neuromodulation apparatus of claim 1 wherein the expansion element comprises an inflatable balloon.

3. The renal neuromodulation apparatus of claim 1 wherein the expansion element comprises an expandable cage or basket.

4. The renal neuromodulation apparatus of claim 1 wherein the expansion element comprises a self-expanding basket or cage.

5. The renal neuromodulation apparatus of claim 1 wherein the extravascular region of the electrode comprises a sharpened point for penetrating the wall of the blood vessel.

6. The renal neuromodulation apparatus of claim 1 wherein the electrode comprises a bipolar electrode pair having a first electrode element and a second electrode element.

7. The renal neuromodulation apparatus of claim 6 wherein, in the treatment arrangement, the first electrode element and the second electrode element are angularly aligned and longitudinally spaced apart from one another.

8. The renal neuromodulation apparatus of claim 6 wherein the bipolar electrode pair is a first bipolar electrode pair, and wherein the apparatus further comprises a second bipolar electrode pair angularly offset from the first bipolar electrode pair, and further wherein the second bipolar electrode pair comprises a third electrode element and a fourth electrode element.

9. The renal neuromodulation apparatus of claim 1 wherein the elongated element is configured to be intravascularly positioned within the blood vessel via a guide wire.

10. The renal neuromodulation apparatus of claim 1 wherein the electrode is configured for infusion of an agent before, during, and/or after delivery of the electric field.

11. The renal neuromodulation apparatus of claim 10 wherein the agent is adapted to enhance a neuromodulatory effect of the electric field.

12. The renal neuromodulation apparatus of claim 10 wherein the agent comprises saline.

13. The renal neuromodulation apparatus of claim 10 wherein the agent is adapted to provide a protective effect for non-target tissue during delivery of the electric field.

14. The renal neuromodulation apparatus of claim 1 wherein the electrode is configured for monopolar delivery of the electric field.

15. The renal neuromodulation apparatus of claim 1 wherein the elongated element, electrode, and expansion element are sized and shaped for intravascular positioning within a renal artery of the patient.

16. The renal neuromodulation apparatus of claim 1 wherein the electric field is a pulsed electric field.

17. The renal neuromodulation apparatus of claim 1 wherein the elongated element is configured to be intravascularly positioned within a renal artery of the patient, and wherein the electrode is sized such that, when in the treatment arrangement, the extravascular region of the electrode is within adventitia of the renal artery.

18. The renal neuromodulation apparatus of claim 1 wherein the elongated element is configured to be intravascularly positioned within a renal artery of the patient, and wherein the extravascular region is adapted to deliver the electric field to one or more renal nerves of the patient to achieve renal denervation.

* * * * *